(12) United States Patent
Baron et al.

(10) Patent No.: US 9,770,422 B2
(45) Date of Patent: *Sep. 26, 2017

(54) COMPOSITIONS AND METHODS FOR TREATING METABOLIC DISORDERS

(71) Applicant: Elcelyx Therapeutics, Inc., San Diego, CA (US)

(72) Inventors: Alain D. Baron, San Diego, CA (US); Mark S. Fineman, San Diego, CA (US); Nigel R. A. Beeley, Solana, CA (US)

(73) Assignee: ELCELYX THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/968,696

(22) Filed: Dec. 14, 2015

(65) Prior Publication Data

US 2016/0095828 A1 Apr. 7, 2016

Related U.S. Application Data

(63) Continuation of application No. 13/734,966, filed on Jan. 5, 2013, now Pat. No. 9,211,263, which is a continuation-in-part of application No. 13/547,022, filed on Jul. 11, 2012, now Pat. No. 8,796,338, and a continuation-in-part of application No. 13/345,135, filed on Jan. 6, 2012, now abandoned.

(60) Provisional application No. 61/649,171, filed on May 18, 2012.

(51) Int. Cl.

| | | |
|---|---|---|
| *A61K 9/20* | (2006.01) | |
| *C07C 279/02* | (2006.01) | |
| *A61K 31/155* | (2006.01) | |
| *A61K 45/06* | (2006.01) | |
| *A61K 9/28* | (2006.01) | |
| *A61K 31/4196* | (2006.01) | |
| *A61K 31/53* | (2006.01) | |
| *A61K 31/55* | (2006.01) | |
| *C07D 317/58* | (2006.01) | |
| *C07D 405/12* | (2006.01) | |
| *C07D 249/14* | (2006.01) | |
| *C07D 251/10* | (2006.01) | |
| *C07D 251/18* | (2006.01) | |
| *C07D 255/02* | (2006.01) | |
| *C07D 307/52* | (2006.01) | |
| *A61K 31/36* | (2006.01) | |
| *A61K 9/00* | (2006.01) | |

(52) U.S. Cl.

CPC .......... *A61K 31/155* (2013.01); *A61K 9/0053* (2013.01); *A61K 9/2054* (2013.01); *A61K 9/282* (2013.01); *A61K 9/2813* (2013.01); *A61K 9/2846* (2013.01); *A61K 9/2866* (2013.01); *A61K 31/36* (2013.01); *A61K 31/4196* (2013.01); *A61K 31/53* (2013.01); *A61K 31/55* (2013.01); *A61K 45/06* (2013.01); *C07D 249/14* (2013.01); *C07D 251/10* (2013.01); *C07D 251/18* (2013.01); *C07D 255/02* (2013.01); *C07D 307/52* (2013.01); *C07D 317/58* (2013.01); *C07D 405/12* (2013.01)

(58) Field of Classification Search

None
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 6,451,808 | B1 | 9/2002 | Cowles |
| 6,475,521 | B1 | 11/2002 | Timmins et al. |
| 6,676,966 | B1 | 1/2004 | Odidi et al. |
| 6,790,459 | B1 | 9/2004 | Cheng et al. |
| 7,060,295 | B2 | 6/2006 | Richardson et al. |
| 7,442,720 | B2 | 10/2008 | Chan et al. |
| 7,507,768 | B2 | 3/2009 | Li et al. |
| 7,799,782 | B2 | 9/2010 | Munson et al. |
| 7,829,530 | B2 | 11/2010 | Bachovchin et al. |
| 7,919,116 | B2 | 4/2011 | Chen et al. |
| 8,389,008 | B2 | 3/2013 | Baichwal et al. |
| 8,475,841 | B2 | 7/2013 | Cheng et al. |
| 8,796,338 | B2 | 8/2014 | Baron et al. |
| 8,846,695 | B2 | 9/2014 | Dugi |

(Continued)

FOREIGN PATENT DOCUMENTS

| | | |
|---|---|---|
| CA | 2382098 A1 | 3/2001 |
| CA | 2651019 A1 | 11/2007 |

(Continued)

OTHER PUBLICATIONS

Ali, et al., "Formulation and development of hydrodynamically balanced system for metformin: In vitro and in vivo evaluation," Europ. J. of Pharmaceutics and Biopharmaceutics 67:196-201 (2007).

Bailey CJ, Mynett KJ, Page T., "Importance of the intestine as a site of metformin-stimulated glucose utilization," Br J Pharmacol. 112: 671-675 (1994).

Bailey, et al., "Metformin," N Engl J Med , vol. 334, No. 9: 574-9 (1996).

Becker, et al. "Pharmacogenetics of Oral Antidiabetic Drug," International Journal of Endocrinology vol. 2013, Article ID 686315, 10 pages.

(Continued)

*Primary Examiner* — H. Sarah Park
(74) *Attorney, Agent, or Firm* — Todd A. Lorenz

(57) ABSTRACT

Methods for improving the gastrointestinal tolerability of biguanide compounds and for treating metabolic disorders and/or inducing weight loss in patients in need thereof, particularly in individuals having a contraindication for treatment with biguanide compounds, are provided comprising administering delayed release formulations of such biguanide compounds, including metformin, targeted to the small intestine.

23 Claims, 19 Drawing Sheets

(56) References Cited

U.S. PATENT DOCUMENTS

| | | |
|---|---|---|
| 9,050,292 B2 | 6/2015 | Baron et al. |
| 9,056,134 B2 | 6/2015 | Duarte-Vazquez et al. |
| 9,211,263 B2 | 12/2015 | Baron et al. |
| 2002/0177602 A1 | 11/2002 | Piper |
| 2003/0077335 A1 | 4/2003 | Richardson et al. |
| 2003/0113366 A1 | 6/2003 | Macgregor |
| 2004/0081697 A1 | 4/2004 | Lewis et al. |
| 2004/0156900 A1 | 8/2004 | Shanghvi et al. |
| 2006/0094782 A9 | 5/2006 | Wong et al. |
| 2006/0222709 A1 | 10/2006 | Devane |
| 2007/0141154 A1 | 6/2007 | Li et al. |
| 2007/0172525 A1 | 7/2007 | Sesha |
| 2008/0038739 A1 | 2/2008 | Li et al. |
| 2008/0064701 A1 | 3/2008 | Sesha |
| 2008/0113026 A1 | 5/2008 | McKinney et al. |
| 2008/0166416 A1 | 7/2008 | Lizio et al. |
| 2008/0274180 A1* | 11/2008 | Jathar ............... A61K 9/2009 424/468 |
| 2009/0220611 A1 | 9/2009 | Dargelas et al. |
| 2010/0113603 A1 | 5/2010 | Aronne |
| 2010/0184796 A1 | 7/2010 | Behrens et al. |
| 2010/0254916 A1 | 10/2010 | Karanewsky et al. |
| 2010/0256014 A1 | 10/2010 | Tennagels et al. |
| 2010/0267643 A1 | 10/2010 | Baron et al. |
| 2010/0331419 A1 | 12/2010 | Aronne |
| 2010/0331420 A1 | 12/2010 | Aronne |
| 2011/0065731 A1 | 3/2011 | Dugi et al. |
| 2011/0082407 A1 | 4/2011 | Aronne |
| 2011/0250271 A1 | 10/2011 | Shanghvi et al. |
| 2011/0257432 A1 | 10/2011 | DiMauro |
| 2012/0177730 A1 | 7/2012 | Baron et al. |
| 2013/0177604 A1 | 7/2013 | Baron et al. |
| 2014/0193498 A1 | 7/2014 | Baron et al. |
| 2014/0235558 A1 | 8/2014 | Kim et al. |
| 2014/0235559 A1 | 8/2014 | Kim et al. |
| 2014/0294951 A1 | 10/2014 | Fayad et al. |
| 2014/0341986 A1 | 11/2014 | Baron et al. |
| 2015/0064223 A1 | 3/2015 | Baron et al. |
| 2015/0065578 A1 | 3/2015 | Baron et al. |
| 2015/0196509 A1 | 7/2015 | Baron et al. |
| 2015/0265555 A1 | 9/2015 | Baron et al. |
| 2017/0020829 A1 | 1/2017 | Baron et al. |

FOREIGN PATENT DOCUMENTS

| | | |
|---|---|---|
| CN | 1413582 A | 4/2003 |
| CN | 1561980 A | 1/2005 |
| CN | 1891229 A | 1/2007 |
| CN | 101 190 179 B | 6/2008 |
| CN | 101339178 A | 1/2009 |
| CN | 101590007 A | 12/2009 |
| CN | 101 695 575 A | 4/2010 |
| CN | 101785763 A | 7/2010 |
| CN | 101978956 A | 2/2011 |
| CN | 102188429 A | 9/2011 |
| CN | 102357088 A | 2/2012 |
| EP | 1591114 A1 | 12/2005 |
| JP | 2002-326927 A | 11/2002 |
| KR | 10-2007-0045940 | 5/2007 |
| WO | WO 98/57634 A1 | 12/1998 |
| WO | WO 00/28989 A1 | 5/2000 |
| WO | WO 01/21159 A2 | 3/2001 |
| WO | WO 01/32158 A2 | 5/2001 |
| WO | WO 01/35941 A2 | 5/2001 |
| WO | WO 03/004009 A1 | 1/2003 |
| WO | WO 03/004498 A1 | 1/2003 |
| WO | WO 03/026637 A2 | 4/2003 |
| WO | WO 03/039527 A1 | 5/2003 |
| WO | WO 03/005133 A1 | 6/2003 |
| WO | WO 03/045355 A1 | 6/2003 |
| WO | WO 03/068209 A1 | 8/2003 |
| WO | WO 03/075933 A1 | 9/2003 |
| WO | WO 2004/012715 A1 | 2/2004 |
| WO | WO 2004/110375 A2 | 12/2004 |
| WO | WO 2004/110422 A1 | 12/2004 |
| WO | WO 2005/023766 A1 | 3/2005 |
| WO | WO 2005/041923 A1 | 5/2005 |
| WO | WO 2005/060942 A1 | 7/2005 |
| WO | WO 2006/078811 A1 | 7/2006 |
| WO | WO 2006/082523 A1 | 8/2006 |
| WO | WO 2006/086727 A2 | 8/2006 |
| WO | WO 2006/104401 A1 | 10/2006 |
| WO | WO 2006/109175 A2 | 10/2006 |
| WO | WO 2008/057470 A2 | 5/2008 |
| WO | WO 2008/057968 A2 | 5/2008 |
| WO | WO 2008/058355 A2 | 5/2008 |
| WO | WO 2008/058358 A2 | 5/2008 |
| WO | WO 2008/113000 A1 | 9/2008 |
| WO | WO 2009/111200 A1 | 9/2009 |
| WO | WO 2010/045656 A2 | 4/2010 |
| WO | WO 2010/123930 A2 | 10/2010 |
| WO | WO 2011/002001 A1 | 1/2011 |
| WO | WO 2011/051966 A2 | 5/2011 |
| WO | WO 2011/159100 A2 | 12/2011 |
| WO | WO 2011/160093 A2 | 12/2011 |
| WO | WO 2012/094636 A2 | 7/2012 |
| WO | WO 2013/063527 A1 | 5/2013 |
| WO | WO 2013/103384 A1 | 7/2013 |
| WO | WO 2013/103919 A2 | 7/2013 |

OTHER PUBLICATIONS

Bhoyar, et al. "Formulation and In vitro Evaluation of Sustained Release Dosage Form with Taste Masking of Meformin Hydrochloride," Indian Journal of Pharmaceutical Sciences, Mar.-Apr. 2010: 184-190.

Bell, David S.H., "Metformin-Induced Vitamin B12 Deficientcy Presenting as a Peripheral Neuropathy," 103 South. Med. J. 265, abstract (2010).

Buler, et al., "Metforminreduces hepatic expression of SIRT3, the mitochondrial deacetylase controlling energy metabolism," Plos One, Nov. 2012 vol. 7, Issue 11.

Burcelin, R. "The antidiabetic gutsy role of metformin uncovered?" Gut Online First, published on Jul. 9, 2013.

Campbell, et al., "A Clinical Evaluation of a Delayed Release Preparation of Metformin," J INt. Med. Res (1), pp. 551-556 (1973).

Corti, et al., "Sustained-release matrix tablets of metformin hydrochloride in combination with triacetyl-β-cyclodextrin," Europ. J. of Pharmaceutics and Biopharmaceutics 68:303-309 (2008).

Davidson, et al., "Steady-state pharmacokinetics of a novel extended-release metformin formulation", Br J Diabetes Vasc Dis (2004) 4:273-277.

DeFronzo, et al. "Delayed-Release Metformin May be Suitable for Use in Diabetes Patients with Renal Impairment Who are Contranducted for Currently Available Metformin Formulations," presented at the 73$^{rd}$ Annual Scientific Meeting of the American Diabetes Associaten, Jun. 21-25, 2013, in Chicago, IL.

DeFronzo, et al. "Dissociation Between Metformin Plasma Exposure and its Glucose-Lowering Effect: A Novel Gut-Mediated Mechanism of Action," presented at the 73$^{rd}$ Annual Scientific Meeting of the American Diabetes Associaten, Jun. 21-25, 2013, in Chicago, IL.

Di Colo, et al., "In vitro evaluation of a system for pH-controlled peroral delivery of metformin," Europ. J. pf Pharmaceutics and Biopharmaceutics 68:303-309 (2008).

Evonik Industries productin formation for Eudragit S 100, printed 2015.

Evonik Industries productin formation for Eudragit S 12,5, printed 2015.

Foretz, et al., "Metformin inhibits hepatic gluconeogenesis in mice independently of the LKB1/AMPK pathway via a decrease in hepatic energy state," J. of Clinical Investigation; 120(7):2355-2369 (2010).

Geraedts, et al. "Release of Satiety Hormones Induced by the Five Basic Tastants Is Controlled by the Influx of Calcium," Gastroenterology, Elsevier, Philadelphia, PA, vol. 136, No. 5, May 1, 2009, p. A-25.

Hong, et al., "Population exposure-response modeling of metformin in patients with type 2 diabetes mellitus," J Clin Pharmacol. 48: 696-707 (2008).

(56) References Cited

OTHER PUBLICATIONS http://www.aqnovel.com/mytag.php?id=46161.
http://www.chem02.com/en/product/hormones/2010/1103/97693.html.
http://www.chemyq.com/En/xz/xz13/122367peabr.htm.
http://www.weiku.com/products/10476375/METFORMIN_HYDROCHLORIDE_ENTERIC_COATED_TABLET.html.
Hu, et al, "Preparation and in vitro/in vivo evaluation of sustained-release metformin hydrochloride pellets," Europ. J. of Pharmaceutics and Biopharmaceutics 64:185-192 (2006).
Ibekwe, et al. "A comparative in vitro assessment of the drug relase performance pH-responsive polymers for ileo-colonic dlivery," Intl. J. Pharma., 308: pp. 52-60 (2006).
Karlsson, et al. "Effects of Metformin and Rosiglitazone Treatment on Insulin Signaling and Glucose Uptake in Patients With Newly Diagnosed Type 2 Diabetes," Diabetes, May 2005, vol. 54, p. 1459.
Karttunen, et al. "The influence of pharmaceutical formulation on the gastrointestinal side effect of metformin" Acta Endocrinol.; 94: (Suppl 237) 42 (1980).
Karttunen, et al., "The pharmacokinetics of metformin: a comparison of the properties of a rapid-release and a sustained-relese preparation," Int. J. Clin. Pharmacol. Ther. Toxicol. 21:31-36 (1983).
Lee, et al., "Metformin Decreases Food Consumption and Induces Weight Loss in Subject with Obesity with Type II Non-Insulin-Dependent Diabetes," Obesity Research, vol. 6, No. 1, pp. 47-53, Jan. 1998.
Levy, et al., "Assessment of efficacy and tolerability of once-daily extended release metformin in patients with type 2 diabetes mellitus", Dibetology & Metabolic Syndrome; 2:16 (2010).
Li, et al, "Meta-Analysis: Pharmacologic Treatment of Obesity," Ann. Intern Med.; 142:532-546 (2005).
Li, et al. "AMPK Phosphorylates and Inhibits SREBP Activity to Attenuate Hepatic Steatosis and Atherosclerosis in Diet-induced Insulin Resistant Mice," Cell Metab. Apr. 6, 2011; 13(4): 376-388.
Mannucci, et al. "Effects of metformin on glucagon-like peptide-1 levels in obese patients with and without Type 2 diabetes," Diabetes Nutr Metab;17:336-42 (2004).
Marathe, et al., "Effect of altered gastric emptying and gastrointestinal motility on metformin absorption," Br. J. Clin. Pharmacol. 50:325-332 (2000).
Marchetti, et al. "Plasma biguanide levels are correlated with metabolic effects in diabetic patients," Clin Pharmacol Ther.; 41: 450-454 (1987).
Miller, et al. "Biguanides suppress hepatic glucagon signaling by decreasing production of cyclic AMP," Nature Feb. 14, 2013; 494(7436): 256-260.
Mu, et al., "Anti-Diabetic efficacy and impact on amino acid metabolism of GRA1, a novel small-molecule glucagon receptor antagonist," Plos One, Nov. 2012, vol. 7, Issue 11.
Mulherin, et al. "Mechanisms Underlying Metformin-Induced Secretion of Glucagon-Like Peptide-1 from the Intestinal L Cell," Endocrinology, Dec. 2011; 152(12):4610-4619.
Natali, et al. CAS: 145: 179868 (2006).
Nauck, et al. CAS: 154: 426492 (2010).
Neary, et al. "Gut homrones: implications for the treatment of obesity," Phrmacol Ther ;124:44-56 (2009).
Nicoluccil, et al., "Incretin-based therapies: a new potential treatment approach to overcome clinical inertia in type 2 diabetes," Acta Biomedica; 79(3):184-91 (2008).
Noel, et al., "Kinetic study of normal and sustained relase dosage forms of metformin in normal subjects," Res. Clin. Forums 1:35-50 (1979).
Owen, et al. "Evidence that metformin exerts its anti-diabetic effects through inhibition of complex 1 of the mitochondrial respiratory chain," Biochem J. 348 Pt 3: 607-614 (2000).
Pentikainen, "Bioavailability of metformin. Comparison of solution, rapidly dissovling tablet, and three sustained release products," Int. J. Clin. Pharmacol. Ther. Toxicol. 24:213-220 (1986).

Perriello, G., "Mechanisms of metformin action in non-insulin-dependent diabetes mellitus," Diabetes Metab Rev.; 11 Suppl 1: S51-S56 (1995).
"Prescription Medications for the Treatment of Obesity," NIH Publication No. 07-491, Dec. 2007.
Pyra, et al., "Prebiotic Fiber Increases Hepatic Acetyl CoA Carboxylase Phosphorylation and Supresses Glucose-Dependent Insulinotropic Polypeptide Secretion More Effectively When Used with Metformin in Obese Rats[1,2]" J. Nutr. 142:213-220 (2012).
Rena, et al. "Molecular mechanism of action of metformin: old or new insights?" Diabetologia; 56:1898-1906 (2013).
Rozengurt, "Taste Receptors in the Gastrointestinal Tract. I. Biter taste receptors and α-gustducin in the mammalia gut," Am J Physiol. Gastrointest Liver Physiol 291: G171-G177 (2006).
Scarpello, JH "Review: Optimal dosing strategies for maximising the clinical response to metformin in type 2 diabets," British J Diab Vasc Disease.; 1: 28 (2001).
Scarpello, et al. "Metformin therapy and clinical uses," Diabetes Vasc Dis Res;5:157-67 (2008).
Scheen, Clin. Pharmacokinet. 30:359-71 (1996).
Shaw, et al. "The Kinase LKB1 Mediates Glucose Homeostasis in Liver and Therapeutic Effects of Metformin," Science. Dec. 9, 2005; 310(5754): 1642-1646.
Shaw, et al. "Metformin trims fats to restore insulin sensitivity," Nature Medicine. Dec. 2013; vol. 19, No. 12: 1570-1572.
Shu, et al. Effect of genetic variation in the organic cation transporter 1 (OCT1) on metformin action. J Clin Invest.; 117: 1422-1431 (2007).
Singer, et al., "Comparative studies of the effect of N1-n-butylbiguanide hydrochloride (Buformin) and N1-n-butylbiguanide tosylate (Buformin retard)," Z Gesamete Inn Med., 28(16): pp. 504-506 (1973).
Stepensky, et al "Preclinical evaluation of pharmacokinetic-pharmacodynamic rationale for oral CR metformin formulation," J Control Release. Mar. 12, 2001; 71(1):107-15.
Stepensky, et al., "Pharmacokinetic-pharmacodynamic analysis of the glucose-lowering effect of metformin in diabetic rats reveals first-pass pharmacodynamic effect", Drug Metabolism and Dispositioin, 30(8): 861-868 (2002).
Tennagels, et al. CAS:150:207438 (2009).
Timmins, et al., "New prolonged-release metformin improves gastrointestinal tolerability", Clin. Pharmcokinet; 44:721-729 (2005).
Tsilchorozidou, et al. "Metformin increases fasting plasma peptide tyrosine tyrosine (PYY) in women with polycystic ovarian syndrome (PCOS)," Clin Endocrinol (Oxf);69:936-42 (2008).
Tucker, et al., "Metformin kinetics in healthy subjects and in patients with diabetes mellitus," Br. J. Clin. Pharmacol. 12:235-246 (1981).
Ubl, et al "Anti-diabetic biguanides inhitib hormone-induced intracellular $Ca^{2+}$ concentration oscillations in rat hepatocytes," Biochem. J; 304, 561-567 (1994).
Viollet, et al "Revisiting the mechanisms of metformin action in the liver," Annales d'Endocrinologie 74: 123-129 (2013).
Wang, et al., "Involvement of organic cation transporter 1 in hepatic and intestinal distribution of metformin," J Pharmacol Exp Ther.; 302: 510-515 (2002).
Zakeri-Milani, et al. "In-vitro bioequivalence study of 8 brands of metformin tablets in Iran market," Journal of Applied Pharmaceutical Science 02 (08): 194-197 (2012).
Zander, et al., "Additive glucose-lowering effects of glucagon-like peptide-1 and metformin in type 2 diabetes," Diabetes Care,;vol. 24, No. 1: 720-725 (2001).
U.S. Appl. No. 15/339,346, entitled, "Biguanide Compositions and Methods of Treating Metabolic Disorders," filed Oct. 31, 2016, of Elcelyx Therapeutics, Inc.
U.S. Appl. No. 15/339,378, entitled, "Biguanide Compositions and Methods of Treating Metabolic Disorders," filed Oct. 31, 2016, of Elcelyx Therapeutics, Inc.
U.S. Appl. No. 15/433,987, entitled, "Compositions Comprising Statins, Biguanides and Further Agents for Reducing Cardiometabolic Risk," filed Feb. 15, 2016, of Elcelyx Therapeutics, Inc.

(56) References Cited

OTHER PUBLICATIONS

Blonde et al., "Gastrointestinal tolerability of extended-release metformin tablets compared to immediate-release metformin tablets: results of a retrospective cohort study," Current Medical Research and Opinion, vol. 20, No. 4, pp. 565-572, (2004).

Di Colo, et at., "A site-specific controlled-release system for metformin," J. of Pharmcy and Pharmacology, vol. 57, pp. 565-571, (2005).

Vidon et al, "Metformin in the digestive tract," Diabestes Research and Clinical Practice, vol. 4, pp. 223-229, (1988).

\* cited by examiner

Randomized, double-blind, 2-period crossover study
N = 18

Events of Treatment Period

| Day 1 | Day 2 | Day 3 | Day 4 | Day 5 |
|---|---|---|---|---|
| 500 mg BID | 500 mg BID | 1000 mg BID | 1000 mg BID | 1000 mg |

Mixed Meal challenge before
first dose of met
(~1000 kcal meal)
Measure: PYY, GLP-1a, GLP-1t,
glucose, insulin, TG Mixed Meal challenge 4 hours
after last dose of met
(~1000 kcal meal)
Measure: Met PK, PYY, GLP-1a,
GLP-1t, glucose, insulin, TG Met IR ↑53% in Abs AUC, p<0.001

Met DR

↑48% in Abs AUC, p=0.004

Met IR

↑33% in Abs AUC, p=0.028

Met DR

↑27% in Abs AUC, p=0.153

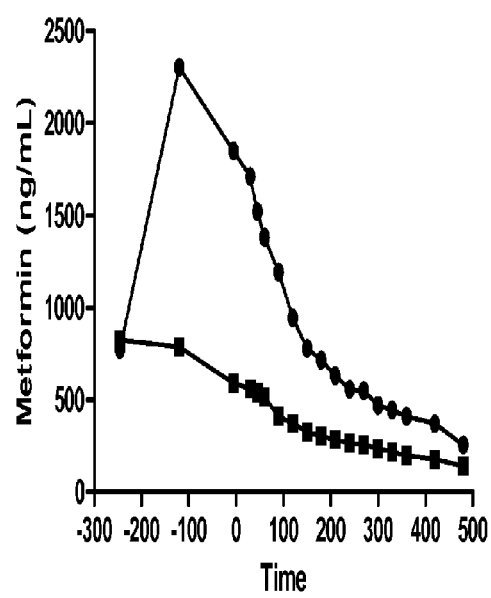 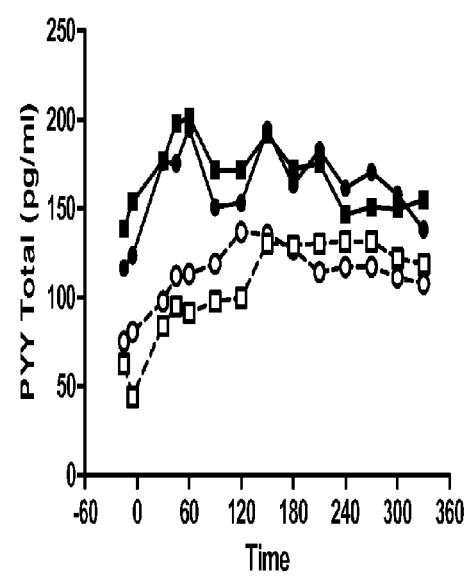
FIG. 7A
FIG. 7B
◇ Baseline1  ● Met IR
□ Baseline2  ■ Met DR

COMPOSITIONS AND METHODS FOR TREATING METABOLIC DISORDERS

FIELD OF THE INVENTION

The present invention relates generally to the treatment of metabolic disorders with biguanide compounds, and to improving the gastrointestinal tolerability of such compounds, by administering biguanide compounds to patients using delayed-release formulations.

BACKGROUND OF THE INVENTION

Hyperglycemia, hyperglycaemia, or high blood sugar, is a condition in which an excessive amount of glucose, e.g., greater than about 125 mg/dL, circulates in the blood plasma. Chronic hyperglycemia at levels that are more than slightly above normal can produce a wide variety of serious complications over a period of years, including kidney damage, neurological damage, cardiovascular damage, damage to the retina, or damage to the feet and legs. Diabetic neuropathy may be a result of long-term hyperglycemia.

Hyperglycemia may be caused by or associated with dysfunction of the thyroid, adrenal, and pituitary glands, diseases of the pancreas, severe sepsis, and intracranial diseases such as encephalitis, brain tumors, and meningitis. By far the most common cause of chronic hyperglycemia is diabetes mellitus, which is widely considered by many to be a looming health care epidemic. In diabetes mellitus, the hyperglycemia typically results from low insulin levels (type I diabetes) and/or insulin resistance at the cellular level (type II diabetes).

Many type II diabetes medications are designed to lower blood glucose levels. A first line drug of choice for the treatment of type II diabetes, and the most commonly prescribed antidiabetic medication in the world, is metformin. In contrast to most diabetes medications, hypoglycemia with metformin is rare; it is also weight neutral and is associated with reduced cardiovascular events and reduced mortality.

Metformin (dimethylbiguanide) belongs to a class of biguanide drugs developed based on a glucose-lowering extract containing guanidines from the *Galega officinalis* plant. (Bailey & Turner Metformin. *N Engl J Med*. 1996 Feb. 29; 334(9):574-9; Bailey et al. Metformin: its botanical background. *Practical Diabetes Int*. 2004; 21(3):115-7). Originally synthesized as a side product in 1921, (Werner E, Bell J. The preparation of methylguanidine, and of ββ-dimethylguanidine by the interaction of dicyanodiamide, and methylammonium and dimethylammonium chlorides respectively. *J Chem Soc*, Transactions. 1921; 121:1790-5), metformin and other biguanides were found to lower blood glucose in animals. Studies on the glucose-lowering effects of metformin, phenformin and buformin in humans were published in the 1950s. At first, the greater potency of phenformin and buformin resulted in their more widespread use; however, their association with lactic acidosis ultimately led to discontinuation in most countries by the end of the 1970s.

Metformin improves glucose tolerance in patients by lowering both basal and postprandial plasma glucose. Metformin monotherapy generally lowers fasting blood glucose by 20% and HbA1c levels by approximately 1.5%. (Bailey & Turner, supra; DeFronzo & Goodman Efficacy of metformin in patients with non-insulin-dependent diabetes mellitus. The Multicenter Metformin Study Group. *N Engl J Med*. 1995 Aug. 31; 333(9):541-9). Metformin has also been shown to improve serum lipids, decreasing triglycerides, free fatty acids, and LDL-cholesterol and modestly increasing HDL-cholesterol. (Bailey & Turner, supra.)

Metformin's antihyperglycemic effects have been postulated to result from a wide variety of systemic biochemical interactions including, e.g., suppressing glucose production by the liver, increasing insulin sensitivity, enhancing peripheral glucose uptake (by phosphorylating GLUT-4 enhancer factor), increasing fatty acid oxidation, and/or decreasing absorption of glucose from the gastrointestinal tract. (Hundal & Inzuecchi Metformin: new understandings, new uses. *Drugs*. 2003; 63(18):1879-94). More recently, investigators have focused on its apparent impact on the secretion of glucagon-like peptide-1 (GLP-1), apparently determining that metformin does not act directly on L cells in the gut to induce GLP-1 secretion or enhance L cell sensitivity to several known secretagogues. (Mulherin et al., Mechanisms underlying metformin-induced secretion of glucagon-like peptide-1 from the intestinal L cell. *Endocrinology* 152: 4610-19 (December 2011)). These investigators suggested that metformin stimulates GLP-1 release through an indirect mechanism involving both muscarinic (M3) receptor-dependent and Gastrin Releasing Peptide (GRP) pathways independent of intestinal L cells, such that systemic bioavailability of metformin is critical to therapeutic efficacy.

Unfortunately, however, systemic exposure of metformin still poses a serious risk of lactic acidosis for several patient populations. Lactic acidosis is a potentially fatal metabolic complication that occurs when lactic acid levels increase in the bloodstream. Accordingly, metformin is contraindicated in people with any condition that could increase the risk of lactic acidosis, including kidney disorders, lung disease, and liver disease. According to the prescribing information, heart failure, in particular, unstable or acute congestive heart failure, also increases risk of lactic acidosis with metformin. Thus, metformin remains unavailable to treat hyperglycemia in patients with these contraindications.

Moreover, conventional metformin formulations often produce dose-limiting adverse gastrointestinal (GI) complications including diarrhea, nausea, vomiting, dizziness, headaches and dyspepsia. Accordingly, patient administration is generally titrated upward over a period of time to a maximum tolerated dose based in not insignificant part on any resulting patient-specific adverse GI effects. Extended-release formulations have been developed in the hopes of addressing this, but have not adequately resolved these problems.

Clearly, there continues to be a need for better and safer compositions and methods for delivering biguanide compounds that address these tolerability and safety concerns. Ideally, these would also provide more effective treatment options for metabolic disorders in patients having contraindications for metformin and/or other biguanides.

SUMMARY OF THE INVENTION

As demonstrated herein for the first time, the present inventors have surprisingly discovered that the systemic bioavailability of biguanides such as metformin can be minimized without compromising their therapeutic efficacy. Correspondingly, methods and compositions are provided for the treatment of metabolic disorders in patients, including otherwise contraindicated patient populations, by administering delayed-release (DR) formulations to minimize the systemic bioavailability of the biguanide compound in the patient.

Also demonstrated herein for the first time is the surprising finding that GI complications typically resulting from biguanide administration can be dramatically reduced using the subject compositions and methods. Accordingly, patient comfort and compliance is greatly improved, as is therapeutic efficacy. Correspondingly, methods and compositions are provided for improving the GI tolerability of, and/or reducing GI complications resulting from, biguanide administration, by administering delayed-release formulations comprising a biguanide compound to minimize the systemic bioavailability of the compound in the patient.

The biguanide compounds of the disclosure may be administered to a subject in need thereof to treat various metabolic disorders, including obesity, dislipidemia or other disorders of lipid metabolism as well as hyperglycemic conditions and histopathological diseases associated with hyperglycemia, including type II diabetes, prediabetes, gestational diabetes and polycystic ovary syndrome. Particularly in view of the surprising and unexpected decoupling of systemic bioavailability and therapeutic efficacy achieved herein, and consequent improvement in the toxicity and safety profile, the effective use of biguanide compounds for prophylaxis and prevention of such diseases and disorders, as well as for more general weight loss purposes in overweight or mildly to severely obese individuals, is also explicitly contemplated.

Accordingly, in one aspect, provided herein are methods of treating metabolic disorders in a patient in need thereof, including contraindicated patients, comprising administering a therapeutically effective amount of a biguanide compound to said patient in a delayed-release formulation, wherein said administration minimizes the systemic bioavailability of the biguanide compound in the patient. In another aspect, methods of improving the GI tolerability of biguanide compounds and/or reducing GI complications resulting from biguanide administration are provided, comprising administering a therapeutically effective amount of a biguanide compound to a subject in a delayed-release formulation, wherein said administration minimizes the systemic bioavailability of the biguanide compound in the patient. Suitable biguanide compounds for use in the subject methods include, e.g., metformin, phenformin, buformin or imeglimin, including analogs, salts, solvates, polymorphs, hydrates, N-oxides, and prodrugs of such compounds.

In preferred embodiments, the biguanide compound has a reduced relative bioavailability of 70%, 60%, 50%, 40%, 30%, 20% or 10% in the subject delayed-release formulation compared to a conventional immediate-release (IR) or extended-release (XR) composition having the same amount of the biguanide compound. In particular embodiments, administration of the subject delayed-release formulation minimizes the mean plasma AUC, the mean plasma $C_{max}$ and/or the circulating plasma concentration of the biguanide compound in said patient compared to an identical protocol administering an IR or XR formulation having the same amount of the biguanide compound. In preferred embodiments, the biguanide compound is metformin, the IR composition is Glucophage® and the XR composition is Glucophage® XR.

In one embodiment, the mean plasma $AUC_{0-36}$ of the biguanide compound is less than about 15,000 ng*h/mL or 14,000 ng*h/mL, preferably less than about 12,000 ng*h/mL, more preferably less than about 11,000 ng*h/mL or 10,500 ng*h/mL, and most preferably less than about 10,000 ng*h/mL when administered at 2000 mg total daily dose (TDD) or 1000 mg twice a day (bis in die; abbreviated as "b.i.d" or "BID"). In another embodiment, the mean plasma $AUC_{0-36}$ of the biguanide compound is less than about 10,000 ng*h/mL, preferably less than about 9,000 ng*h/mL, more preferably less than about 8,000 ng*h/mL or 7,000 ng*h/mL, and most preferably less than about 6,000 ng*h/mL or 5,000 ng*h/mL when administered at 1000 mg TDD, 500 mg BID or lower effective doses.

In one embodiment, the mean plasma $C_{max}$ of the biguanide compound is less than about 1100 ng/mL, preferably less than about 1000 ng/mL, more preferably less than about 950 ng/mL, and most preferably less than about 900 ng/mL when administered at 2000 mg TDD or 1000 mg BID. In another embodiment, the mean plasma $C_{max}$ of the biguanide compound is less than about 800 ng/mL, preferably less than about 700 ng/mL, more preferably less than about 600 ng/mL, and most preferably less than about 600 ng/mL or 500 ng/mL when administered at 1000 mg TDD, 500 mg BID or lower effective doses.

In one embodiment, the resulting circulating plasma concentration of the biguanide compound is below about 5 μg/ml or 4 μg/ml, preferably below about 3 μg/ml or 2.5 μg/ml, more preferably below about 2 μg/ml, 1 μg/ml, 0.5 μg/ml, or 0.25 μg/ml in the patient.

The methods and compositions disclosed herein are particularly suitable for patients having a contraindication for the biguanide compound, e.g, metformin, phenformin or buformin. Such contraindication may be a hypoxic condition, impaired lactate clearance, and/or impaired clearance of the biguanide compound, e.g., impaired metformin clearance.

For example, in one embodiment, the methods disclosed herein may be used to treat a patient who may have a hypoxic condition, such as but not limited to respiratory failure and heart failure. In another embodiment, the patient may have impaired lactate clearance. In another embodiment, the patient may suffer from liver failure, which may result in impaired lactate clearance. In another embodiment, the patient may have impaired clearance of the biguanide compound, which may be caused, e.g., by renal impairment and/or kidney disease. Accordingly, in one embodiment the patient may have renal impairment. Such renal impairment may be moderate or severe renal impairment, or endstage renal disease. In another embodiment, the patient may have kidney disease, which may be chronic. In another embodiment, the patient may have hyperglycemia, which may be chronic, and which may be caused by type II diabetes.

Accordingly, provided herein are methods of treating a renally impaired subject having diabetes, comprising administering a therapeutically effective amount of a biguanide compound, e.g., metformin, phenformin, buformin, or imeglimin, in a delayed-release formulation to said subject. In certain embodiments, the subject has moderate renal impairment, severe renal impairment, or end stage renal disease. In other embodiments, the subject has a serum creatinine concentration of greater than 1.2 mg/dL when the subject is male, or has a serum creatinine concentration of greater than 1.1 mg/dL when the subject is female. In another embodiment, the subject has a decrease in glomerular filtration rate (GFR) as compared to a normal baseline level. In another embodiment, the subject has an increase in urinary protein as compared to a normal baseline level.

Also provided herein are methods of treating a diabetic subject having congestive heart failure, a hypoxic state and/or advanced liver disease, comprising administering a therapeutically effective amount of a biguanide compound, e.g., metformin, phenformin, buformin or imeglimin, in a delayed-release formulation to said subject.

Another method of treating provided herein is a method of reducing the onset of diabetes in a subject with pre-diabetes, comprising administering a therapeutically effective amount of a biguanide compound, e.g., metformin, phenformin, buformin or imeglimin, in a delayed-release formulation to said subject.

Also provided herein are methods of inducing weight loss in a subject, comprising administering a therapeutically effective amount of a biguanide compound in a delayed-release formulation to said subject. In some embodiments, the weight loss induced results in over 5 pounds lost in the subject, e.g., over 10 pounds lost, preferably over 25 pounds lost, and even more preferably over 50 pounds lost. In other embodiments, the induced weight loss results in the subject having a body mass index between 18.5 and 24.9. In another embodiment, the weight loss induced results in at least a loss of at least 0.5 inches in the waist circumference.

Administration of the subject formulations may be twice daily (b.i.d.), in the morning and evening, or once daily (omni in die, abbreviated as "OD"). In certain preferred embodiments, administration may be once daily in the morning, e.g., before 1 pm, preferably before 12 noon or 11 am, more preferably before 10 or 9 am, or with the morning meal. In other preferred embodiments, administration may be once daily in the evening, e.g., after 5 pm, more preferably after 6 pm or 7 pm, or with the evening meal. In another preferred embodiment, administration may be once daily at bedtime.

The subject methods administer therapeutically effective amounts of the biguanide compound(s). Notably, however, the inventive methods provided herein advantageously allow for lower therapeutic doses than prior art formulations, both on a per unit basis and/or on a daily dose basis. In certain embodiments of the methods disclosed herein, the biguanide compound is administered twice daily in an oral dosage form at a per unit dose greater than 500 mg BID, e.g. 600 or 800 mg BID. In certain preferred embodiments of the methods disclosed herein, the twice daily oral dosage is less than 500 mg BID, e.g., less than 400 mg BID, e.g., less than 300 mg BID, e.g., about 150, 200 or 250 mg BID. In alternative preferred embodiments, the biguanide compound is administered once a day at a per unit dose of 75 mg OD, 125 mg OD, 250 mg OD, 300 mg OD, 500 mg OD, 600 mg OD, 750 mg OD, 800 mg OD. or 1000 mg OD. In additional embodiments, the total daily dose (TDD) of the biguanide compound is less than 2000 mg/day, preferably less than 1500 mg/day, more preferably less than 1000 or 750 mg/day, most preferably less than 500, 400, 300, or 200 mg/day.

In any of the methods disclosed herein, the delayed-release formulations may be enterically coated. In one embodiment, the biguanide compound is targeted for delivery to the small intestine, and the formulation comprises an oral dosage form enterically coated at a pH at or above 5.0, 5.5, or 6.0, e.g., a pH 5.0 enteric coating, a pH 5.5 enteric coating, a pH 6.0 enteric coating, a pH 6.5 enteric coating, or a pH 7.0 enteric coating, or combinations thereof. In another embodiment, the oral dosage form may further comprise an extended-release component for the biguanide compound. In preferred embodiments, the biguanide compound is targeted for delivery to the distal small intestine, and the formulation comprises an oral dosage form enterically coated at a pH at or above 6.0 or 6.5.

In the methods disclosed herein, the biguanide compound may be or comprise metformin, a metformin salt, solvate, polymorph, hydrate, N-oxide or prodrug. In preferred embodiments, the biguanide compound is a metformin salt selected from the group consisting of hydrochloride, phosphate, sulfate, hydrobromide, salicylate, maleate, benzoate, succinnate, ethanesulfonate, fumarate, glycolate, palmoate, oratate, acetate, isobutyrate, acetylsalicylate, nicotinic acid, adamantoate, zinc-chlorophylin, carboxylic acid, benzoic acid, dichloroacetic acid, theophylin-7-acetate, clofibrate, tartate, oxalate, tannate and hydroxyl acid. In a particularly preferred embodiment, the biguanide compound is metformin hydrochloride.

The methods disclosed herein may also further comprise the administration of an immediate-release, extended release or delayed-release formulation of one or more additional therapeutic agents, e.g., a DPP-1V inhibitor (e.g., sitagliptin, saxagliptin, berberine, vildagliptin, linagliptin, alogliptin, and the like), a chemosensory receptor ligand (e.g., a sweet receptor ligand, bitter receptor ligand, umami receptor ligand, sour receptor ligand, fat receptor ligand or bile acid receptor ligand), an anti-obesity or anti-diabetes agent, or a chemosensory receptor antagonist, e.g., lactisole. Non-limiting examples include embodiments further comprising the administration of 100 mg sitagliptin OD, or 50 mg sitagliptin BID. The delayed-release formulation can be a bilayer tablet, or a capsule with the two components as encapsulated mini-tablets. The delayed-release formulation may also further comprise an immediate release component that has a pH 5.0 enteric coating for the additional therapeutic agent.

BRIEF DESCRIPTION OF THE DRAWINGS

FIG. 7A shows the plasma concentration of Metformin IR (●) and Metformin DR (■) (x-axis; ng/mL) as a function of time (y-axis; min) after ingestion at t=−240 and after a meal at t=0 min. FIG. 7B shows the plasma concentration of PYY (x-axis; pg/mL) as a function of time (y-axis; min) in subjects at baseline (□,○) or after ingestion of either Metformin IR (●) or Metformin DR (■) and after a meal at t=0 min.

DETAILED DESCRIPTION

Figure 1:
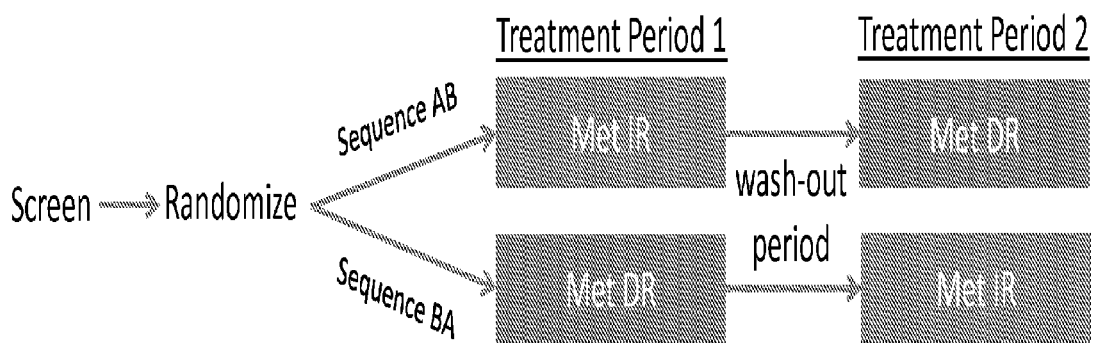
FIG. 1 shows the design of the study described in Example 1.

Contemplated herein are methods and compositions that minimize the systemic bioavailability of biguanide compounds, such as metformin, in subjects yet still provide significant salutary metabolic effects, e.g. reducing hyperglycemia. Contrary to conventional understanding (see, e.g. Mulherin et al, supra), the biguanide compounds of the disclosure actually cause release of GLP-1 through a mechanism of action which may include interaction with the luminal or epithelial aspect (i.e., the gastrointestinal tract side) of enteroendocrine cells, and systemic bioavailability can therefore be minimized while still achieving meaningful therapeutic efficacy. Advantageously, the subject methods and compositions significantly improve GI tolerability and also reduce the possibility of adverse effects such as lactic acidosis, such that otherwise contraindicated patients can now be effectively treated.

Accordingly, provided herein are methods of improving the GI tolerability of biguanide compounds, and/or reducing GI complications resulting biguanide compound administration, comprising administering a therapeutically effective amount of a biguanide compound in a delayed-release formulation to a subject in need thereof; wherein said delayed-release formulation minimizes the systemic level of the compound in the subject. Also provided herein are methods of treating metabolic disorders in subjects, and particularly in subjects having a contraindication for biguanide compound(s), comprising administering a therapeutically effective amount of a biguanide compound in a delayed-release formulation to a subject in need thereof; wherein said delayed-release formulation minimizes the systemic level of the compound in the subject. In preferred embodiments, the biguanide compound is selected from the group consisting of metformin, buformin, phenformin and imeglimin, and is administered at lower doses and/or with lower bioavailability than currently indicated while still achieving the desired metabolic improvements.

Definitions

The terms "gastrointestinal tract" and "gut," as used herein, refer to the stomach and intestine. The "small" or "upper" intestine includes the duodenum, jejunum and ileum and the "large" or "lower" intestine includes the caecum, colon and rectum. The "distal" small intestine includes the jejunum and ileum.

"Treating" or "treatment" of any condition, disease or disorder refers, in some embodiments, to ameliorating the disease, disorder, or condition (i.e., arresting or reducing the development of the disease, disorder, or condition, or at least one of the clinical symptoms thereof). In other embodiments "treating" or "treatment" refers to ameliorating at least one physical parameter, which may or may not be discernible by the subject, including physical parameters that are undesired but not clinically significant. In yet other embodiments, "treating" or "treatment" refers to inhibiting the disease, disorder, or condition, either physically, (e.g., stabilization of a discernible symptom), physiologically, (e.g., stabilization of a physical parameter) or both. In yet other embodiments, "treating" or "treatment" refers to preventing or to delaying the onset of the disease, disorder, or condition.

"Therapeutically effective amount" or "effective amount" means the amount of a composition, compound, therapy, or course of treatment that, when administered to a subject for treating a disease, disorder, or condition, is sufficient to effect such treatment for the disease, disorder, or condition. The "therapeutically effective amount" will vary depending on the composition, the compound, the therapy, the course of treatment, the disease, disorder, or condition, and its severity and the age, weight, etc., of the subject to be treated.

When the biguanide compounds described herein include one or more chiral centers, the stereochemistry of such chiral centers can independently be in the R or S configuration, or a mixture of the two. The chiral centers can be further designated as R or S or R,S or d,D, l,L or d,l, D,L. Correspondingly, the biguanide compounds of the invention, if they can be present in optically active form, can actually be present in the form of a racemic mixture of enantiomers, or in the form of either of the separate enantiomers in substantially isolated and purified form, or as a mixture comprising any relative proportions of the enantiomers.

When the biguanide compounds described herein contain two or more chiral centers then diastereomers are possible. Such diastereomers may be present as pure diastereomeric enantiomers, pure racemic mixtures of diastereomeric enantiomers, mixtures of diastereomers which may be racemic or may have optical activity in their own right due to complex permutations of enantiomeric diastereomers in the balance of the mixtures.

When the biguanide compounds of the invention, if they can be present in geometrically isomeric forms around, for example, the guanide bond, then they can actually be present in the form of a mixture of geometric isomers comprising any relative proportions of the isomers, or in some cases in the form of either of the separate geometric isomers in substantially isolated and purified form.

When the biguanide compounds described herein include one or more isolated or linearly conjugated double bonds, the geometry around such double bonds can be independently a cis/trans, E/Z mixture or an E or Z geometric isomer thereof.

"Alkyl" means a straight or branched chain, saturated monovalent hydrocarbon radical. By way of example, the hydrocarbon chain may have from one to twenty carbons, one to sixteen carbons, one to fourteen carbons, one to twelve carbons, one to ten carbons, one to eight carbons, one to six carbons, one to four carbons, etc. "Lower alkyl" may refer to alkyls having, e.g., one to six carbons, one to four carbons, etc. In certain examples, an straight chain alkyl may have from one to six carbon atoms and a branched alkyl three to six carbon atoms, e.g., methyl, ethyl, propyl, 2-propyl, butyl (including all isomeric forms), pentyl (including all isomeric forms), and the like. "Me" means methyl, "Et" means ethyl, and "iPr" means isopropyl.

"Aryl" means a monovalent monocyclic or bicyclic aromatic hydrocarbon radical, e.g., having from of 6 to 20 or 6 to 10 ring atoms e.g., phenyl or naphthyl.

"Alkylaryl" means a (alkylene)-R radical where R is aryl as defined above.

"Cycloalkyl" means a cyclic saturated or partially saturated monovalent hydrocarbon radical (or an alicyclic radical). By way of example, the cycloalkyl may have from three to twenty carbon atoms, from three to sixteen carbon atoms, from three to fourteen carbon atoms, from three to twelve carbon atoms, from three to ten carbon atoms, from three to eight carbon atoms, from three to six carbon atoms, etc., wherein one or two carbon atoms may be replaced by an oxo group, e.g., admantanyl, cyclopropyl, cyclobutyl, cyclopentyl, cyclohexyl, cyclohexenyl, indanyl and the like.

"Alkylcycloalkyl" means a (alkylene)-R radical where R is cycloalkyl as defined above; e.g., cyclopropylmethyl, cyclobutylmethyl, cyclopentylethyl, or cyclohexylmethyl, and the like.

"Heterocyclyl" or "heterocycloalkyl" means a saturated or unsaturated monovalent monocyclic group, in which one or two ring atoms are heteroatom selected from N, O, or S, the remaining ring atoms being C. The heterocyclyl ring is optionally fused to a (one) aryl or heteroaryl ring as defined herein. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Alkylheterocycloalkyl" means a -(alkylene)-R radical where R is heterocyclyl ring as defined above e.g., tetraydrofuranylmethyl, piperazinylmethyl, morpholinylethyl, and the like.

"Heteroaryl" means a monovalent monocyclic or bicyclic aromatic radical, where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, diazolyl, pyrazolyl, triazolyl, benzothiazolyl, benzoxazolyl, quinolinyl, isoquinolinyl, pyridinyl, pyrimidinyl, pyrazinyl, pyridazinyl, tetrazolyl, and the like.

"Oxo" or "carbonyl" means =(O) group or C=O group, respectively.

The term "substituted" means that the referenced group is substituted with one or more additional group(s) individually and independently selected from groups described herein. In some embodiments, an optional substituent is selected from oxo, halogen, —CN, —NH$_2$, —OH, —NH (CH$_3$), —N(CH$_3$)$_2$, alkyl (including straight chain, branched and/or unsaturated alkyl), substituted or unsubstituted cycloalkyl, substituted or unsubstituted heterocycloalkyl, fluoroalkyl, substituted or unsubstituted heteroalkyl, substituted or unsubstituted alkoxy, fluoroalkoxy, —S-alkyl, —S(O)$_2$-alkyl, —CONH ((substituted or unsubstituted alkyl) or (substituted or unsubstituted phenyl)), —CON(H or alkyl)$_2$, —OCON (substituted or unsubstituted alkyl)$_2$, —NHCONH ((substituted or unsubstituted alkyl) or (substituted or unsubstituted phenyl)), —NHCOalkyl, —N(substituted or unsubstituted alkyl)CO (substituted or unsubstituted alkyl), —NHCOO (substituted or unsubstituted —C(OH)(substituted or unsubstituted alkyl)$_2$, and —C(NH$_2$)(substituted or unsubstituted alkyl)$_2$. In some embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(O)$_2$—CH$_3$, —CONH$_2$, —CONHCH$_3$, —NHCONHCH$_3$, —COCH$_3$, —COOH and the like. In some embodiments, substituted groups are substituted with one, two or three of the preceding groups. In some embodiments, substituted groups are substituted with one or two of the preceding groups. In some embodiments, substituted groups are substituted with one of the preceding groups. Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

In some embodiments, a biguanide compound of the disclosure is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the biguanide compound described herein are reacted with an organic base, such as, but not limited to, ethanolamine, diethanolamine, triethanolamine, tromethamine, N-methylglucamine, dicyclohexylamine, tris(hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd Revised Ed., Springer-Verlag, New York, N.Y., 1984 and 1993, and Stewart and Young, "Solid Phase Peptide Synthesis," 2nd Ed., Pierce Chemical Co., Rockford, Ill., 1984, both of which are incorporated herein by reference.

Amino acids and amino acid analogs can be purchased commercially (Sigma Chemical Co.; Advanced Chemtech) or synthesized using methods known in the art.

In the scope of the embodiments, the biguanide compounds described herein include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including but not limited to single enantiomers and enantiomeric di astereomers, meso compounds, stereoisomers, racemic mixtures and diasteroisomeric mixtures. Biguanide compounds described herein having one or more double bonds include cis/trans isomers, E/Z isomers and geometric isomers. Biguanide compounds described herein can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

In some embodiments, the biguanide compounds described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

As noted above, in some embodiments the biguanide compounds described herein possess one or more stereocenters and each center exists independently in either the R or S configuration. The biguanide compounds presented herein include all diastereomeric, enantiomeric, and epimeric forms as well as the appropriate mixtures thereof.

In some embodiments, sites on the biguanide compounds disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the biguanide compounds described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements. Throughout the specification, groups and substituents thereof can be chosen by one skilled in the field to provide stable moieties and compounds.

Biguanides

The compositions and methods disclosed herein relate to metformin and other biguanides. By way of background, metformin is one of the simplest structural variants of a class of compounds known as the biguanides. From a structural perspective metformin resembles a pharmacophore or fragment of a larger biologically active chemical structure.

In one embodiment, the biguanide compounds of the subject invention include the following:

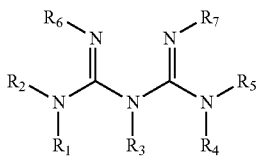

I wherein:

R$_1$, R$_2$, R$_3$, R$_4$, R$_5$, R$_6$, and R$_7$ are independently selected from:

H, OH,

O-Rx, wherein Rx is alkyl, cycloalkyl, alkylcycloalkyl, acyl, ester, thioester;

optionally substituted alkyl (e.g., a C$_1$ to C$_{12}$ straight chain or branched chain alkyl optionally substituted with oxygen, silicon, sulphur or optionally substituted with OH, O-alkyl, SH, S-alkyl, NH$_2$, NH-alkyl); cycloalkyl (e.g., C$_3$ to C$_7$ cycloalkyl); alkylcycloalkyl (e.g., C$_4$ to C$_{12}$ alkylcycloalkyl); heterocycloalkyl (e.g., where the heterocycle comprises one or two hetero atoms selected from O, S, or N, including a C$_2$ to C$_6$ heterocycloalkyl); alkylheterocycloalkyl (e.g., where the heterocycle comprises one or two hetero atoms selected from O, S, or N, including a C$_3$ to C$_{11}$ alkylheterocycloalkyl, and including wherein when N is present in the heterocyclic ring, the nitrogen atom may be in the form of an amide, carbamate or urea); optionally substituted alkenyl (e.g., C$_1$ to C$_{12}$ straight chain or branched chain alkenyl optionally substituted with oxygen, silicon, sulphur or optionally substituted with OH, O-alkyl, SH, S-alkyl, NH$_2$, NH-alkyl); optionally substituted alkynyl (e.g., C$_1$ to C$_{12}$ straight chain or branched chain alkynyl optionally substituted with oxygen, silicon, sulphur or optionally substituted with OH, O-alkyl, SH, S-alkyl, NH$_2$, NH-alkyl);

optionally substituted aryl (e.g., phenyl, substituted phenyl, naphthyl, substituted naphthyl); optionally substituted alkyl aryl (e.g., alkylphenyl, alkylsubstituted phenyl, alkylnaphthyl, alkyl substituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and or R$_6$ and R$_7$ may join to form a bond, together forming a ring including the nitrogen atoms to which they are attached;

or R$_1$ and R$_2$ may together form a 3 to 8 membered heterocyclic ring, including the nitrogen atoms to which they are attached;

or R$_4$ and R$_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

In certain embodiments, O-Rx may be selected from: O—C$_1$ to C$_8$ straight chain or branched chain alkyl; O—C$_3$ to C$_7$ cycloalkyl; O—C$_4$ to C$_8$ alkylcycloalkyl; O-acyl; O-esters; and O-thioesters.

In other embodiments, optional substitutions may include, e.g., OH, O-alkyl, SH, S-alkyl, NH$_2$, NH-alkyl. Further, an alkyl, alkenyl, alkynyl, etc. may be substituted with an oxygen, silicon, sulphur, etc. to form a heteroalkyl, heteroalkenyl, heteroalkynyl, etc.

In certain embodiments, each of: R$_3$, R$_6$, and R$_7$, or R$_3$, R$_4$, R$_5$, and R$_7$, or R$_3$, R$_4$, R$_5$, and R$_7$, or R$_3$, R$_4$, R$_5$, R$_6$ and R$_7$, or R$_2$, R$_3$, R$_4$, R$_5$, R$_6$ and R$_7$ are independently selected from:

H, methyl, ethyl, propyl or isopropyl;

and each of the remaining substituent groups: R$_1$, R$_2$, R$_4$, and R$_5$, or R$_1$, R$_2$, and R$_6$, or R$_1$, R$_2$, and R$_6$, or R$_1$ and R$_2$, or R$_1$, respectively, are independently selected from:

H; optionally substituted alkyl (e.g., C$_1$ to C$_{12}$ straight chain or branched chain alkyl optionally hetero substituted with oxygen, silicon, sulphur or optionally substituted with OH, O-alkyl, SH, S-alkyl, NH$_2$, NH-alkyl); optionally substituted alkenyl (e.g., C$_1$ to C$_{12}$ straight chain or branched chain alkenyl optionally hetero substituted with oxygen, silicon, sulphur or optionally substituted with OH, O-alkyl, SH, S-alkyl, NH$_2$, NH-alkyl); optionally substituted alkynyl (e.g., C$_1$ to C$_{12}$ straight chain or branched chain alkynyl optionally hetero substituted with oxygen, silicon, sulphur or optionally substituted with OH, O-alkyl, SH, S-alkyl, NH$_2$, NH-alkyl); cycloalkyl (e.g., C$_3$ to C$_7$ cycloalkyl); alkylcycloalkyl (e.g., C$_4$ to C$_{12}$ alkylcycloalkyl); heterocycloalkyl (e.g., where the heterocycle comprises one or two hetero atoms selected from O, S, or N, including C$_2$ to C$_6$ heterocycloalkyl); alkylheterocycloalkyl (e.g., where the heterocycle comprises one or two hetero atoms selected from O, S, or N, including C$_3$ to C$_{11}$ alkylheterocycloalkyl, and including wherein when N is present in the heterocyclic ring, the nitrogen atom may be in the form of an amide, carbamate or urea); aryl (e.g., phenyl, substituted phenyl, naphthyl, substituted naphthyl); alkylaryl (e.g., alkylphenyl, alkylsubstituted phenyl, alkylnaphthyl, alkylsubstituted naphthyl); heteroaryl (e.g., pyridyl, furanyl, thiophenyl, pyrrollyl, oxazolyl, isoxazolyl, thiazolyl, diazolyl, pyrazolyl, triazolyl all of which are optionally substituted); alkylheteroaryl;

or R$_1$ and R$_2$ may together form a 3 to 8 membered heterocyclic ring, including the nitrogen atoms to which they are attached;

or R$_4$ and R$_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

Exemplary compounds and substituents of R$_1$, R$_2$, R$_3$, R$_4$, R$_5$, R$_6$, and R$_7$ of Formula I are shown below. Additional combinations of selections of substituents of R$_1$, R$_2$, R$_3$, R$_4$, R$_5$, R$_6$, and R$_7$ are envisioned and disclosed in co-pending U.S. patent application Ser. No. 13/547,022, the disclosure of which is expressly incorporated by reference herein.

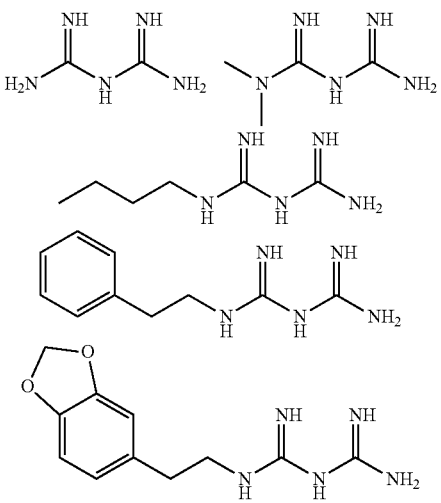

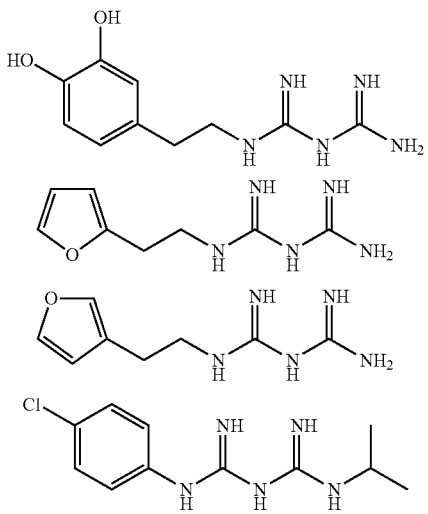

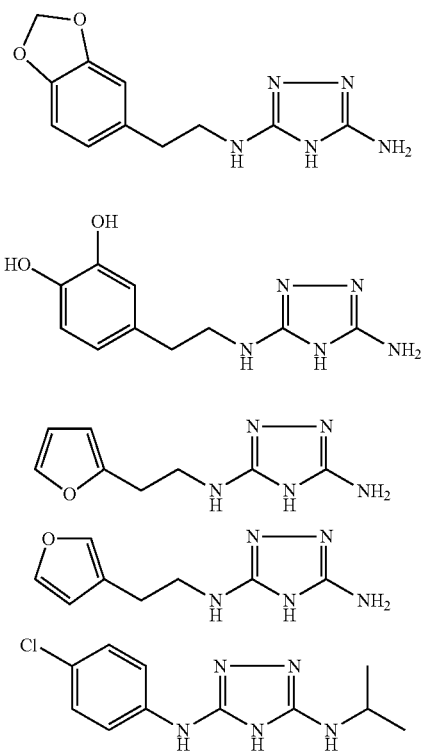

In certain embodiments, the biguanide compounds of Formula I may include an asymmetric center or centers, and may be in the form of a composition of a racemic mixture, a diastereoisomeric mixture, a single enantiomer, an enantiomeric diastereomer, a meso compound, a pure epimer, or a mixture of epimers thereof, etc. Further, the biguanide compounds may have one or more double bonds, and may be in a form of a cis/trans, E/Z mixture or an E or Z geometric isomer thereof.

The biguanide compounds of Formula I may also be prepared as a salt form, e.g., pharmaceutically acceptable salts, including suitable acid forms, e.g., salt forms selected from hydrochloride, hydrobromide, acetate, propionate, butyrate, sulphate, hydrogen sulphate, sulphite, carbonate, hydrogen carbonate, phosphate, phosphinate, oxalate, hemi-oxalate, malonate, hemi-malonate, fumarate, hemi-fumarate, maleate, hemi-maleate, citrate, hemi-citrate, tartrate, hemi-tartrate, aspartate, glutamate, etc.

Alternative embodiments of biguanide compounds specifically contemplated for use in the subject invention include the related heterocyclic compounds described in co-pending U.S. patent application Ser. No. 13/547,022, the disclosure of which is expressly incorporated herein by reference. The phrase "biguanide compound" as used herein includes these related heterocyclic compounds, exemplary embodiments of which include the following:

Triazoles:

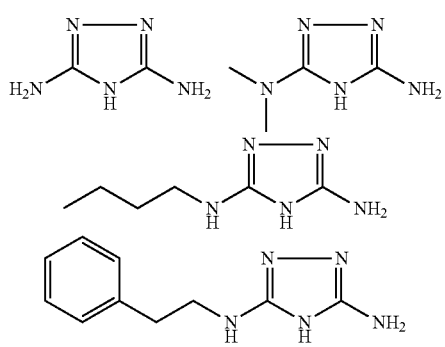

Triazines:

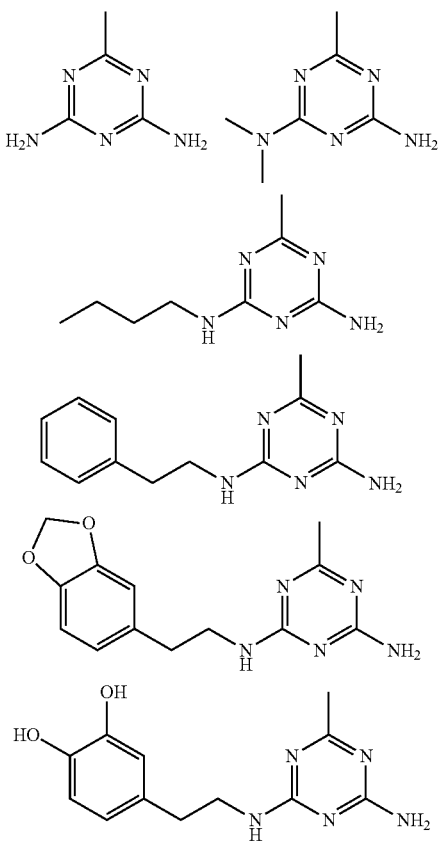

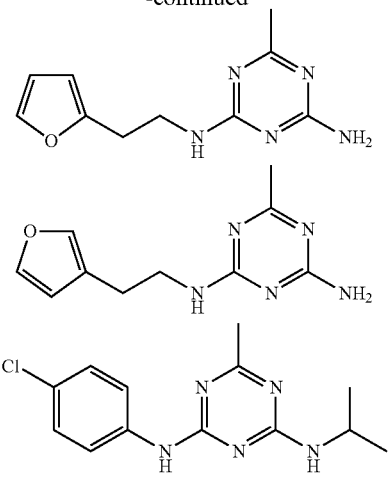
Dihydrotriazines:
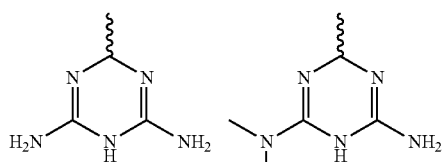
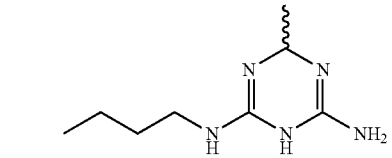
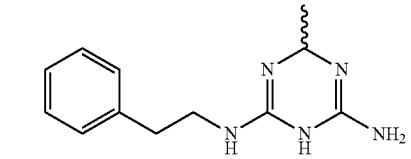
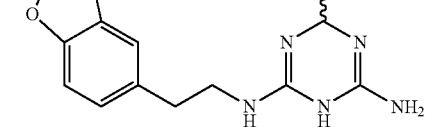
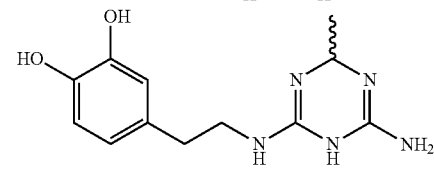
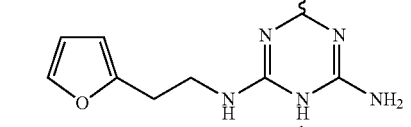
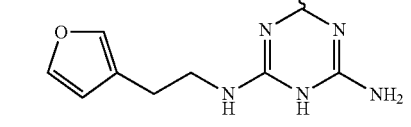
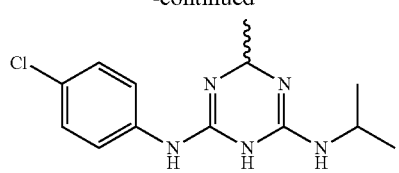
7-ring cyclic biguanides:
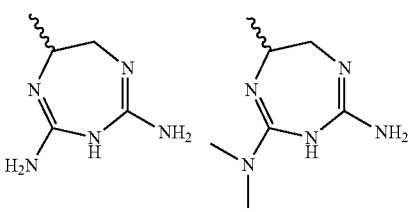
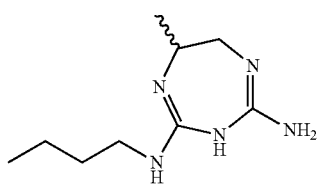
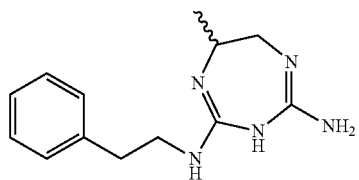
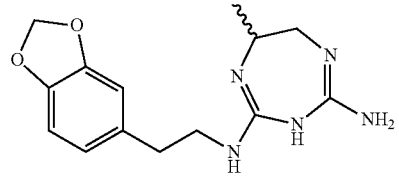
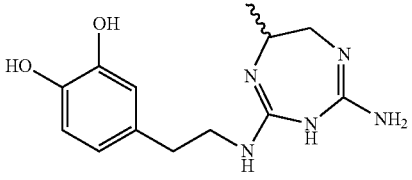
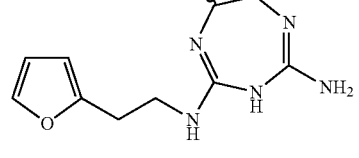
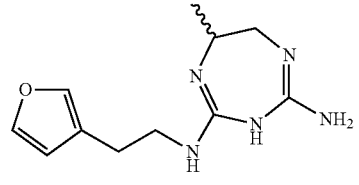

-continued

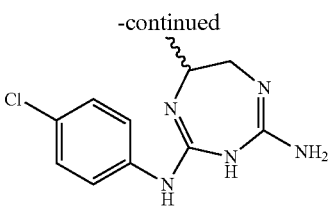

In one embodiment, the compounds of the disclosure may be prepared as a three component salt form including the components A, B, and C wherein:
A is the protonated form of a natural or unnatural amino acid;
B is the dianion of an acid; and
C is the protonated form of a Compound of Formula T.

In certain aspects, stoichiometric amounts of A, B, and C may be included wherein:
A is the protonated form of a natural amino acid selected from alanine, aspartic acid, asparagine, arginine, glycine, glutamine, glutamic acid lysine, phenylalanine, tyrosine, serine, threonine, tryptophan, leucine, isoleucine, histidine, methionine, proline, cysteine, or cystine;
B is the dianion of an acid selected from oxalic, malonic, citric, maleic, fumaric, tartaric, aspartic, glutamic acids and the like; and
C is the protonated form of a compound of Formula I.

Contraindications for Biguanide Compounds, Including Metformin

Since systemic biguanides, including metformin are reported to be substantially excreted by the kidney, the risk of the biguanide compound accumulation and lactic acidosis increases with the degree of impairment of renal function. Other contraindications for biguanide compounds such as metformin include impaired lactate clearance, and a hypoxic condition. Accordingly, patients having these contraindications are not currently treatable with conventional biguanide compounds.

However, as demonstrated herein, the therapeutic efficacy of metformin and other biguanide compounds docs not require an increase in the systemic level of the metformin that presents an increased risk of lactic acidosis. As such, the risk of metformin accumulation and lactic acidosis is dramatically lower, and the methods provided herein can therefore be used to treat a condition in a patient in need thereof, even where the patient has a contraindication for metformin. For example, the methods provided herein may be used to treat a patient in need thereof, wherein the patient has a hypoxic condition (e.g., respiratory failure and/or heart failure), impaired lactate clearance (e.g., due to liver failure), impaired metformin clearance, and/or renal impairment, which may be moderate, severe, or endstage impairment, and may be the result of chronic kidney disease.

Metabolic Disorders

The compositions and methods of the present invention find advantageous use in the treatment and/or prophylaxis of metabolic disorders, including being overweight, obesity, prediabetes, Polycystic Ovary Syndrome, dislipidemia or disorders of lipid metabolism, as well as hyperglycemic conditions, such as insulin-dependent (type 1) or -independent (type 2) diabetes, as well as physiological conditions or disorders associated with or that result from the hyperglycemic condition. Thus, hyperglycemic conditions treatable by a method of the invention also include a histopathological change associated with chronic or acute hyperglycemia (e.g., diabetes). Particular examples include degeneration of pancreas (β-cell destruction), kidney tubule calcification, degeneration of liver, eye damage (diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension and obesity.

As used herein, the term "hyperglycemic" or "hyperglycemia," when used in reference to a condition of a patient, means a transient or chronic abnormally high level of glucose present in the blood of a patient. The condition can be caused by a delay in glucose metabolism or absorption such that the patient exhibits glucose intolerance or a state of elevated glucose not typically found in normal patients (e.g., in glucose-intolerant subdiabetic patients at risk of developing diabetes, or in diabetic patients). Fasting plasma glucose (FPG) levels for normoglycemia are less than about 110 mg/dl, for impaired glucose metabolism, between about 110 and 126 mg/dl, and for diabetics greater than about 126 mg/dl.

Metabolic disorders also include obesity or an undesirable body mass. Leptin, cholecystokinin, PYY and GLP-1 decrease hunger, increase energy expenditure, induce weight loss or provide normal glucose homeostasis. Thus, in various embodiments, a method of the invention for treating obesity or an undesirable body mass, or hyperglycemia, involves the local administration of metformin to activate enteroendocrine cell production of cholecystokinin, oxyntomodulin, GIP, GLP-2, PYY or GLP-1. Disorders treatable also include those typically associated with obesity, for example, abnormally elevated serum/plasma LDL, VLDL, triglycerides, cholesterol, plaque formation leading to narrowing or blockage of blood vessels, increased risk of hypertension/stroke, coronary heart disease, etc.

Synthesis of the Compounds

Compounds described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference in their entirety). General methods for the preparation of the compounds as disclosed herein may be derived from known reactions in the field, and the reactions may be modified by the use of appropriate reagents and conditions, as would be recognized by the skilled person, for the introduction of the various moieties found in the formulae as provided herein.

Additional biguanide synthesis methods and schemes for the compounds described herein can be found in U.S. application Ser. No. 12/593,479 (published as U.S. 2010/0130498); U.S. application Ser. No. 12/593,398 (published as U.S. 2010/0184796); U.S. Pat. No. 7,829,299; U.S. application Ser. No. 11/578,013 (published as U.S. 2010/0056621); U.S. Pat. No. 7,416,867; U.S. application Ser. No. 11/455,693 (published as U.S. 2007/0037212); U.S. application Ser. No. 13/059,730 (published as U.S. 2011/0143376), U.S. application Ser. No. 12/996,670 (published as U.S. 2011/0311991), U.S. Pat. No. 7,811,788; U.S. application Ser. No. 11/182,942 (published as U.S. 2006/0019346); U.S. application Ser. No. 12/993,542 (published as U.S. 2011/0086138), U.S. application Ser. No. 12/373,235 (published as U.S. 2010/0055209); International Application Ser. No. PCT/IL2007/000454 (published as WO 2007/116404); U.S. application Ser. No. 10/472,056 (published as U.S. 2004/0138189); U.S. Pat. No. 5,891,919; U.S. Pat. No. 6,376,657; U.S. application Ser. No. 11/554,982 (published as U.S. 2007/0104805); U.S. application Ser. No. 11/926,745 (published as U.S. 2008/0108604); International Application Ser. No. PCT/CA2009/001688 (published as WO 2010/060198); U.S. application Ser. No. 12/735,557 (published as U.S. 2010/0330205); International Application Ser. No. PCT/CA2007/001066 (published as WO 2008/000063); U.S. application Ser. No. 11/438,204 (published as U.S. 2006/0269617); U.S. application Ser. No. 10/563,713 (published as U.S. 2006/0172020); U.S. application Ser. No. 10/902,352 (published as U.S. 2006/0024335); U.S. application Ser. No. 10/538,038 (published as U.S. 2006/0275765), U.S. application Ser. No. 11/555,617 (published as U.S. 2008/0187936); U.S. application Ser. No. 12/739,264 (published as U.S. 2010/0316736); U.S. application Ser. No. 12/215,609 (published as U.S. 2009/0042813); U.S. application Ser. No. 11/893,088 (published as U.S. 2008/0050499); U.S. Pat. No. 7,807,204; U.S. application Ser. No. 11/811,166 (published as U.S. 2008/0003268); U.S. Pat. No. 6,376,657; International Application Ser. No. PCT/US2011/041183 (published as WO 2011/163183); International Application Ser. No. PCT/EP2011/059814 (published as WO 2011/157692); U.S. application Ser. No. 12/790,292 (published as U.S. 2011/0293753); International Application Ser. No. PCT/JP2009/071700 (published as WO 2010/076879); U.S. application Ser. No. 13/032,530 (published as U.S. 2011/0217394); International Application Ser. No. PCT/EP2011/000110 (published as WO 2011/085979); International Application Ser. No. PCT/US2010/058467 (published as WO 2011/068814); U.S. application Ser. No. 13/060,996 (published as U.S. 2011/0152361); U.S. application Ser. No. 12/09,253 (published as U.S. 2011/0124609); U.S. application Ser. No. 12/687,962 (published as U.S. 2011/0119499); and International Application Ser. No. PCT/EP2010/004623 (published as WO 2011/012298); each of which are incorporated by reference in their entirety.

Administration and Methods

The biguanide compounds of the disclosure, including analogs, salts, solvates, polymorphs, hydrates, N-oxides, and prodrugs of such compounds, may be administered to a subject in need thereof to treat various metabolic disorders, including obesity, dislipidemia or other disorders of lipid metabolism as well as hyperglycemic conditions and histopathological diseases associated with hyperglycemia, including type II diabetes. Particularly in view of the surprising and unexpected decoupling of systemic bioavailability and therapeutic efficacy achieved herein, and consequent improvement in toxicity and safety, the effective use of such compounds for prophylaxis and prevention of such diseases and disorders, as well as use for more general weight loss purposes, is also explicitly contemplated herein.

In preferred embodiments, the compound is metformin. Prior formulations of metformin are reported to have an average bioavailability of 30% to 60% while many comparable small molecules have bioavailability of greater than 60%. See, e.g., Tucker et al., "Metformin kinetics in healthy subjects and in patients with diabetes mellitus" Br. J. Clin. Pharmacol. 1981, 12(2) 235-246. Notably, metformin administration increases plasma concentrations of GLP-1 in normal, diabetic and DPP-IV-deficient rodents, as well as in humans with and without type II diabetes, but has been reported to do so indirectly and independent of a direct impact on intestinal L cells. Mulherin et al., supra.

As demonstrated herein, however, and contrary to the well-established convention in the art, enteroendocrine activation by metformin may be triggered by luminal signals on the epithelial aspect of the gut, and therefore increased systemic bioavailability of metformin is actually unnecessary after oral ingestion in order to stimulate the release of gastrointestinal hormones such as GLP-1. Accordingly, the effective treatment of otherwise contraindicated patients is now made possible by administering compositions comprising biguanide compounds (including analogs, salts, solvates, polymorphs, hydrates, N-oxides, and prodrugs thereof) adapted to minimize the systemic bioavailability of the compound. In preferred embodiments, the subject compositions and methods are formulated so as to minimize and preferably avoid an initial release in the stomach and/or proximal small intestine (areas with the greatest absorption) in order to reduce systemic bioavailability upon oral administration.

Delivery to Specific Intestinal Locations

The embodiments described herein provide a treatment method comprising administering a delayed-release composition comprising a biguanide compound (including any analogs, salts, solvates, polymorphs, hydrates, N-oxides, or prodrugs thereof) formulated to be delivered to one or more locations of the small intestine and/or lower intestine, and preferably distal small intestine, in order to minimize systemic bioavailability by avoiding absorption in the stomach and proximal small intestine and corresponding rapid increase in $C_{max}$.

The biguanide compounds are targeted beyond the stomach to one or more regions of the small intestine, and are preferably targeted downstream or distal of the duodenum. In preferred embodiments, the compounds are delivered to the jejunum, ileum, caecum and colon, or a combination thereof. In preferred embodiments, the compounds are delivered to the jejunum, ileum and caecum, or a combination thereof. In preferred embodiments, the compounds are preferentially targeted to the ileum. In additional embodiments, the compound is delivered downstream or distal of the jejunum, or solely to the lower intestine.

In yet other embodiments, the biguanide compound (including an analog, salt, solvate, polymorph, hydrate, N-oxide, or prodrug thereof) is delivered to one or more regions of the upper intestine and one or more regions of the lower intestine. For example, the compound can be delivered to the duodenum and the colon. In another non-limiting example, the compound can be delivered to the duodenum, jejunum, ileum and colon.

The administration of biguanides such as metformin to the preferred regions or locations of the intestine may be achieved by any known method. In preferred embodiments, the biguanide compound is formulated in a delayed-release composition for oral delivery that delivers the compound to the targeted regions or locations of the intestine. When delivery of the biguanide compound is targeted to two or more regions of the gastrointestinal tract, the compound may be delivered in any proportion and manner.

Minimizing Systemic Exposure

As described above, the methods disclosed herein minimize the systemic bioavailability of the biguanide compound in contraindicated patients. In some embodiments, the biguanide compounds have reduced average systemic bioavailability. Reduced average systemic bioavailabity, in some embodiments, is lower average systemic bioavailability as compared to an immediate release or extended release formulation having an equivalent amount of the biguanide compound. In other embodiments, reduced average systemic bioavailability is when the average systemic bioavailability is less than 30%, less than 25%, less than 15%, less than 10% and less than 5% as compared to an immediate or extended release formulation having an equivalent amount of the biguanide compound. In certain instances, the average systemic bioavailability is less than 15%.

In some embodiments, the subject methods minimize the mean plasma $C_{max}$ and/or mean AUC levels of the biguanide compound in contraindicated patients. In some embodiments, the administration methods result in minimal plasma absorption, mean $C_{max}$ and/or mean AUC levels of the biguanide compounds in the patient. It other embodiments, the mean plasma $C_{max}$, and/or mean AUC levels of the biguanide compound are considered sub-therapeutic for the described compositions as compared to the reported $C_{max}$ and/or AUC levels of conventional immediate-release and extended-release formulations having identical amounts of metformin. For example, negligible or sub-therapeutic metformin plasma $C_{max}$ and/or AUC levels include 75%, 60%, 50%, 40% and 30% of reported $C_{max}$ and/or AUC levels of known metformin formulations (e.g., GLUMETZA®, GLUCOPHAGE®, GLUCOPHAGE® XR, RIOMET®, FORTAMET®, OBIMET®, GLUFORMIN®, DIANBEN®, DIABEX®, DIAFORMIN®, Metformin Metformin SR®, and the like).

In specific embodiments, the inventive compositions and methods directed to metformin produce a $C_{max}$ that is no more than 75% or 85%, preferably no more than 50% or 60%, more preferably no more than 25% or 30% or 40% of the same dose of an immediate release metformin formulation (e.g. GLUCOPHAGE®) following oral ingestion. In other embodiments, the inventive methods provide a $C_{max}$ that is no more than 3×, more preferably no more than 2.5× or 2×, still more preferably no more than 1.8× or 1.5× the initial trough plasma concentration 10-12 hours after the last oral ingestion of metformin. In other embodiments, the inventive compositions and methods provide a mean plasma AUC over the dosing interval that is no more than 75% or 80%, preferably no more than 50% or 60%, more preferably no more than 25%, 30% or 40% of the same dose of an immediate release formulation (e.g. GLUCOPHAGE®) following oral ingestion.

Accordingly, in specific embodiments, administration of the subject delayed-release formulation minimizes the mean plasma AUC, the mean plasma $C_{max}$ and/or the circulating plasma concentration of the biguanide compound in contraindicated patients compared to an identical protocol administering an IR or XR formulation having the same amount of the biguanide compound. In one embodiment, the mean plasma $AUC_{O3}$ of the biguanide compound resulting from administration is less than about 15,000 ng*h/mL or 14,000 ng*h/mL, preferably less than about 12,000 ng*h/mL, 11,000 ng*h/mL or 10,000 ng*h/mL, more preferably less than about 9,000 ng*h/mL, 8,000 ng*h/mL or 7,000 ng*h/mL In one embodiment, the resulting mean plasma $C_{max}$ of the biguanide compound is less than about 1000 ng/mL, preferably less than about 900 ng/mL or 800 ng/mL, more preferably less than about 700 ng/mL, 600 ng/mL or 500 ng/mL In one embodiment, the resulting circulating plasma concentration of the biguanide compound is below about 5 µg/ml or 4 µg/ml, preferably below about 3 µg/ml or 2.5 µg/ml, more preferably below about 2 µg/ml, 1 µg/ml, 0.5 µg/ml, or 0.25 µg/ml in the patient. In preferred embodiments, the biguanide compound is metformin, the IR composition is Glucophage® and the XR composition is Glucophage® XR.

Formulations

To limit its systemic bioavailability, the compositions comprising the biguanide compound are adapted for delayed release so as to minimize plasma absorption. The delivery of biguanide compounds such as metformin to the enteroendocrine cells is via any known method including, e.g., oral, rectal, nasogastric tube, parenterally injection such as intraluminal intestinal injection. In preferred embodiments, oral dosage forms are administered. Oral delivery of biguanide compounds is described in the delayed release formulations section and include timed release systems, enteric coatings and pH dependent systems, and the like. In some embodiments, the compositions comprising the compounds described herein utilize a multicomponent system where the biguanide compound is delivered to several places in the gastrointestinal tract such as the duodenum, jejunum, ileum, lower intestine or combinations thereof following administration. For example, a delayed-release formulation comprising the biguanide compound can deliver to the lower intestine by use of timed or delayed (enteric) release components. Multicomponent systems of such compounds can be in unitary dosage forms such as bi- or tri- or multiple-layer tablets or multi-particulate forms such as encapsulated micro-tablets, granules or as separate dosage forms, e.g., separate tablets taken together or at a periodic interval.

In some embodiments, the delayed-release formulation releases the biguanide compound after onset of a desired pH, due to the enteric coating. pHs contemplated include about pH 5.0 or about pH 5.5, more preferably about pH 6.0, about pH 6.5 and about pH 7.0. After onset of a desired pH, the compound begins release. Such compositions may release the biguanide compound in about 15 minutes, about 20 minutes, about 25 minutes or about 30 minutes after the onset of the desired pH, and/or may have timed, extended or slow release aspects that release the biguanide compound over the course of a longer time period such as about 1 hour, about 2 hours, about 3 hours, about 4 hours, about 5 hours, about 6 hours, about 7 hours or about 8 hours. Exemplary two component delivery system can be, in some embodiments, a bilayer tablet. Three, four and additional components are contemplated within the embodiments.

For delayed-release formulations comprising the biguanide compound, dosages of the compound can range from about 1 mg to about 2000 mg, about 10 mg to about 1500 mg, about 50 mg to about 1000 mg or about 100 mg or about 500 mg per day. In some instances, the dosage of the compound is about 2000 mg, about 1500 about 1000 mg, about 800 mg, about 600 mg, about 500 mg, about 400 mg, about 300 mg, about 250 mg, about 200 mg, about 150 mg, about 100 mg, about 75 mg, about 50 mg, about 25 mg, about 10 mg or about 1 mg per day. In some embodiments, the dosage of the compound is less than 400 mg. In some embodiments, the dosage of the compound is 250 mg.

Salts of biguanide compound include, but are not limited to, hydrochloride, phosphate, sulfate, hydrobromide, salicylate, maleate, benzoate, succinnate, ethanesulfonate, fumarate, glycolate, pamoate, oratate, acetate, isobutyrate, acetylsalicylate, nicotinic acid, adamantoate, zinc chlorophylin, carboxylic acid, benzoic acid, dichloroacetic acid, theophylin-7-acetate, clofibrate, tartate, oxalate, tannate and hydroxyl acid salts. In preferred embodiment, the salt is metformin hydrochloride.

The biguanide compounds of the subject invention can be advantageously administered or combined with additional therapeutic agents, such as anti-obesity and/or anti-diabetic agents described herein. Notable agents for combinations with the metformin compositions described herein include DPP-IV inhibitors (e.g., sitagliptin, saxagliptin, berberine, vildagliptin, linagliptin, alogliptin, and the like), SGLT-2 and/or SGLT-1 inhibitors (e.g., dapafloglizin, canafloglizin, LX4211), agonists of GPR40, GPR120, GPR119, GPR41, GPR43, etc., thiazolidinediones (e.g., pioglitazone, rivoglitazone, rosiglitazone, troglitazone, and the like), sulfonylureas (e.g., glipzide, glibenclamide (glyburide), gliquidone, glyclopyramide, glimepiride, gliclazide, acetohexamide, carbutamide, chlorpropamide, tolbutamide, tolazamide, and the like), Dual PPAR agonists (e.g., aleglitazar, muraglitazar, tesaglitazar, and the like), lipid-lowering agents (e.g., statins), and anti-hypertensive agents.

Formulations for the compositions provided herein include those suitable for oral or rectal administration, and administration although the most suitable route can depend upon for example the condition and disorder of the recipient. The formulations can conveniently be presented in unit dosage form and can be prepared by any of the methods well known in the art of pharmacy. All methods include the step of bringing into association the active ingredient with the carrier which constitutes one or more accessory ingredients.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Composition preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

It should be understood that in addition to the ingredients particularly mentioned above, the compounds and compositions described herein can include other agents conventional in the art having regard to the type of formulation in question, for example those suitable for oral administration can include flavoring agents.

The compositions described herein can also contain the biguanide compound in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents selected from, by way of non-limiting example, sweetening agents, flavoring agents, coloring agents and preserving agents in order to provide pharmaceutically elegant and palatable preparations.

Delayed Release Formulations

Many strategies can be pursued to obtain delayed release in which the location of the release is controlled so as to minimize systemic absorption. For example, delayed release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles and liposomes. The release mechanism can be controlled such that the biguanide compounds are released at period intervals or the location of the release is controlled, the release of combined agents can be simultaneous, or a delayed release of the biguanide compound in a combination can be affected when the early release of another combined therapeutic one is preferred over the other. Different delivery systems described herein can also be combined to release at an onset of multiple period intervals (e.g., about 30 minutes, about 120 minutes, about 180 minutes and about 240 minutes after oral administration) or at different locations (e.g., release in the lower intestine, upper intestine, the jejunum, ileum, caecum, colon, and/or rectum) or a combination thereof. For example, a pH dependent system can be combined with a timed release system or any other system described herein to achieve a desired release profile.

In certain embodiments, the biguanide compounds are provided in the form of a delayed release formulation coupled with an extended release component of the biguanide compound and/or an additional therapeutic agent in a unitary dosage form. The extended release component can be formulated by any known method such as a layer that envelops a portion of the delayed release component or the like. Exemplary ratios of extended release of an additional therapeutic agent to delayed release of a biguanide compound are about 10% XR to about 90% DR, about 15% XR to about 85% DR, about 20% XR to about 80% DR, about 25% XR to about 75% DR, about 30% XR to about 70% DR, about 35% XR to about 65% DR, about 40% XR to about 60% DR, about 45% XR to about 55% DR, or about 50% XR to about 50% DR. In certain embodiments, the extended release of an active agent to modified release of an active agent is about 25% XR to about 75% DR. In certain embodiments, the extended release of an active agent to modified release of an active agent is about 20% XR to about 80% DR. Unitary dosage forms with an XR and DR component include any known formulation including bilayer tablets, coated pellets, and the like.

In certain embodiments, the biguanide compounds are provided in the form of a delayed release formulation coupled with an immediate release component of an additional therapeutic agent in a unitary dosage form. The immediate release component can be formulated by any known method such as a layer that envelops the delayed release component or the like. Exemplary ratios of immediate release of an additional therapeutic agent to delayed release of a biguanide compound are about 10% IR to about 90% DR, about 15% IR to about 85% DR, about 20% IR to about 80% DR, about 25% IR to about 75% DR, about 30% IR to about 70% DR, about 35% IR to about 65% DR, about 40% IR to about 60% DR, about 45% IR to about 55% DR, or about 50% IR to about 50% DR. In certain embodiments, the immediate release of an active agent to delayed release of an active agent is about 25% IR to about 75% DR. In certain embodiments, the immediate release of an active agent to delayed release of an active agent is about 20% IR to about 80% DR. Unitary dosage forms with an IR and DR component include any known formulation including bilayer tablets, coated pellets, and the like.

Timed Release Systems

In one embodiment, the delayed-release mechanism is a "timed" or temporal release ("TR") system that releases an active agent, for example a biguanide compound, at certain timepoints subsequent to administration. Timed release systems are well known in the art and suitable timed release systems can include any known excipient and/or coating. For example, excipients in a matrix, layer or coating can delay release of an active agent by slowing diffusion of the active agent into an environment. Suitable timed release excipients include but are not limited to, acacia (gum arabic), agar, aluminum magnesium silicate, alginates (sodium alginate), sodium stearate, bladderwrack, bentonite, carbomer, carrageenan, Carbopol, cellulose, microcrystalline cellulose, ceratonia, chondrus, dextrose, furcellaran, gelatin, Ghatti gum, guar gum, galactomannan, hectorite, lactose, sucrose, maltodextrin, mannitol, sorbitol, honey, maize starch, wheat starch, rice starch, potato starch, gelatin, sterculia gum, xanthum gum, Glyceryl behenate (e.g., Compritol 888 ato), Gylceryl distearate (e.g. Precirol ato 5), polyethylene glycol (e.g., PEG 200-4500), polyethylene oxide, adipic acid, gum tragacanth, ethyl cellulose (e.g., ethyl cellulose 100), ethylhydroxyethyl cellulose, ethylmethyl cellulose, methyl cellulose, hydroxyethyl cellulose, hydroxyethylmethyl cellulose (e.g., KlOOLV, K4M, K15M), hydroxypropyl cellulose, poly(hydroxyethyl methacrylate), cellulose acetate (e.g. cellulose acetate CA-398-10 NF), cellulose acetate phthalate, cellulose acetate propionate, cellulose acetate butyrate, hydroxypropyl methyl cellulose acetate succinate, hydroxypropyl methyl cellulose phthalate, cellulose butyrate, cellulose nitrate, oxypolygelatin, pectin, polygeline, povidone, propylene carbonate, polyandrides, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl cellulose, sodium carboxymethyl-cellulose (CMC), silicon dioxide, vinyl polymers, e.g. polyvinyl pyrrolidones (PVP: povidone), polyvinyl acetates, or polyvinyl acetate phthalates and mixtures, Kollidon SR, acryl derivatives (e.g. polyacrylates, e.g. cross-linked polyacrylates, methycrylic acid copolymers), Splenda® (dextrose, maltodextrin and sucralose) or combinations thereof.

The timed release excipient may be in a matrix with active agent, in another compartment or layer of the formulation, as part of the coating, or any combination thereof. Varying amounts of one or more timed release excipients may be used to achieve a designated release time.

One non-limiting example includes formulations of the TIMERx® system. This controlled release formulation system provides for altered temporal release (SyncroDose™) as well as biphasic release (Geminex®). (See, for example, Staniforth & Baichwal, TIMERx®: novel polysaccharide composites for controlled/programmed release of active ingredients in the gastrointestinal tract, Expert Opin. Drug Deliv., 2(3): 587-89 (2005)). Using formulations such as these for the invention described herein, compositions can be created which target the upper gastrointestinal tract, the lower gastrointestinal tract, or both, in addition to temporally controlling the release of such compounds in any of these locations.

In some embodiments, the timed release systems are formulated to release the compound at an onset of about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, about 180 minutes, about 190 minutes, about 200 minutes, about 210 minutes, about 220 minutes, about 230 minutes, about 240 minutes, about 250 minutes, about 260 minutes, about 270 minutes, about 280 minutes, about 290 minutes, about 300 minutes, about 310 minutes, about 320 minutes, about 330 minutes, about 340 minutes, about 350 minutes, about 360 minutes, about 370 minutes, about 380 minutes, about 390 minutes, about 400, about 400, about 410, or about 420 minutes subsequent to administration. In embodiments with multiple releases, timed release systems are formulated to release at more than one time point. In certain embodiments, the timed release systems are formulated to release at an onset of about 10 minutes, about 30 minutes, about 120 minutes, about 180 minutes and about 240 minutes after administration. In certain embodiments the timed release systems are formulated to release at an onset of about 5 to about 45 minutes, about 105 to about 135 minutes, about 165 to about 195 minutes, about 225 to about 255 minutes or a combination of times thereof following administration to a patient.

Enteric Coatings and pH Dependent Systems

The formulation may also be coated with an enteric coating, which protects an active agent, for example a biguanide compound, from degradation in an acidic environment, such as the stomach, and allows a delayed release into a target area, for example the ileum, for uptake.

The enteric coating may be, as a non-limiting example, wax or wax like substance, such as carnauba wax, fatty alcohols, hydrogenated vegetable oils, zein, shellac, sucrose, Arabic gum, gelatin, dextrin, psyllium husk powder, polymethacrylates, anionic polymethacrylates, mixtures of poly(methacrylic acid, methyl methacrylate), polymers or copolymers derived from acrylic and/or methacrylic acid esters, cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, mixtures of poly(methacrylic acid, ethyl acrylate), ethylcellulose, methylcellulose, propylcellulose, chitosan succinate, chitosan succinate, polyvinyl acetate phthalate (PVAP), polyvinyl acetate polymers carboxymethylethyl cellulose and compatible mixtures thereof. In addition, an inactive intermediate film may be provided between the biguanide compound, and the enteric coating to prevent interaction of the biguanide compound with the enteric coating.

In one non-limiting example, silicone microspheres for pH-controlled gastrointestinal drug delivery have been described by Carelli et al., Int. J. Pharmaceutics 179: 73-83, 1999. The microspheres are pH-sensitive semi-interpenetrating polymer hydrogels made of varying proportions of poly(methacrylic acid-co-methylmethacrylate) (EUDRAGIT® L100 or EUDRAGIT® S100) and crosslinked polyethylene glycol 8000 that are encapsulated into silicone microspheres. The EUDRAGIT® series of methacrylic acid copolymers are commercially available from Evonik Industries in Darmstadt, Germany.

The enteric coatings can be formulated to release a biguanide compound at a desired pH using combinations of enteric polymers. It is well-known that different locations of the gastrointestinal system have specific pHs. For example, the duodenum may correspond to a pH 5.5 environment and the jejunum may correspond to pH 6.0 environment. In preferred embodiments, the enteric coatings are formulated to release the compound at an onset of a desired pH, e.g., in the distal small intestine and lower intestine, i.e., at about pH 6, about pH 6.5, or about pH 7. In embodiments with multiple releases, the enteric coatings are formulated to release at an onset of two or more pH values. In certain embodiments, the enteric coatings are formulated to release at an onset of pH 6.0, 6.5 and 7.0. In certain embodiments, the enteric coatings are formulated to release at an onset of pH 6.5 and 7.0. In certain embodiments, the enteric coatings are formulated to release at the jejunum, ileum, and lower intestine. In yet other embodiments, the enteric coatings are used in combination with other release systems such as a timed release system.

In yet other embodiments, the enteric coatings are used in combination with an immediate release/extended release unitary dosage form. For example, a unitary dosage form, such as a bilayer tablet with a 20% IR/80% MR component of the biguanide compound can be coated with an enteric coating that releases at pH, e.g., 5.5, 6.0, 6.5, 7.0 so that the release is delayed until the dosage form reaches a pH of e.g., 5.5, 6.0, 6.5, 7.0 thereby releasing the IR component immediately and the MR component according to its MR release properties. In certain instances, the enteric coatings are used in combination with an immediate release/timed release unitary dosage forms.

The microcapsules gastroretentive systems described in U.S. Pat. Nos. 6,022,562, 5,846,566 and 5,603,957, can be used in the delayed release delivery methods described herein. Microparticles of an active agent or drug are coated by spraying with a material consisting of a mixture of a film-forming polymer derivative, a hydrophobic plasticizer, a functional agent and a nitrogen-containing polymer. The resulting microcapsules are less than or equal to 1000 microns (gm) in size, and in certain cases such microcapsules are between 100 and 500 microns. These microcapsules remain in the small intestine for at least 5 hours.

Film-forming polymer derivatives used in such microcapsules include, but are not limited to, ethylcellulose, cellulose acetate, and non-hydrosoluble cellulose derivates. The nitrogen-containing polymers include, but are not limited to, polyacrylamide, vinylamide, poly-N-vinyl-lactam and poly-vinylpyrrolidone. The plasticizer used in such microcapsule include, but are not limited to, glycerol esters, phthalates, citrates, sebacates, cetylalcohol esters, castor oil and cutin. The surface-active and/or lubricating agent used in such microcapsule include, but are not limited to, anionic surfactants, such as by way of example the alkali metal or alkaline-earth metal salts of fatty acids, stearic acid and/or oleic acid, nonionic surfactants, such as by way of example, polyoxyethylenated esters of sorbitan and/or polyoxyethylenated esters of sorbitan and/or polyoxyethylenated derivatives of castor oil; and/or lubricants such as stearates, such as by way of example, calcium, magnesium, aluminum stearate, zinc stearate, stearylfumarate, sodium stearylfimarate, and glyceryl behenate.

One non-limiting example of a lower GI delivery formulation comprises a tablet for lower GI delivery. The inner composition of the tablet comprises about 0.01% weight to about 10.0% by weight of a suitable active ingredient; about 50% by weight to about 98% by weight of a hydrocolloid gum obtainable from higher plants; and about 2% by weight to about 50% by weight of a pharmaceutically acceptable excipient such as a binder. Other optional materials may be present that will assist in establishing the desired characteristics of the pharmaceutical composition. These include materials that may enhance absorption of the active ingredient in the lower GI, may protect the active ingredient against degradation, may prevent dissolution, and the like. Optionally surrounding the inner composition of the tablet is a coating that is preferably of enteric polymeric material.

The formulation is designed to take advantage of (1) the protective characteristics of the hydrocolloid obtainable from higher plants in the upper GI and (2) the disintegrative characteristics of the hydrocolloid in the lower GI. Thus, the inner composition of the tablet may be one of several designs: (a) it may be a matrix of a therapeutically effective amount of the active ingredient uniformly dispersed throughout in combination with a high percentage of the hydrocolloid and a generally lesser amount of other excipients; (b) it may have a core, in which the active ingredient is concentrated, surrounded by a layer of material that is free of the active ingredient and that has a high percentage of the hydrocolloid and a generally lesser amount of other excipients; (c) it may have a concentration gradient of the active ingredient such that there is a greater amount in the core of the tablet with lesser amounts in multiple layers surrounding the core and very little or no active ingredient in the outer layer. Whether the design of the tablet is that of (a), (b) or (c) above, the specificity for regional delivery to the lower GI is enhanced by enterically coating the tablet with an appropriate enteric coating material.

Suitable hydrocolloids are well known in the art. See for example "The Chemistry of Plant Gums and Mucilages" by Smith and Montgomery from the A.C.S. Monograph series, #141, 1959, Reinhold Publishing Co. and the Eighteenth Edition of The Merck Index. In general, the amount of the hydrocolloid that will be used is an amount that allows the composition to traverse the upper GI tract without significant disintegration and without releasing significant amounts of active ingredient in the upper GI tract, i.e. to provide a delayed-release profile. Generally, that amount of hydrocolloid will be more than about 50% but less than about 98%. Depending on individual variability, whether a patient has eaten or has fasted, and other factors, a tablet will traverse the stomach and upper intestinal tract in about 3 to 6 hours. During this time, little active ingredient (less than 20%, preferably less than 10%) is released from the tablet of this invention. Once the tablet reaches the lower GI, the release of the active ingredient is triggered by enzymatic degradation of the galactomannan gum.

Modified Release Formulations

In additional embodiment, the methods and compositions directed to biguanide compound delivery may further employ controlled, sustained, or extended release formulations known collectively as "modified release" formulations. Compositions can be administered by modified release systems or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Such dosage forms can be used to provide modified release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable modified release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are further adapted for modified release.

In some embodiments, the modified release systems are formulated to release the compound at a duration of about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, about 180 minutes, about 190 minutes, about 200 minutes, about 210 minutes, about 220 minutes, about 230 minutes, about 240 minutes, about 250 minutes, about 260 minutes, about 270 minutes, about 280 minutes, about 290 minutes, about 300 minutes, about 310 minutes, about 320 minutes, about 330 minutes, about 340 minutes, about 350 minutes, about 360 minutes, about 370 minutes, about 380 minutes, about 390 minutes, about 400, about 400, about 410, or about 420 minutes subsequent to onset of the release. In embodiments with multiple releases, modified release systems are formulated to release at more than one durations of time at different time points.

In one non-limiting example, chitosan and mixtures of chitosan with carboxymethylcellulose sodium (CMC-Na) have been used as vehicles for the sustained release of active ingredients, as described by Inouye et al., Drug Design and Delivery 1: 297-305, 1987. Mixtures of these compounds and agents of the combinations of the invention, when compressed under 200 kg/cm2, form a tablet from which the active agent is slowly released upon administration to a patient. The release profile can be changed by varying the ratios of chitosan, CMC-Na, and active agent(s). The tablets can also contain other additives, including lactose, CaHPO4 dihydrate, sucrose, crystalline cellulose, or croscarmellose sodium.

In another non-limiting example, Baichwal, in U.S. Pat. No. 6,245,356, describes sustained release oral, solid dosage forms that include agglomerated particles of a therapeutically active medicament in amorphous form, a gelling agent, an ionizable gel strength enhancing agent and an inert diluent. The gelling agent can be a mixture of a xanthan gum and a locust bean gum capable of cross-linking with the xanthan gum when the gums are exposed to an environmental fluid. Preferably, the ionizable gel enhancing agent acts to enhance the strength of cross-linking between the xanthan gum and the locust bean gum and thereby prolonging the release of the medicament component of the formulation. In addition to xanthan gum and locust bean gum, acceptable gelling agents that may also be used include those gelling agents well known in the art. Examples include naturally occurring or modified naturally occurring gums such as alginates, carrageenan, pectin, guar gum, modified starch, hydroxypropylmethylcellulose, methylcellulose, and other cellulosic materials or polymers, such as, for example, sodium carboxymethylcellulose and hydroxypropyl cellulose, and mixtures of the foregoing.

In another non-limiting formulation useful for the combinations of the invention, Baichwal and Staniforth in U.S. Pat. No. 5,135,757 describe a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical-filler (such as, for example, lactose, dextrose, sucrose, sorbitol, xylitol, fructose or mixtures thereof). After mixing the excipient with a tricyclic compound/corticosteroid combination, or combination agent, of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

Slow-release formulations can also include a coating which is not readily water-soluble but which is slowly attacked and removed by water, or through which water can slowly permeate. Thus, for example, the combinations of the invention can be spray-coated with a solution of a binder under continuously fluidizing conditions, such as describe by Kitamori et al., U.S. Pat. No. 4,036,948. Examples of water-soluble binders include pregelatinized starch (e.g., pregelatinized corn starch, pregelatinized white potato starch), pregelatinized modified starch, water-soluble celluloses (e.g. hydroxypropyl-cellulose, hydroxymethyl-cellulose, hydroxypropylmethyl-cellulose, carboxymethyl-cellulose), polyvinylpyrrolidone, polyvinyl alcohol, dextrin, gum arabicum and gelatin, organic solvent-soluble binders, such as cellulose derivatives (e.g., cellulose acetate phthalate, hydroxypropylmethyl-cellulose phthalate, ethylcellulose).

In another non-limiting example, Villa et al., in U.S. Pat. No. 6,773,720, describes a modified-release system containing an inner lipophilic matrix where an active ingredient is inglobated and an outer hydrophilic matrix in which the lipophilic matrix is dispersed. An active ingredient, such as a biguanide or related heterocyclic compound, is first inglobated in a low melting lipophlilic excipient or mixture of excipients while heating to soften and/or melt the excipient itself, which thereby incorporates the active ingredient by simple dispersion. After cooling at room temperature, an inert matrix forms, which can be reduced in size to obtain matrix granules containing the active ingredient particles. The inert matrix granules are subsequently mixed together with one or more hydrophilic water-swellable excipients. In this respect, when the composition is contacted with biological fluids, a high viscosity swollen layer is formed, which coordinates the solvent molecules and acts as a barrier to penetration of the aqueous fluid itself inside the new structure. Said barrier antagonizes the staring "burst effect"

caused by dissolution of the active ingredient inglobated inside the inert matrix, which is in its turn inside the hydrophilic matrix. One commercially available system of this type is from Cosmo Technologies Limited (Italy) under the trade name MMX® technology. The lipophilic/hydrophilic matrices can be further enterically coated for pH specific delivery.

Formulations for upper intestinal delivery, lower intestinal delivery or both are known in the art. Targeting of active ingredients to various regions of the gut is described, e.g., in The Encyclopedia of Pharmaceutical Technology, by James Swarbrick and James Boylan, Informa Health Care, 1999, at pp. 287-308. Any suitable formulation for gastrointestinal delivery for site-specific delivery and/or specific temporal delivery (i.e. delayed, controlled, extended, or sustained release) can be used with the invention and is contemplated herein.

Any of the delivery systems described herein may be used in combination with others to achieve multiple releases and/or specific release profiles. In some embodiments, the biguanide compound is in a formulation that achieves multiple releases in gastrointestinal locations following administration. In certain embodiments, the biguanide compound is in a multiple release formulation that releases at an onset of about 10 minutes, about 30 minutes, about 120 minutes, about 180 minutes, about 240 minutes, or combinations thereof following administration. In certain embodiments, the biguanide compound is in a multiple release formulation that releases at an onset of about 5 to about 45 minutes, about 105 to about 135 minutes, about 165 to about 195 minutes, about 225 to about 255 minutes, or combinations thereof following administration.

In certain embodiments, the biguanide compound is in a multiple release formulation that releases in the duodenum, jejunum, ileum, lower intestine or combinations thereof following administration. In yet other embodiments, the biguanide compound is in a multiple release formulation that releases at an onset of about pH 5.5, about pH 6.0, at about pH 6.5, about pH 7.0, or combinations thereof following administration. In yet other embodiments, the biguanide compound is in a multiple release formulation that releases in ranges at about pH 5.0 to about pH 6.0, about pH 6.0 to about pH 7.0, about pH 7.0 to about pH 8.0, or combinations thereof following administration. In yet other embodiments, the biguanide compound is in a multiple release formulation that releases a fraction or portion of the biguanide as an immediate release with the rest of the compound released in a delayed manner as described herein.

Oral Dosage Forms

Oral dosage forms suitable for use in the subject compositions and methods include tablets, hard capsules, push-fit capsules made of gelatin, as well as soft, sealed capsules made of gelatin and a plasticizer, such as glycerol or sorbitol, as well as troches, lozenges, aqueous or oily suspensions, dispersible powders or granules, emulsions, syrups or elixirs. Suitable oral dosage forms can be prepared according to any method known to the art for the manufacture of pharmaceutical compositions, and such compositions can contain one or more agents selected from, by way of non-limiting example, sweetening agents, flavoring agents, coloring agents and preserving agents in order to provide pharmaceutically elegant and palatable preparations.

Tablets contain the active ingredient in admixture with pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservatives, disintegrants (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets are coated by known techniques to delay disintegration and absorption in the gastrointestinal tract and thereby minimize systemic bioavailability as described more fully herein.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil. Alternatively, push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

It should be understood that in addition to the ingredients particularly mentioned above, the compounds and compositions described herein can include other agents conventional in the art having regard to the type of formulation in question, for example those suitable for oral administration can include flavoring agents.

In various embodiments, the compositions provided herein are in liquid form. Liquid forms include, by way of non-limiting example, neat liquids, solutions, suspensions, dispersions, colloids, foams and the like. In certain instances, liquid forms contain also a nutritional component or base (e.g., derived from milk, yogurt, shake, or juice). In some aspects, the compound are micronized or as nanoparticles in the liquid form. In certain instances, the compounds may be coated to mask the tastant properties. In other instances, the compounds are coated to modify delivery to the intestine and colon.

Aqueous solutions or suspensions contain the active ingredient(s) in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous solutions or suspensions can also contain one or more preservatives, for example ethyl, or n-propyl p-hydroxybenzoate, one or more coloring agents, one or more flavoring agents, and one or more sweetening agents, such as sucrose, saccharin or aspartame. In certain instances, the flavoring agents are the compounds.

Oily suspensions can be formulated by suspending the active ingredient(s) in a vegetable oil, for example arachis oil, olive oil, sesame oil or coconut oil, or in mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation. These compositions can be preserved by the addition of an antioxidant such as butylated hydroxyanisol or alpha-tocopherol.

Dispersible powders and granules suitable for preparation of an aqueous solutions or suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, can also be present. These compositions can be preserved by the addition of an antioxidant such as ascorbic acid.

Compositions can also be in the form of an oil-in-water emulsion. The oily phase can be a vegetable oil, for example olive oil or arachis oil, or a mineral oil, for example liquid paraffin or mixtures of these. Suitable emulsifying agents can be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening agents, flavoring agents, preservatives and antioxidants.

Syrups and elixirs can be formulated with sweetening agents, for example glycerol, propylene glycol, sorbitol or sucrose. Such formulations can also contain a demulcent, a preservative, flavoring and coloring agents and antioxidant.

Compositions can also be formulated in rectal compositions such as suppositories or retention enemas, e.g., containing conventional suppository bases such as cocoa butter, polyethylene glycol, or other glycerides. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

Accordingly, pharmaceutical compositions are also provided comprising the biguanide compound in a delayed-release formulation suitable for oral administration such as a tablet, capsule, cachet, pill, lozenge, powder or granule, solution, liquid, or suspension. The pharmaceutical composition is preferably in a unit dosage form suitable for single administration of precise dosages, e.g., 100 mg, 200 mg, 250, mg, 300 mg, 400 mg, 500 mg, 600 mg, 750 mg, 800 mg, or 1000 mg of the desired biguanide compound, particularly metformin, phenformin, buformin or imeglimin or a salt thereof. The pharmaceutical composition may comprise conventional pharmaceutical carriers or excipients and the biguanide compound according to the invention as an active ingredient. They may further comprise other medicinal or pharmaceutical agents, carriers, adjuvants, etc.

Suitable carriers include inert diluents or fillers, water and various organic solvents. The compositions can, if desired, contain additional ingredients such as flavorings, binders, excipients and the like. Thus for oral administration, tablets containing various excipients, such as citric acid can be employed together with various disintegrants such as starch or other cellulosic material, alginic acid and certain complex silicates and with binding agents such as sucrose, gelatin and acacia. Additionally, lubricating agents such as magnesium stearate, sodium lauryl sulfate and talc are often useful for tableting purposes. Other reagents such as an inhibitor, surfactant or solubilizer, plasticizer, stabilizer, viscosity increasing agent, or film forming agent can also be added. Solid compositions of a similar type can also be employed in soft and hard filled gelatin capsules. Materials include lactose or milk sugar and high molecular weight polyethylene glycols. When aqueous suspensions or elixirs are desired for oral administration the active compound therein can be combined with various sweetening or flavoring agents, coloring matters or dyes and, if desired, emulsifying agents or suspending agents, together with diluents such as water, ethanol, propylene glycol, glycerin, or combinations thereof.

Excipients

Any of the compositions or formulations described herein include any commonly used excipients in pharmaceutics and are selected on the basis of compatibility with the active agent(s) and release profile properties of the desired dosage form. Excipients include, but are not limited to, binders, fillers, flow aids/glidents, disintegrants, lubricants, stabilizers, surfactants, and the like. A summary of excipients described herein, may be found, for example in Remington: The Science and Practice of Pharmacy, Nineteeth Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999), herein incorporated by reference in their entirety.

Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Disintegrants facilitate breakup or disintegration of oral solid dosage forms after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel0, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Solt), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp; sodium lauryl sulfate; sodium lauryl sulfate in combination starch; and the like.

Lubricants are compounds which prevent, reduce or inhibit adhesion or friction of materials. Exemplary lubricants include, e.g., stearic acid; calcium hydroxide; talc; sodium stearyl fumerate; a hydrocarbon such as mineral oil, hydrogenated castor oil or hydrogenated vegetable oil such as hydrogenated soybean oil (Sterotex®); higher fatty acids and their alkali-metal and alkaline earth metal salts, such as aluminum, calcium, magnesium, zinc; stearic acid, sodium stearates, magnesium stearates, glycerol, talc, waxes, Stearowet® boric acid, sodium benzoate, sodium acetate, sodium chloride, leucine, a polyethylene glycol or a methoxypolyethylene glycol such as Carbowax™, ethylene oxide polymers, sodium oleate, glyceryl behenate (E.g. Compritol 888 Ato), glyceryl disterate (Precirol Ato 5), polyethylene glycol, magnesium or sodium lauryl sulfate, colloidal silica such as Syloid™, Carb-O—Si10, DL-leucine, a starch such as corn starch, silicone oil, a surfactant, and the like.

Flow-aids or glidants improve the flow characteristics of powder mixtures. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

Plasticizers aid in coating of oral solid dosage forms. Exemplary plasticizers include, but are not limited to, triethyl citrate, triacetin (glyceryl triacetate), acetyl triethyl citrate, polyethylene glycols (PEG 4000, PEG 6000, PEG 8000), Carbowax 400 (polyethylene glycol 400), diethyl phthalate, diethyl sebacate, acetyltriethylcitrate, oleic acid, glyceralmonosterate, tributyl citrate, acetylated monoglycerides, glycerol, fatty acid esters, propylene glycol, and dibutyl phthalate and the like.

The aforementioned excipients are given as examples only and are not meant to include all possible choices. Other suitable excipient classes include coloring agents, granulating agents, preservatives, anti-foaming agents, solubulizers and the like. Additionally, many excipients can have more than one role or function, or can be classified in more than one group; the classifications are descriptive only, and are not intended to limit any use of a particular excipient.

Combination Therapies

The compositions of the embodiments described herein may be co-administered with known therapies for the treatment of any of the conditions described herein. Co-administration can also provide for additive or synergistic effects, resulting in the need for lower dosages of a known therapy, the compositions described herein, or both. Additional benefits of co-administration include the reduction in toxicities associated with any of the known therapies.

Co-administration includes simultaneous administration in separate compositions, administration at different times in separate compositions, or administration in a composition in which both agents are present. Thus, in some embodiments, compositions described herein and a known therapy are administered in a single treatment. In some embodiments, the compositions described herein and a known therapy are admixed in a resulting composition. In some embodiments, compositions described herein and the known therapy are administered in separate compositions or administrations.

Administration of compositions described herein and known therapies described herein may be by any suitable means. Administration of a composition described herein and a second compound (e.g., diabetes drug or obesity drug) may be by any suitable means. If the compositions described herein and a second compound are administered as separate compositions, they may be administered by the same route or by different routes. If the compositions described herein and a second compound are administered in a single composition, they may be administered by any suitable route such as, for example, oral administration. In certain embodiments, compositions of metformin or an analog thereof (including salts, solvates, polymorphs, hydrates, N-oxides, or prodrugs thereof) and second compounds can be administered to the same region or different regions of the gastrointestinal tract. For example, metformin or an analog thereof (including salts, solvates, polymorphs, hydrates, N-oxides, or prodrugs thereof)s can be administered in combination with an anti-diabetic drug to be delivered to the duodenum, jejunum, ileum, or colon.

Therapies, drugs and compounds useful for the treatment of hyperglycemia and/or diseases or conditions associated therewith, e.g., diabetes may be administered with the compositions disclosed herein. Diabetic drugs and compounds include, but are not limited to, those that decrease triglyceride concentrations, decrease glucose concentrations, and/or modulate insulin (e.g. stimulate insulin production, mimic insulin, enhance glucose-dependent insulin secretion, suppress glucagon secretion or action, improve insulin action or insulin sensitizers, or are exogenous forms of insulin).

Drugs that decrease triglyceride level include but are not limited to ascorbic acid, asparaginase, clofibrate, colestipol, fenofibrate mevastatin, pravastatin, simvastatin, fluvastatin, or omega-3 fatty acid. Drugs that decrease LDL cholesterol level include but are not limited to clofibrate, gemfibrozil, and fenofibrate, nicotinic acid, mevinolin, mevastatin, pravastatin, simvastatin, fluvastatin, lovastatin, cholestyrine, colestipol or probucol.

In another aspect, compositions of the embodiments described herein may be administered in combination with glucose-lowering compounds.

The medication classes of thiazolidinediones (also called glitazones), sulfonylureas, meglitinides, biguanides, alpha-glucosidase inhibitors, DPP-IV inhibitors, and incretin mimetics have been used as adjunctive therapies for hyperglycemia and diabetes mellitus (type 2) and related diseases.

Drugs that decrease glucose level include but are not limited to glipizides, glyburides, exenatide (Byetta®), incretins, sitagliptin (Januvia®), pioglitizone, glimepiride, rosiglitazone, metformin, vildagliptin, saxagliptin (Onglyza™), sulfonylureas, meglitinide (e.g., Prandin®) glucosidase inhibitor, biguanides (e.g., Glucophage®), repaglinide, acarbose, troglitazone, nateglinide, natural, synthetic or recombinant insulin and derivatives thereof, and amylin and amylin derivatives.

When administered sequentially, the combination may be administered in two or more administrations. In an alternative embodiment, it is possible to administer one or more the biguanide compounds and one or more additional active ingredients by different routes. The skilled artisan will also recognize that a variety of active ingredients may be administered in combination with one or more the biguanide compounds that may act to augment or synergistically enhance the control prevention, amelioration, attenuation, or treatment of obesity or eating disorders or conditions.

According to the methods provided herein, when co-administered with at least one other obesity reducing (or anti-obesity) or weight reducing drug, the compounds of the disclosure may be: (1) co-formulated and administered or delivered simultaneously in a combined formulation; (2) delivered by alternation or in parallel as separate formulations; or (3) by any other combination therapy regimen known in the art. When delivered in alternation therapy, the methods provided may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments, compositions provided herein may be used with other commercially available diet aids or other weight loss and/or anti-obesity agents, such as, by way of example, PYY and PYY agonists, GLP-1 and GLP-1 agonists, a DPP-IV inhibitor, CCK and CCK agonists, exendin and exendin agonists, GIP and GIP agonists, amylin and amylin agonists, ghrelin modulators (e.g., inhibitors) and leptin and leptin agonists. In certain instances, compositions comprising the biguanide compound provided herein are used in combination with amylin, amylin agonists or mimetics. Exemplary amylin agonists or mimetics include pramlintide and related compounds. In certain instances, the compounds and compositions provided herein are used in combination with leptin, leptin agonists or mimetics. Additional leptin agonists or mimetics can be identified using the methods described by U.S. Pat. No. 7,247,427 which is incorporated by reference herein. In further instances, the compounds and compositions provided herein increase leptin sensitivity and increase effectiveness of leptin, leptin agonists or mimetics.

Additional anti-obesity agents suitable for use in the subject methods include those that are in current development. Other anti-obesity agents include phentermine, fenfluramine, sibutramine, rimonabant, topiramate, zonisamide, bupropion, naltrexone, lorcaserin, or related sympathomimetics and orlistat or other intestinal lipase inhibitors, alone or in combination. Therapies, drugs and compounds useful for the treatment of weight loss, binge eating, food addictions and cravings may be administered with the compositions described herein. For example, the patient may further be administered at least one other drug which is known to suppress hunger or control appetite. Such therapies drugs and compounds include but are not limited to phenteramines such as Meridia® and Xenical®. Additional therapies, drugs and compounds are known in the art and contemplated herein.

As such, in one aspect, the compound may be used as part of a combination therapy for the control, prevention or treatment of obesity or eating disorders or conditions. Compounds used as part of a combination therapy to treat obesity or reduce weight include, but are not limited to, central nervous system agents that affect neurotransmitters or neural ion channels, including antidepressants (bupropion), noradrenalin reuptake inhibitors (GW320659), selective 5HT 2c receptor agonists, antiseizure agents (topiramate, zonisamide), some dopamine antagonists, and cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, .alpha.-melanocyte-stimulating hormone analogues, melanocoritin-4 receptor agonists, and agents that affect insulin metabolism/activity, which include protein-tyrosine phosphatase-1B inhibitors, peroxisome proliferator activated receptor-gamma receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, liraglutide, dipeptidyl peptidase IV inhibitors), and those that decrease ghrelin activity, as well as amylin analogues (pramlintide); agents that may increase resting metabolic rate (selective (3-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis (cerulenin and C75), carboxypeptidase inhibitors, indanone/indanols, amino sterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion.

Other compounds include ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-113715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1/D2 agonists; melanocortin modulators; verongamine; neuropeptide Y antagonists; melanin-concentrating hormone receptor antagonists; dual PPAR alpha/gamma agonists; CGEN-P-4; kinase inhibitors;

human MCH receptor antagonists; GHS-R antagonists; ghrelin receptor agonists; DG70 inhibitors; cotinine; CRF-BP inhibitors; urocortin agonists; UCL-2000; impentamine; .beta.-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPY5RA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; H3 histamine antagonists; PPARpan agonists; EP-01492; hormone-sensitive lipase inhibitors; fatty acid-binding protein 4 inhibitors; thiolactone derivatives; protein tyrosine phosphatase 1B inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; neuropeptide Y antagonist; angiogenesis inhibitors; G protein-coupled receptor agonists; nicotinic therapeutics (ChemGenex); anti-obesity agents (Abbott); neuropeptide Y modulators; melanin concentrating hormone; GW-594884A; MC-4R agonist; histamine H3 antagonists; orphan GPCR modulators; MITO-3108; NLC-002; HE-2300; IGF/IBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; neuropeptide Y1 antagonist; beta-3 adrenoceptor agonists; ob gene products (Eli Lilly & Co.); SWR-0342-SA; beta-3 adrenoceptor agonist; SWR-0335; SP-18904; oral insulin mimetics; beta 3 adrenoceptor agonists; NPY-1 antagonists; .beta.-3 agonists; obesity therapeutics (7TM Pharma); 11beta-hydroxysteroid dehydrogenase (HSD)1 inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI 8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S) sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; NPY-1 antagonists; A-71378; ®-didesmethylsibutramine; amide derivatives; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BIBP-3226; HP-228; talibegron; FR-165914; AZM-008; AZM-016; AZM-120; AZM-090; vomeropherin; BMS-187257; D-3800; AZM-131; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; AZM-134; AZM-127; AZM-083; AZM-132; AZM-115; exopipam; SSR-125180; obesity therapeutics (Melacure Therapeutics AB); BRL-35135; SR-146131; P-57; AZM-140; CGP-71583A; RF-1051; BMS-196085; manifaxine; beta-3 agonists; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; metformin; AOD-9604; ATL-062; BVT-933; GT389-255; SLV319; HE-2500; PEG-axokine; L-796568; and ABT-239.

In some embodiments, compounds for use in combination with a composition comprising the biguanide compound provided herein include rimonabant, sibutramine, orlistat, PYY or an analog thereof, CB-1 antagonist, leptin, phentermine, and exendin analogs. Exemplary dosing ranges include phentermine resin (30 mg in the morning), fenfluramine hydrochloride (20 mg three times a day), and a combination of phentermine resin (15 mg in the morning) and Lorcaserin (30 mg before the evening meal), and sibutramine (10-20 mg). Weintraub et al. (1984) Arch. Intern. Med. 144:1143-1148.

In further embodiments, compounds for use in combination with a composition provided herein include GPR119 agonists (e.g., anandamide; AR-231, 453; MBX-2982; Oleoylethanolamide; PSN-365,963; PSN-632,408; palmitoylethanolamide), GPR120 agonists (e.g., omega-3 fatty acids including, but not limited to, a-linolenic acid, docosapentaenoic acid, docosahexaenoic acid, eicosatrienoic acid, eicosatetraenoic acid, eicosapentaenoic acid, heneicosapentaenoic acid, hexadecatrienoic acid, stearidonic acid, tetracosahexaenoic acid and tetracosapentaenoic acid), and GPR 40, GPR41 and GPR 43 agonists (e.g., free fatty acids including short-, medium-, and long-chain saturated and unsaturated fatty acids).

In some embodiments, a composition provided herein is used as an adjunctive therapy to a bariatric surgical procedure. Bariatric surgery is a procedure for weight loss and relates to modifications with the gastrointestinal tract and includes such procedures as gastric banding, sleeve gastrectomy, GI bypass procedure (e.g., roux en Y, biliary duodenal bypass, loop gastric bypass), intragastric balloon, vertical banded, gastroplasty, endoluminal sleeve, biliopancreatic diversion, and the like. In certain instances, a the composition provided herein is adjunctive to gastric banding. In certain instances, a composition is adjunctive to GI bypass procedures. In yet other instances, a composition provided herein is adjunctive to sleeve gastrectomy. In certain embodiments, a composition provided herein as an adjunctive therapy to bariatric surgery is administered prior to the bariatric procedure. In certain embodiments, a composition provided herein as an adjunctive therapy to bariatric surgery is administered after the bariatric procedure. In certain instances, when used as adjunctive therapy, the dosage and amounts of a composition provided herein may be adjusted as needed with respect to the bariatric procedure. For example, amounts of a composition provided herein administered as an adjunct therapy to a bariatric procedure may be reduced by one-half of normal dosages or as directed by a medical professional.

Combination therapy can be exploited, for example, in modulating metabolic syndrome (or treating metabolic syndrome and its related symptoms, complications and disorders), wherein the compositions provided herein can be effectively used in combination with, for example, the active agents discussed above for modulating, preventing or treating diabetes, obesity, hyperlipidemia, atherosclerosis, and/or their respective related symptoms, complications and disorders.

Methods for Evaluating Treatment

Evaluation of Treatment of Diabetes

The effect of the biguanide compound treatment of the invention on aspects of diabetic disease can be evaluated according to methods known in the art and common practiced by physicians treating diabetic patients.

Efficacy of treatment of diabetes/metabolic syndrome and diabetes-associated conditions with the compositions and methods described herein can be assessed using assays and methodologies known in the art. By way of example, quantitative assessment of renal function and parameters of renal dysfunction are well known in the art. Examples of assays for the determination of renal function/dysfunction include scrum creatinine level; creatinine clearance rate; cystatin C clearance ratc, 24-hour urinary creatinine clearance, 24-hour urinary protein secretion; Glomerular filtration rate (GFR); urinary albumin creatinine ratio (ACR); albumin excretion rate (AER); and renal biopsy.

Quantitative assessment of pancreatic function and parameters of pancreatic dysfunction or insufficiency are also well known in the art. Examples of assays for the determination of pancreas function/dysfunction include evaluating pancreatic functions using biological and/or physiological parameters such as assessment of islets of Langerhans size, growth and/or secreting activity, beta-cells size, growth and/or secreting activity, insulin secretion and circulating blood levels, glucose blood levels, imaging of the pancreas, and pancreas biopsy, glucose uptake studies by oral glucose challenge, assessment of cytokine profiles, blood-gas analysis, extent of blood-perfusion of tissues, and angiogenesis within tissues.

Additional assays for treatment of diabetes and diabetes-associated conditions are known in the art and are contemplated herein.

Evaluation of Treatment of Weight Loss, Obesity and Eating Disorders

In treatment of obesity it is desired that weight and/or fat is reduced in a patient. By reducing weight it is meant that the patient loses a portion of his/her total body weight over the course of treatment (whether the course of treatment be days, weeks, months or years). Alternatively, reducing weight can be defined as a decrease in proportion of fat mass to lean mass (in other words, the patient has lost fat mass, but maintained or gained lean mass, without necessarily a corresponding loss in total body weight). An effective amount of a the biguanide compound treatment administered in this embodiment is an amount effective to reduce a patient's body weight over the course of the treatment, or alternatively an amount effective to reduce the patient's percentage of fat mass over the course of the treatment. In certain embodiments, the patient's body weight is reduced, over the course of treatment, by at least about 1%, by at least about 5%, by at least about 10%, by at least about 15%, or by at least about 20%. Alternatively, the patient's percentage of fat mass is reduced, over the course of treatment, by at least 1%, at least 5%, at least 10%, at least 15%, at least 20%, or at least 25%.

Total body weight and fat content can be measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In embodiments wherein methods of treating, reducing, or preventing food cravings in a patient are provided, food cravings can be measured by using a questionnaire, whether known in the art or created by the person studying the food cravings. Such a questionnaire would preferably rank the level of food cravings on a numerical scale, with the patient marking 0 if they have no food cravings, and marking (if on a scale of 1-10) 10 if the patient has severe food cravings. The questionnaire would preferably also include questions as to what types of food the patient is craving. Binge eating can be determined or measured using a questionnaire and a Binge Eating Scale (BES). Binge eating severity can be divided into three categories (mild, moderate, and severe) based on the total BES score (calculated by summing the scores for each individual item). Accordingly, methods are provided for reducing the BES score of a patient comprising administering to a patient in need thereof a compound treatment in an amount effective to reduce the BES score of the patient. In some embodiments, administration of a compound treatment changes the BES category of the patient, for example, from severe to moderate, from severe to mild, or from moderate to mild.

Pre-Treatment Evaluation of Patient Hormonal Profile

In some embodiments, patients are pre-evaluated for expression of metabolic hormones using methods described herein. The therapy provided to the individual can thus be targeted to his or her specific needs. In embodiments, a patient's hormonal profile is pre-evaluated and depending on the changes that the physician desires to affect, a certain determined amount of the compound/metabolite combination is administered. The evaluation process can be repeated and the treatment adjusted accordingly at any time during or following treatment.

Hormone Assays

In embodiments, the levels of hormones assayed in association with the methods of the invention, including, but not limited to, GLP-1, GLP-2, GIP, oxyntomodulin, PYY, CCK, glycentin, insulin, glucagon, ghrelin, amylin, uroguanylin, C-peptide and/or combinations thereof are detected according to standard methods described in the literature. For example, proteins can be measured by immunological assays, and transcription products by nucleic acid amplification techniques. Functional assays described in the art can also be used as appropriate. In embodiments, samples assayed comprise cultured cells, patient cell or tissue samples, patient body fluids, e.g., blood or plasma, etc. Similarly, the levels of analytes (e.g., glucose, triglycerides, HDL, LDL, apoB and the like) assayed in association with the methods of the invention are detected according to any known method.

For example, immunofluorescence can be used to assay for GLP-1. Cells can be grown on matrigel-coated cover slips to confluent monolayers in 12-well plates at 37° C., fixed in 4% paraformaldehyde in phosphate-buffered saline (PBS) and incubated with primary antiserum (e.g., rabbit anti-alpha gustducin, 1:150; Santa Cruz Biotechnology, and rabbit anti-GLP-1, Phoenix) overnight at 4° C. following permeabilization with 0.4% Triton-X in PBS for 10 minutes and blocking for 1 hour at room temperature. Following three washing steps with blocking buffer, the appropriate secondary antibody is applied (AlexaFluor 488 anti-rabbit immunoglobulin, 1:1000; Molecular Probes) for 1 hour at room temperature. After three washing steps, the cells can be fixed in Vectashield medium and the immunofluorescence visualized.

GLP-1 RNA isolated from cells can be assayed using RT-PCR. RT-PCR RNA isolation from cells can be performed using standard methodology. The RT-PCR reaction can be performed in a volume of 50 pl in a Peltier thermal cycler (PTC-225 DNA Engine Tetrad Cycler; MJ Research), using published primer sequences (Integrated DNA Technologies). Reverse transcription can be performed at 50° C. for 30 minutes; after an initial activation step at 95° C. for 15 minutes. PCR can be performed by denaturing at 94° C. for 1 minute, annealing at 55° C. for 1 minute and extension at 72° C. for 1 minute for 40 cycles, followed by a final extension step at 72° C. for 10 minutes. Negative controls can be included as appropriate, for example, by substituting water for the omitted reverse transcriptase or template. The control can be RNA isolated from, e.g., rat lingual epithelium. PCR products can be separated in 2% agarose gel with ethidium bromide, and visualized under UV light.

Radioimmunoassay (RIA) for total GLP-1 in patient blood samples can be performed as described in the art, e.g., by Laferrere, et al., 2007, "Incretin Levels and Effect are Markedly Enhanced 1 Month after Roux-en-Y Gastric Bypass Surgery in Obese Patients with Type 2 Diabetes, Diabetes Care 30(7):1709-1716 (using commercially available materials obtained from Phoenix Pharmaceutical, Belmont, Calif.). The authors describe measuring the effect of GIP and GLP-1 on secretion of insulin by measuring the difference in insulin secretion (area under the curve, or AUC) in response to an oral glucose tolerance test and to an isoglycemic intravenous glucose test.

Measurement of plasma concentrations of GLP-1, GIP, glucagon, insulin, C peptide, pancreatic peptide, nonesterified fatty acids, glutamic acid decarboxylase antibodies, and islet antigen antibodies, is described, e.g., by Toft-Nielsen, et al., 2001, "Determinants of the Impaired Secretion of Glucagon-Like Peptide-1 in Type 2 Diabetic Patients," J. Clin. End. Met. 86(8):3717-3723. The authors describe the use of radioimmunoassay for GLP-1 to measure plasma concentrations of amidated GLP-1-(7-36), using antibody code no. 89390. This assay measures the sum of GLP-1-(7-36) and its metabolite GLP-1-(9-36). The authors describe measurement of GIP using C-terminally directed antibody code no. R65 (RIA), that reacts 100% with a human GIP but not with 8-kDA GIP.

GLP-1 and PYY can be directly assayed in the supernatant from venous effluents as described by, e.g., Claustre, et al. (1999, "Stimulatory effect of (3-adrenergic agonists on ileal L cell secretion and modulation by a-adrenergic activation, J. Endocrin. 162:271-8). (See also Plaisancic' et al., 1994, "Regulation of glucagon-like peptide-1-(7-36) amide secretion by intestinal neurotransmitters and hormones in the isolated vascularly perfused rat colon," Endocrinology 135:2398-2403 and Plaisancie et al., 1995, "Release of peptide YY by neurotransmitters and gut hormones in the isolated, vascularly perfused rat colon," Scandinavian Journal of Gastroenterology 30:568-574.) In this method, the 199D anti-GLP-1 antibody is used at a 1:250 000 dilution. This antibody reacts 100% with GLP-1-(7-36) amide, 84% with GLP-1-(1-36) amide, and less than 0.1% with GLP-1-(1-37), GLP-1-(7-37), GLP-2, and glucagon. PYY is assayed with the A4D anti-porcine PYY antiserum at a 1:800 000 dilution.

Methods for assaying GLP-1 and GIP are also described elsewhere in the art, e.g., by Jong, et al., PNAS, 2007.

PYY can also be assayed in blood using a radioimmunoassay as described by, e.g., Weickert, et al., 2006, "Soy isoflavones increase preprandial peptide YY (PYY), but have no effect on ghrelin and body weight in healthy postmenopausal women" Journal of Negative Results in BioMedicine, 5:11. Blood is collected in ice-chilled EDTA tubes for the analysis of glucose, ghrelin, and PYY. Following centrifugation at 1600 g for 10 minutes at 4° C., aliquots were immediately frozen at −20° C. until assayed. All samples from individual patients were measured in the same assay. The authors described measuring immunoreactive total ghrelin was measured by a commercially available radioimmunoassay (Phoenix Pharmaceuticals, Mountain View, Calif., USA). (See also Weickert, et al., 2006, "Cereal fiber improves whole-body insulin sensitivity in overweight and obese women," Diabetes Care 29:775-780) Immunoreactive total human PYY is measured by a commercially available radioimmunoassay (LINCO Research, Missouri, USA), using 125I-labeled bioactive PYY as tracer and a PYY antiserum to determine the level of active PYY by the double antibody/PEG technique. The PYY antibody is raised in guinea pigs and recognizes both the PYY 1-36 and PYY 3-36 (active) forms of human PYY.

SGLT-1, the intestinal sodium-dependent glucose transporter 1, is a protein involved in providing glucose to the body. It has been reported to be expressed in response to sugar in the lumen of the gut, through a pathway involving T1R3 (Margolskee, et al., 2007 "T1R3 and gustducin in gut sense sugars to regulate expression of Na+-glucose cotransporter 1," Proc Natl Acad Sci USA 104, 15075-15080"). Expression of SGLT-1 can be detected as described, e.g., by Margolskee, et al., for example, using quantitative PCR and Western Blotting methods known in the art. Measurement of glucose transport has been described in the literature, e.g., by Dyer, et al., 1997, Gut 41:56-9 and Dyer, et al., 2003, Eur. J. Biochem 270:3377-88. Measurement of glucose transport in brush border membrane vesicles can be made, e.g., by initiating D-glucose uptake by the addition of 100 pl of incubation medium containing 100 mM NaSCN (or KSCN), 100 mM mannitol, 20 mM Hepes/Tris (pH 7.4), 0.1 mM MgSO4, 0.02% (wt/vol) NaN3, and 0.1 mM D-[U14C] glucose to BBMV (100 μg of protein). The reaction is stopped after 3 sec by addition of 1 ml of ice-cold stop buffer, containing 150 mM KSCN, 20 mM Hepes/Tris (pH 7.4), 0.1 mM MgSO4, 0.02% (wt/vol) NaN3, and 0.1 mM phlorizin. A 0.9-ml portion of the reaction mixture is removed and filtered under vacuum through a 0.22-[tm pore cellulose acetate/nitrate filter (GSTF02500; Millipore, Bedford, Mass.). The filter is washed five times with 1 ml of stop buffer, and the radioactivity retained on the filter is measured by liquid scintillation counting.

EXAMPLES

Example 1

Enteroendocrine Production of PYY, GLP-1 (Active) and GLP-1 (Total) and Reduction of Glucose and Insulin is Independent of Plasma Absorption of Metformin

Example 1.1

Materials and Methods

Population: Approximately 18 eligible male and female subjects, 18 to 65 years of age, with a BMI of 25.0 to 35.0 kg/m$^2$, were randomized in this study. To be eligible, each subject also met the following criteria: (a) was not breast-feeding; (b) had a negative pregnancy test result (human chorionic gonadotropin, beta subunit); (c) surgically sterile, postmenopausal, or if of childbearing potential, practiced appropriate birth control during the entire duration of the study; (d) had a physical examination with no clinically significant abnormalities, including but not limited to the following conditions: (i) Hepatic disease; (ii) Renal disease; (iii) gastrointestinal disease; (iv) Endocrine disorder, including diabetes; (v) Cardiovascular disease; (vi) Seizure disorder; (vii) Organ transplantation; and (viii) Chronic infection; and (e) an ability to understand and willingness to adhere to protocol requirements.

Formulations

The metformin DR formulation was a US-supplied commercially available film-coated immediate-release tablet containing 500 mg metformin hydrochloride, to which additional coatings (a seal coating and an enteric coating) were applied in order to delay release of the drug in the GI tract until the tablet reached a pH 6.5 region of the distal small intestine. The tablets were white, biconvex, circular-shaped coated tablets, each containing 500 mg metformin hydrochloride. Inactive ingredients in the commercially available tablet included povidone, magnesium stearate, hypromellose, and polyethylene glycol. Inactive ingredients in the additional coating systems included hypromellose, triacetin, talc, methacrylic acid copolymer (Eudragit® L30 D-55), poly(methyl acrylate-co-methyl methacrylate-co-methacrylic acid) 7:3:1 (Eudragit® FS 30 D), sodium lauryl sulfate, polysorbate 80, glyceryl monostearate, and triethyl citrate.

The metformin IR formulation was the identical US-supplied commercially available film-coated immediate-release tablet containing 500 mg metformin hydrochloride, to which only the additional seal coating is applied. No delayed-release (enteric) coating was applied. Inactive ingredients in the additional seal coating system included hypromellose, triacetin and talc.

The metformin formulations were supplied to the site as bulk tablets packaged in screw cap containers labeled with container number and lot number. All study medications were stored in cool and dry conditions as indicated on the label, and used only as directed by study personnel. Study medication was dispensed by the unblinded site pharmacist or study personnel according to the randomization scheme at the beginning of each treatment period.

Administration

Study medication was dispensed by an unblinded site pharmacist or study personnel according a randomization scheme at Visits 2 and 4. At the end of Visits 2 and 4, subjects were discharged from the clinic with assigned study medications and with instructions for self-administration until they returned for their next study visit (Visit 3 or 5).

Study medication was administered orally as intact tablets (swallowed whole, not chewed or crushed), and with water. The first dose and the last two doses of study medication for each treatment period were administered to subjects by qualified study site personnel (first dose at Visits 2 and 4 and last two doses at Visits 3 and 5). Subjects self-administered the assigned study medications according to instructions until they returned for their next study visit (Visit 3 or 5). Study site personnel contacted subjects by telephone on the second day of dosing of each treatment period to assess compliance and adverse events through non-directed questioning. If the subject was experiencing significant gastrointestinal symptoms, at the investigator's discretion, subjects were instructed not to dose escalate.

The procedures performed during the study are listed in Tables 1-3 below.

TABLE 1

Study Plan (Protocol LCPOC6)

| Evaluation | Screen | Treatment Period 1 | | | Treatment Period 2 | | | Early Termination |
|---|---|---|---|---|---|---|---|---|
| | | Baseline of Period 1 Visit 2 | Day 2 of Treatment Period Phone Call [1] | End of Period 1 Visit 3 | Baseline of Period 2 Visit 4 | Day 2 of Treatment Period Phone Call [1] | End of Period 2/ Study Termination Visit 5 | |
| Fast (>8 Hours Overnight) | X | X | | X | X | | X | |
| Informed Consent | X | | | | | | | |
| Complete Medical History | X | | | | | | | |
| Physical Examination and Height | X | | | | | | | |
| Body Weight and Vital Signs | X | X | | X | X | | X | X |
| Chemistry, Hematology, Urinalysis | X | | | | | | X | X |
| Pregnancy Test (Females) [2] | X | | | | | | X | X |
| Randomization | | X | | | | | | |
| Timed Blood Sampling [3] | | X | | X | X | | X | |
| Study Medication Administration [4] | | X | | X | X | | X | |
| Dispense Study Medication | | X | | | X | | | |
| Study Medication Compliance Assessment and Collection | | | | X | | | X | |

TABLE 1-continued

Study Plan (Protocol LCPOC6)

|  |  | Treatment Period 1 | | | Treatment Period 2 | | | |
| --- | --- | --- | --- | --- | --- | --- | --- | --- |
| Evaluation | Screen | Baseline of Period 1 Visit 2 | Day 2 of Treatment Period Phone Call [1] | End of Period 1 Visit 3 | Baseline of Period 2 Visit 4 | Day 2 of Treatment Period Phone Call [1] | End of Period 2/ Study Termination Visit 5 | Early Termination |
| Dose Escalation Phone Call |  |  | X |  |  | X |  |  |
| Concomitant Medications Assessment | X | X |  | X | X |  | X | X |

[1] Phone calls to assess compliance and adverse events through non-directed questioning and to remind subjects to dose escalate
[2] Pregnancy test required on all female subjects unless subject has had a hysterectomy or is postmenopausal.
[3] GLP-1, PYY, plasma glucose, insulin, and triglycerides at Visits 2 and 4; GLP-1, PYY, plasma glucose, insulin, triglycerides and metformin at Visits 3 and 5. After meal challenge at Visit 2 and Visit 4. Evening dose on Day 4 and morning dose on Day 5 at Visit 3 and Visit 5.

TABLE 2

Schedule of Standardized Breakfast and Blood Sampling Profile at Visit 2 and Visit 4

| Time (minutes) | Collect 6-mL blood samples [1] | Standardized Breakfast Administration [2] |
| --- | --- | --- |
| −15 | X |  |
| −5 | X |  |
| 0 |  | X |
| 30 | X |  |
| 45 | X |  |
| 60 | X |  |
| 90 | X |  |
| 120 | X |  |
| 150 | X |  |
| 180 | X |  |
| 210 | X |  |
| 240 | X |  |
| 270 | X |  |
| 300 | X |  |
| 330 | X |  |

[1] 6-mL blood volume total per sampling time point for assessment of PYY, GLP-1, plasma glucose, insulin, and triglycerides.
[2] Subjects are to be instructed to consume the standardized breakfast within 20 minutes.

TABLE 3

Day 5 Schedule of Dosing, Standardized Breakfast and Blood Sampling Profile at Visit 3 and Visit 5

| Time (minutes) | Collect 6-mL blood samples [1] | Standardized Breakfast Administration [2] | Collect Dose Study Medication | 2-mL blood sample [3] |
| --- | --- | --- | --- | --- |
| −245 |  |  |  | X |
| −240 |  | X |  |  |
| −120 |  |  |  | X |
| −15 | X |  |  |  |
| −5 | X |  |  | X |
| 0 |  | X |  |  |
| 30 | X |  |  | X |
| 45 | X |  |  | X |
| 60 | X |  |  | X |
| 90 | X |  |  | X |
| 120 | X |  |  | X |
| 150 | X |  |  | X |
| 180 | X |  |  | X |
| 210 | X |  |  | X |
| 240 | X |  |  | X |
| 270 | X |  |  | X |
| 300 | X |  |  | X |
| 330 | X |  |  | X |
| 360 |  |  |  | X |
| 420 |  |  |  | X |
| 480 |  |  |  | X |

[1] 6-mL blood volume total per sampling time point for assessment of PYY, GLP-1, plasma glucose, insulin, and triglycerides.
[2] Subjects are to be instructed to consume the standardized breakfast within 20 minutes.
[3] 2-mL blood volume total per sampling time point for assessment of metformin.

Pharmacodynamic Assessments

Blood samples were collected according to the schedules presented in Tables 1, 2, and 3, and as described above. Fasting and postprandial plasma concentrations of gut hormones GLP-1 and PYY, as well as concentrations of plasma glucose, insulin, and triglycerides were measured by analytical methods. Blood samples from each visit was processed and stored at −70° C. for future exploratory analysis of additional hormones.

Pharmacokinetic Assessments

Blood samples were collected according to the schedules presented in Tables 1, 2, and 3, and as described above. Plasma metformin concentrations were measured by analytical methods. Blood samples from each visit were processed and stored at −70° C. for future exploratory analysis of additional hormones.

Clinical Laboratory Evaluations

Samples were collected according to the schedules presented in Tables 1, 2 and 3, and in the preceding section.

Chemistry

Chemistry assessments included the following: urea nitrogen, creatinine, total protein, albumin, uric acid, total bilirubin, alkaline phosphatase, alanine aminotransferase, aspartate aminotransferase, gamma glutamyltranspeptidase, creatine phosphokinase, glucose, sodium, potassium, chloride, bicarbonate, phosphorus, lactate, and calcium (or other approved routine chemistry panels.

Hematology

Hematology assessments included the following: red cell count, hemoglobin, hematocrit, white cell count, platelets, differential count, mean cell volume, mean corpuscular hemoglobin, and mean corpuscular hemoglobin concentration (or other approved routine hematology assessments).

Urinalysis

Urinalysis assessments included the following: pH, specific gravity, glucose, blood, ketones, and protein (or other approved routine urinalysis).

Pregnancy Testing

All female subjects, regardless of childbearing status (unless subject was postmenopausal or had a hysterectomy), provided blood or urine for pregnancy tests. Study medication was not administered unless a negative result was obtained.

Vital Signs and Other Observations Related to Safety

Clinically significant abnormalities in vital signs and other observations related to safety were followed up by the investigator and evaluated with additional tests if necessary, until the underlying cause was diagnosed or resolution occurred.

Vital Signs

Vital sign measurements included sitting systolic and diastolic blood pressure, heart rate, and body temperature. Vital signs were measured after the subject rested for approximately 5 minutes and with the subject in a sitting position. The blood pressure measurement was repeated after at least 30 seconds and the average of the two readings recorded.

Example 1.2

Results

Figure 2:
FIG. 2 shows the events during the treatment period of the study described in Example 1.
Figure 2:

The study design and event timeline are shown in FIGS. 1-2. Shown in Tables 4 and 5 below are the resulting subject disposition and population (Table 4) and the demographic and baseline characteristics of 18 subjects (Table 5).

TABLE 4

Subject Disposition and Population

| Parameter | Result |
| --- | --- |
| Randomized | 18 |
| Completed | 17 |
| Withdrawal (positive drug test) | 1 |
| Evaluable Population | 16 |

2 subjects excluded from evaluable population; 1 withdrawn and 1 could not complete test meal at end of Treatment Period 2

TABLE 5

Demographic and Baseline Characteristics (n = 18)

| Parameter | Result |
| --- | --- |
| Gender (M/F) | 9/9 |
| Mean Age (yr) ± SD | 44 ± 10 |
| Race | 9 Caucasian, 7 Hispanic, 2 black |
| Mean BMI (kg/m2) ± SD | 29.3 ± 2.8 |

Figure 3:
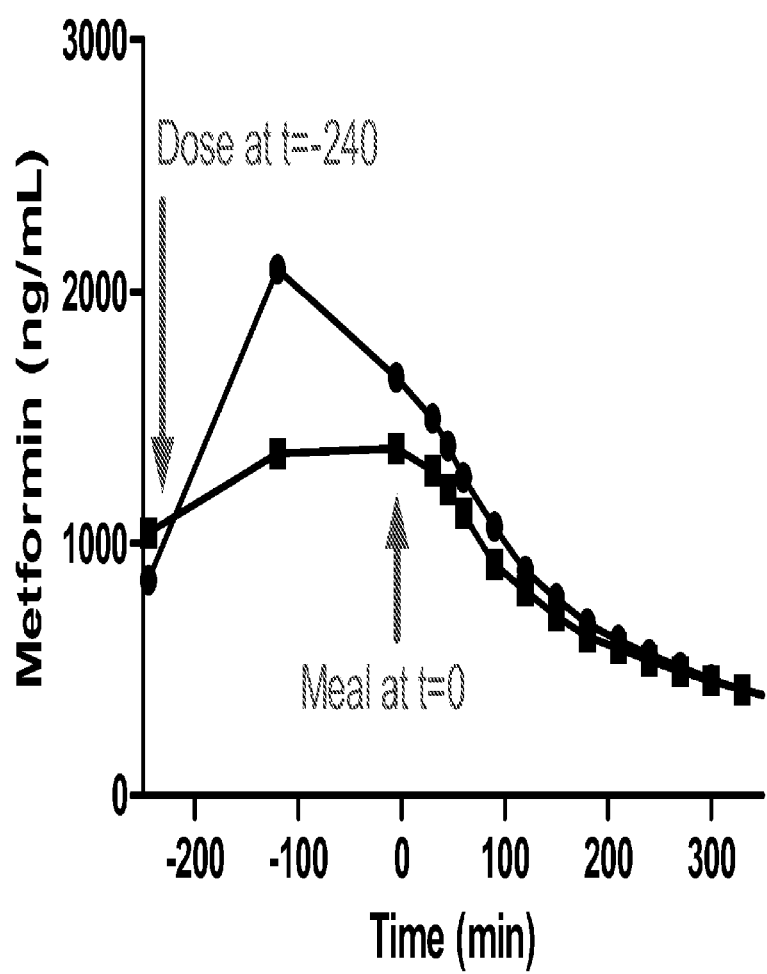
FIG. 3 shows the plasma concentration of metformin immediate-release (Metformin IR) (●) and metformin delayed-release (Metformin DR) (■) (x-axis; ng/mL) as a function of time (y-axis; min) after ingestion at t=−240 and after a meal at t=0 min.

FIG. 3 demonstrates that ingestion of Metformin DR minimized adsorption of metformin in the plasma compared to Metformin TR. The area under the curve (AUC) and Cmax values for Metformin DR and Metformin TR are provided in Table 6 below.

TABLE 6

Metformin Plasma Pharmacokinetics

| | LS Mean Ratio ReMet/Metformin | P Value |
| --- | --- | --- |
| Abs AUC | 0.83 | 0.02 |
| Abs Cmax | 0.73 | 0.003 |
| Incremental Cmax | 0.45 | <0.001 |

Figure 4A:
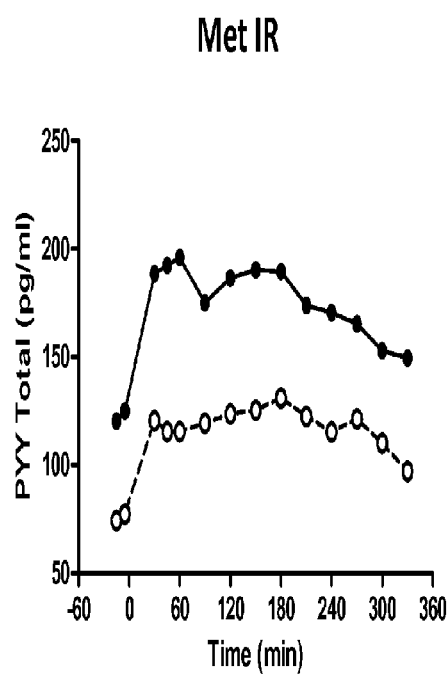
FIG. 4A shows the plasma concentration of PYY (x-axis; pg/mL) as a function of time (y-axis; min) in subjects at baseline (□,○) or after ingestion of either Metformin IR (●) or Metformin DR (■) and after a meal at t=0 min.
Figure 4A:
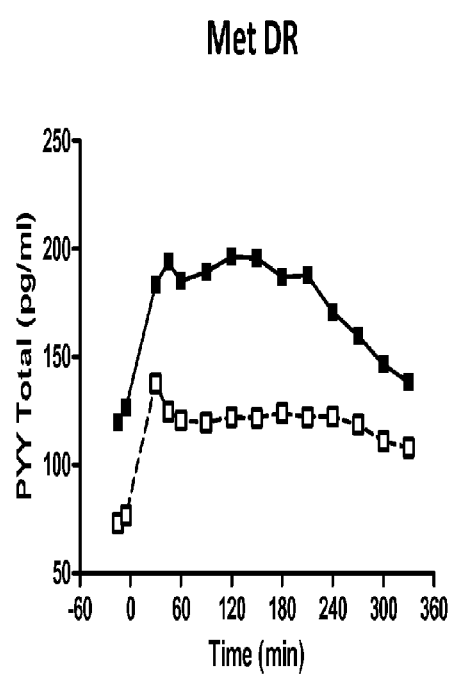
Figure 4B:
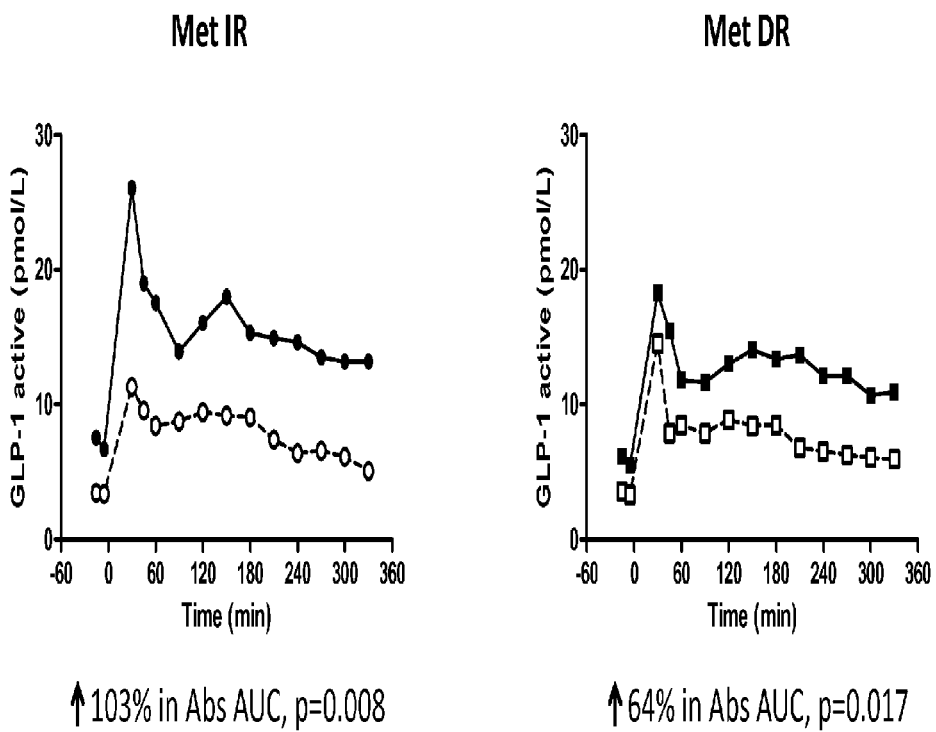
FIG. 4B shows the plasma concentration of active GLP-1 (x-axis; GLP-1A pmol/L) as a function of time (y-axis; min) in subjects at baseline (□,○) or after ingestion of either Metformin IR (●) or Metformin DR (■) and after a meal at t=0 min.
Figure 4C:
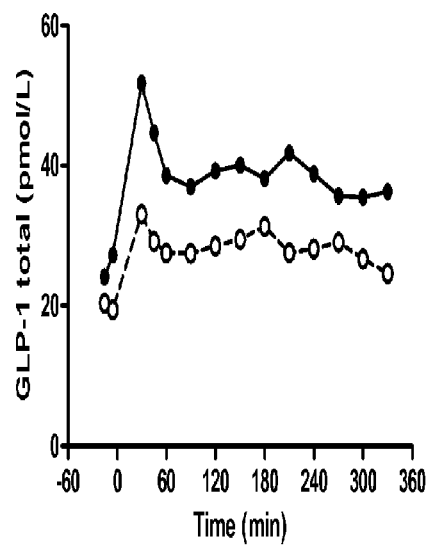
FIG. 4C shows the plasma concentration of total GLP-1 (x-axis; GLP-1T pmol/L) as a function of time (y-axis; min) in subjects at baseline (□,○) or after ingestion of either Metformin IR (●) or Metformin DR (■) and after a meal at t=0 min. For FIGS. 4A-4C, percent increase in Abs AUC is compared to baseline values.
Figure 4C:
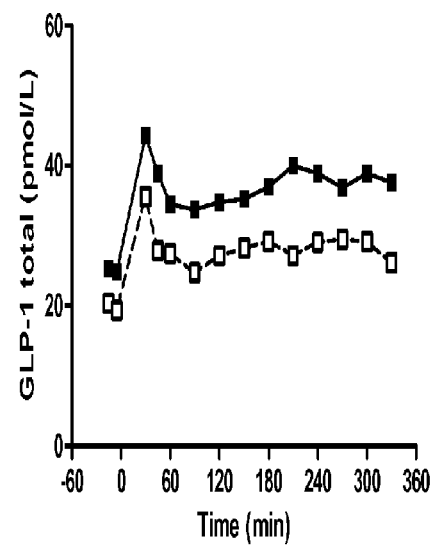
Figure 5A:
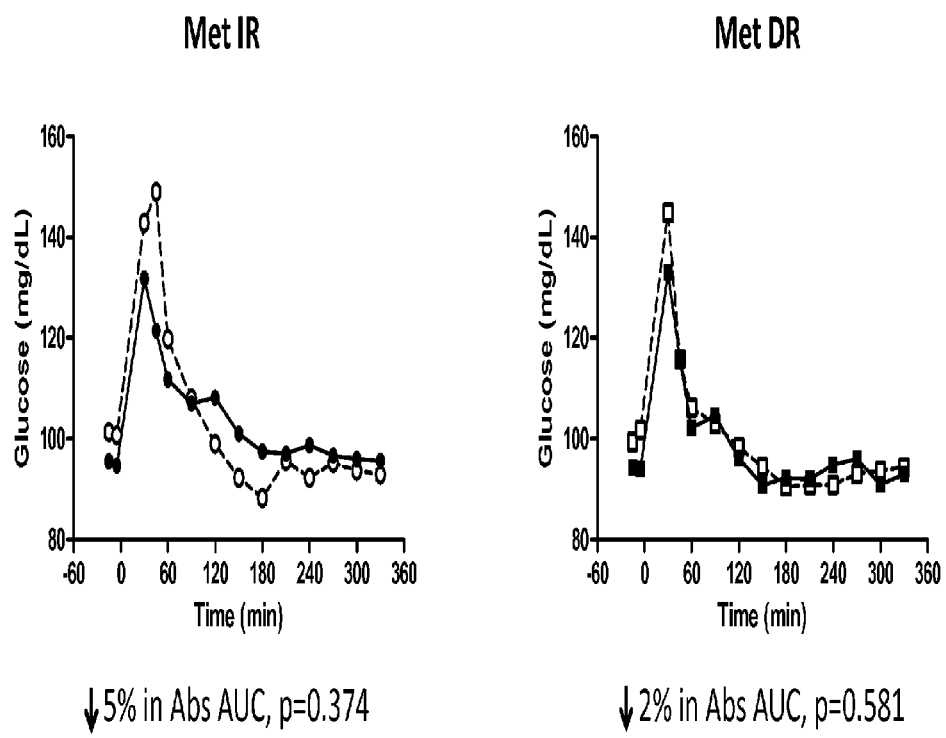
FIG. 5A shows the plasma concentration of glucose (x-axis; mg/dL) as a function of time (y-axis; min) in subjects at baseline (□,○) or after ingestion of either Metformin IR (●) or Metformin DR (■) and after a meal at t=0 min.
Figure 5B:
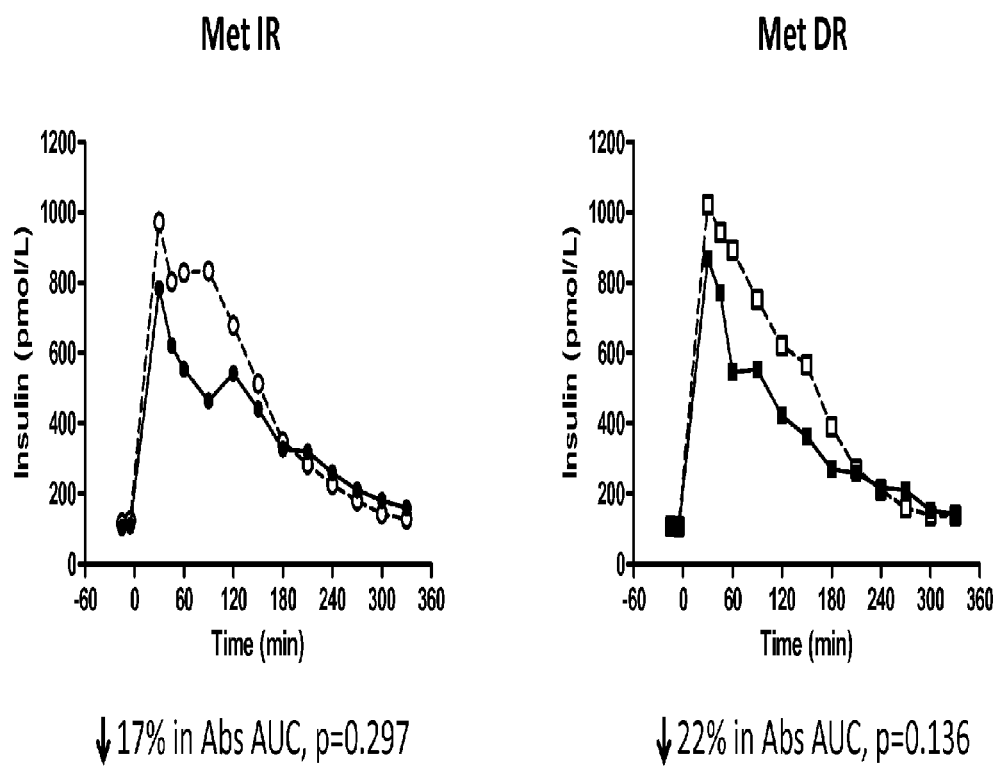
FIG. 5B shows the plasma concentration of insulin (x-axis; pmol/L) as a function of time (y-axis; min) in subjects at baseline (□,○) or after ingestion of either Metformin IR (●) or Metformin DR (■) and after a meal at t=0 min. For FIGS. 5A-5B, percent decrease in Abs AUC is compared to baseline values.
Figure 6:
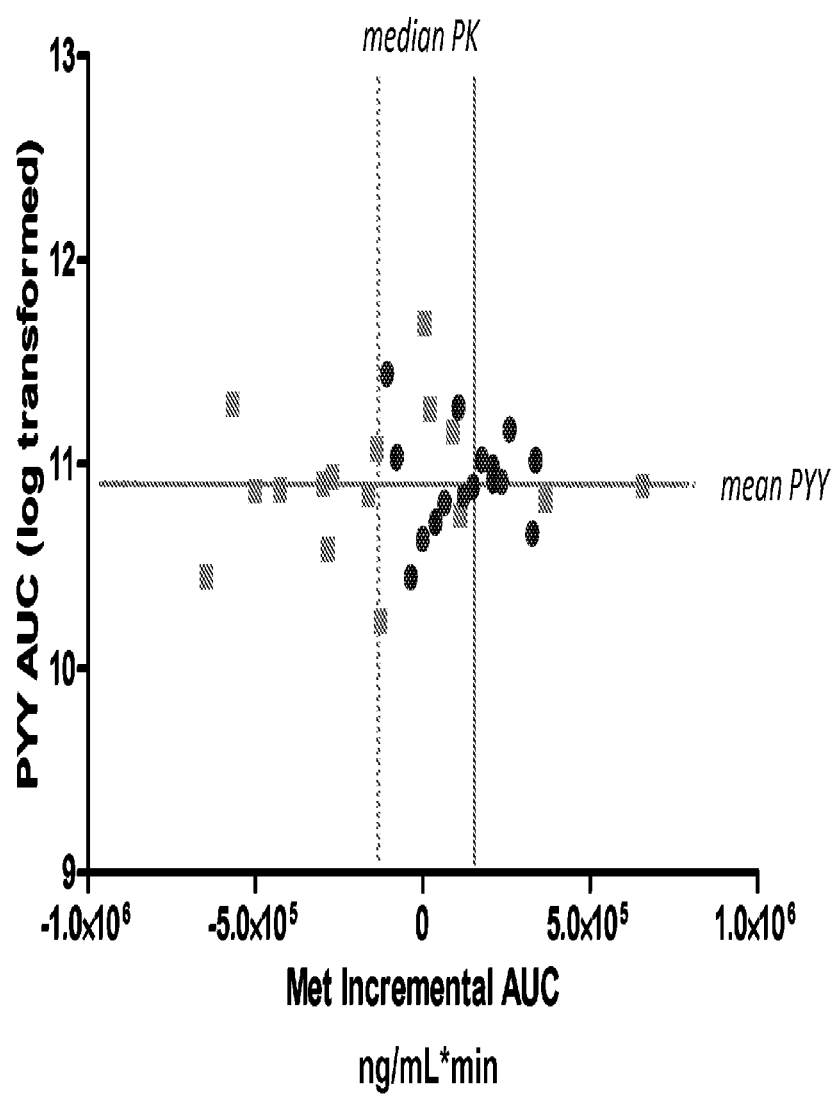
FIG. 6 is a graph that shows the area under the curve of PYY (x-axis; log transformed) as a function of the area under the curve of metformin (ng/mL*min) after ingestion of Metformin IR (●) and Metformin DR (■).

FIG. 4A-C shows an increase in meal-enhanced gut hormones in 16 subjects after treatment of Metformin DR comparable to that of Metformin IR, although treatment with Metformin DR minimized the systemic level of metformin compared to Metformin IR (FIG. 3). Additionally, FIGS. 5A-B show a reduction in meal-enhanced glucose and insulin after treatment with Metformin DR in 16 subjects comparable to that of Metformin IR. FIG. 6 shows that treatment with Metformin DR results in a similar PYY response as Metformin IR, but has a lower systemic exposure. FIGS. 7A-B show that the metformin PK/PD relationship was dissociable in at least one patient.

Example 2

A Randomized Crossover Study to Assess Steady-State PK and PD of Delayed-Release and Immediate Release Metformin in Subjects with Type 2 Diabetes Mellitus This randomized, crossover study assessed the steady-state pharmacokinetics and pharmacodynamics (glucose, insulin, glucagon-like peptide-1 [GLP-1], and peptide YY [PYY], of 500 mg and 1000 mg metformin delayed-release (Metformin DR), 1000 mg metformin immediate-release (Metformin IR), and 500 mg Metformin IR+1000 mg Metformin DR in subjects with type 2 diabetics mellitus. Subjects managing their diabetes with oral anti-diabetic therapy must have been off of those medications for at least the fourteen days immediately prior to randomization.

Each treatment period was five days long and separated by washout intervals of seven days. Each treatment period contained a standardized breakfast and lunch profile on Day 1 prior to administration of study drug (baseline assessment) and an identical profile on the morning of Day 5 (on-drug assessment).

Example 2.1

Materials and Methods

Subjects were evaluated for the effects of each treatment on circulating PYY, GLP-1, glucose, and insulin concentrations over approximately 10 hours in response to two standardized meals (~500 kcal standardized breakfast at t=0 min, and ~1000 kcal standardized lunch at t=300 min) using standard protocols. Metformin pharmacokinetics over an approximately 11-hour sampling period were also evaluated.

Population: Most randomized subjects were White (79.2%), and half were female (50.0%). The mean age was 51.3 years, the mean weight was 93.4 kg, and the mean BMI was 33.3 kg/m² at baseline. Nineteen of the 24 subjects completed the study.

The primary population for pharmacokinetic and pharmacodynamic analyses was the Evaluable Population (N=19), defined as all subjects who completed all treatment periods consistent with protocol procedures. The primary population for safety analyses was the Intent-to-Treat (ITT) Population (N=24), defined as all subjects who received at least one dose of study medication.

Formulations

The metformin DR formulation was a US-supplied commercially available film-coated immediate-release tablet containing 500 mg metformin hydrochloride, to which additional coatings (a seal coating and an enteric coating) were applied in order to delay release of the drug in the GI tract until the tablet reaches a pH 6.5 region of the distal small intestine. The tablets are white, biconvex, circular-shaped coated tablets, each containing 500 mg metformin hydrochloride. Inactive ingredients in the commercially available tablet included povidone, magnesium stearate, hypromellose, and polyethylene glycol. Inactive ingredients in the additional Elcelyx coating systems included hypromellose, triacetin, talc, methacrylic acid copolymer (Eudragit® L30 D-55), poly(methyl acrylate-co-methyl methacrylate-co-methacrylic acid) 7:3:1 (Eudragit® FS 30 D), sodium lauryl sulfate, polysorbate 80, glyceryl monostearate, and triethyl citrate.

The metformin IR formulation was the identical US-supplied commercially available film-coated immediate-release tablet containing 500 mg metformin hydrochloride, to which only the additional seal coating is applied. No delayed-release (enteric) coating was applied. Inactive ingredients in the additional seal coating system included hypromellose, triacetin and talc.

The metformin formulations were supplied to the site as bulk tablets packaged in screw cap containers labeled with container number and lot number. All study medications were stored in cool and dry conditions as indicated on the label, and used only as directed by study personnel. Study medication was dispensed by the unblinded site pharmacist or study personnel according to the randomization scheme at the beginning of each treatment period.

Administration

Study medication was administered orally as intact tablets (swallowed whole) with water at the beginning of the breakfast and dinner meals. Subjects self-administered their assigned study medications on the evening of Day 1 through the morning of Day 4 according to instructions provided on Day 1 by the study site staff. The last two doses of study medication for each treatment period (evening of Day 4 and morning of Day 5) were administered to subjects by qualified study site personnel. In order to reduce gastrointestinal side effects, all treatment regimens initiated treatment at 500 mg/dose for the first 3 doses, followed by an increase to the randomized dose (500 mg/dose, 1000 mg, or 1500 mg/dose) for the remainder of the study period. Study site personnel contacted subjects by telephone on the second day of dosing of each treatment period to assess compliance and adverse events through non-directed questioning and to remind them to dose-escalate if appropriate.

Example 2.2

Results

Pharmacokinetic Evaluations

Pharmacokinetic Profiles

Figure 8:
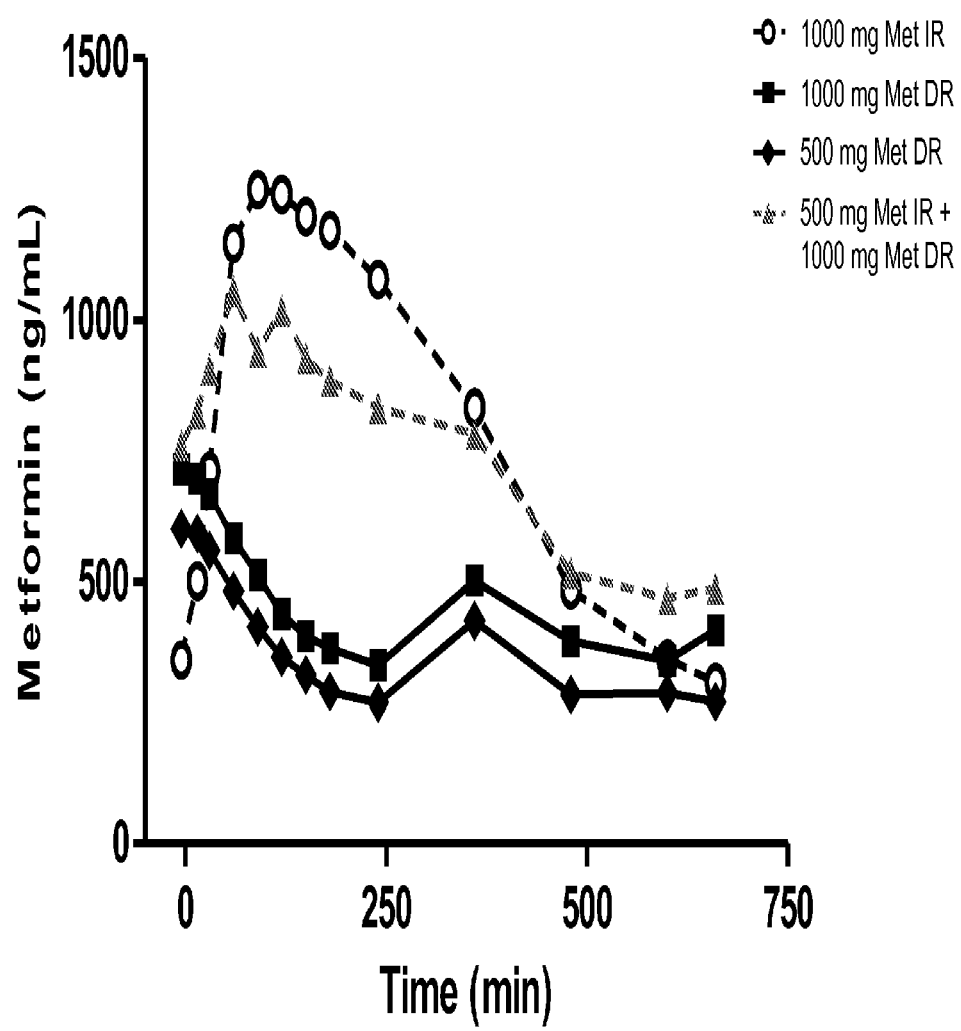
FIG. 8 shows the mean plasma metformin concentrations (x-axis; ng/mL) at Day 5 of 500 mg (♦) and 1000 mg (●) Metformin DR, 1000 mg Metformin IR (○), and 500 mg Metformin IR+1000 mg Metformin DR (▲) as a function of time (y-axis; min). Dose was administered at t=−1 minute.

FIG. 8 presents the mean plasma metformin concentrations at Day 5 by treatment and time point. On Day 5, the pre-dose mean concentration of Metformin IR at t=0 was 350 ng/mL, which is consistent with steady-state trough concentrations published in the literature. After the administration of Metformin IR at t=−1 minute, there was a rapid increase in metformin concentrations that peaked at 1249 ng/mL 90 min after the dose followed by a steady decline for the remainder of the sampling period.

The pre-dose concentrations for both doses of Metformin DR were approximately 2 times higher than those for Metformin IR (716 ng/mL for 1000 mg DR and 602 ng/mL for 500 ng/mL DR vs. 350 ng/dL for 1000 mg IR). Following the administration of both doses of metformin DR at t=−1 minute, there was a decrease in metformin concentrations for the first 240 minutes followed by a small rise in metformin concentrations after the standardized lunch meal, which then plateaued for the remainder of the sampling period. The entire 11-hour metformin profiles remained below the pre-dose concentrations measured at t=0. The absorption profiles for Metformin DR dosing with the evening meal were slowed relative to doses administered with the breakfast meal, consistent with slowed intestinal transit during the sleeping hours. Metformin DR concentrations for the 500-mg dose were lower than the 1000-mg dose at all time points although the reductions were less than dose-proportional. This observation is consistent with the lack of dose-proportionality reported for Metformin IR and could be due to a saturable absorption process in the gut.

The Metformin DR+Metformin IR treatment group had the highest pre-dose concentrations of the four treatment groups (761 ng/mL) Following the administration of study medication at t=−1 minute, metformin concentrations rapidly rose in a manner similar to metformin IR but generally remained below the Metformin IR concentration curve for the first 500 minutes. For the remainder of the sampling period, concentrations plateaued but where higher than those observed with the other treatments.

Pharmacokinetic Parameters

Figure 9:
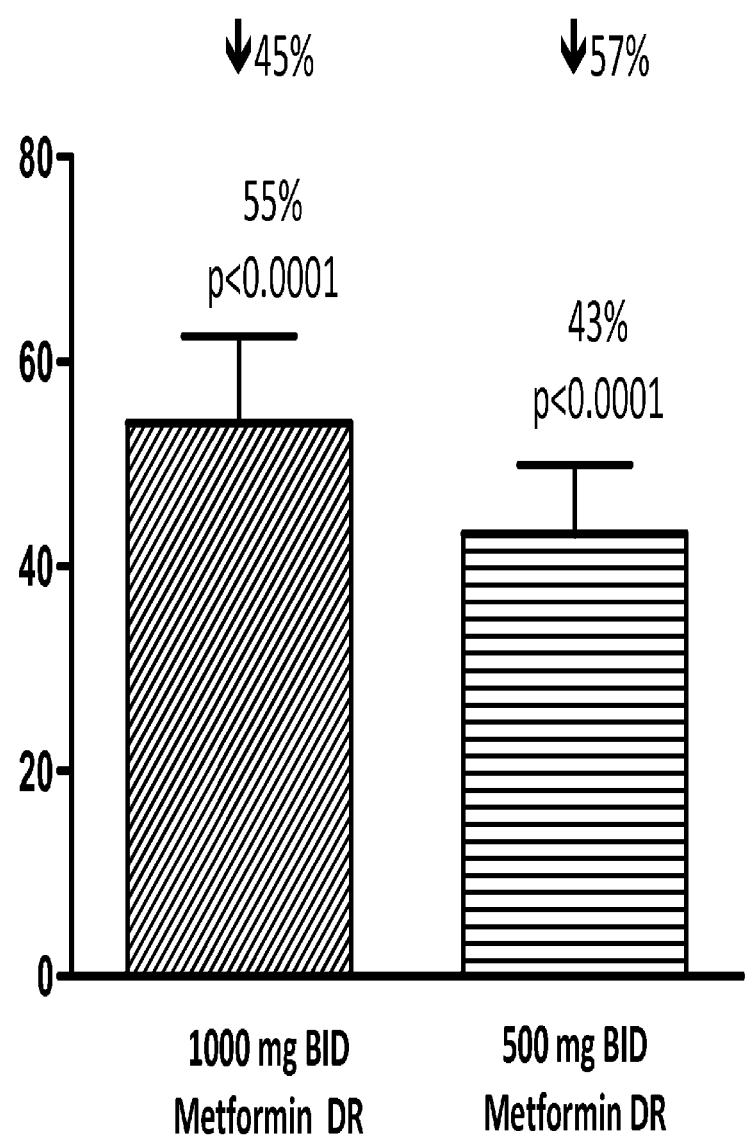
FIG. 9 shows the steady-state relative bioavailability in subjects with type 2 diabetes of 500 mg BID and 1000 mg BID of Metformin DR compared to 1000 mg BID of Metformin IR based on the 11 hour plasma metformin AUC on Day 5 (y-axis; % $AUC_{(0-11\ hr)}$). These levels constitute a 45% and 57% reduction in the overall plasma metformin extent of exposure for 500 mg BID and 1000 mg BID of Metformin DR compared to 1000 mg BID of Metformin IR.

Table 7 and FIG. 9 present the relative bioavailability of metformin by treatment versus Metformin IR at Day 5. Compared to the Metformin IR formulation the metformin exposure from t=0 to time of last concentration after study medication administration ($AUC_{0-t}$) was statistically significantly reduced by 45.2% with 1000 mg Metformin DR (% mean ratio of 54.8; p<0.0001) and 56.6% with 500 mg Metformin DR (% mean ratio of 43.4; p<0.0001). Compared to Metformin IR, $C_{max}$ was also was statistically significantly reduced by 34.9% with 1000 mg Metformin DR (% mean ratio of 65.1; p<0.0001) and 47.7% with 500 mg metformin DR (% mean ratio of 52.3; p<0.0001).

The Metformin DR+IR treatment resulted in exposures similar to that of the 1000 mg Metformin IR (% mean ratio of 90.9; p=0.2271) despite an increase in daily dose of 50%.

TABLE 7

Relative Bioavailability of Metformin by Treatment versus Metformin IR at Day 5 - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| $AUC_{0-t}$ (ng * h/mL) | | | | |
| Geometric LS mean | 8325 | 4559 | 3614 | 7567 |
| % ratio [1] | | | | |
| Geometric LS mean | NA | 54.8 | 43.4 | 90.9 |
| 90% CI | NA | 48.1, 62.4 | 38.1, 49.5 | 79.8, 103.6 |
| p value | NA | <0.0001 | <0.0001 | 0.2271 |
| $Cmax_{0-t}$ (ng/mL) | | | | |
| Geometric LS mean | 1283 | 836 | 671 | 1150 |
| % ratio [1] | | | | |
| Geometric LS mean | NA | 65.1 | 52.3 | 89.6 |
| 90% CI of % ratio | NA | 56.5, 75.0 | 45.4, 60.3 | 77.8, 103.3 |
| p value of % ratio | NA | <0.0001 | <0.0001 | 0.2016 |

Abbreviations:
NA = not applicable;
t = last quantifiable concentration following dose administration.
Note:
Intra subject CV % was 24.2 for $AUC_{0-t}$ and 26.3 for $C_{max}$.
[1] (1000 mg Met IR, 1000 mg Met DR, or 500 mg Met DR)/1000 mg Met IR.

Pharmacodynamic Evaluations
PYY Total

Figure 10:
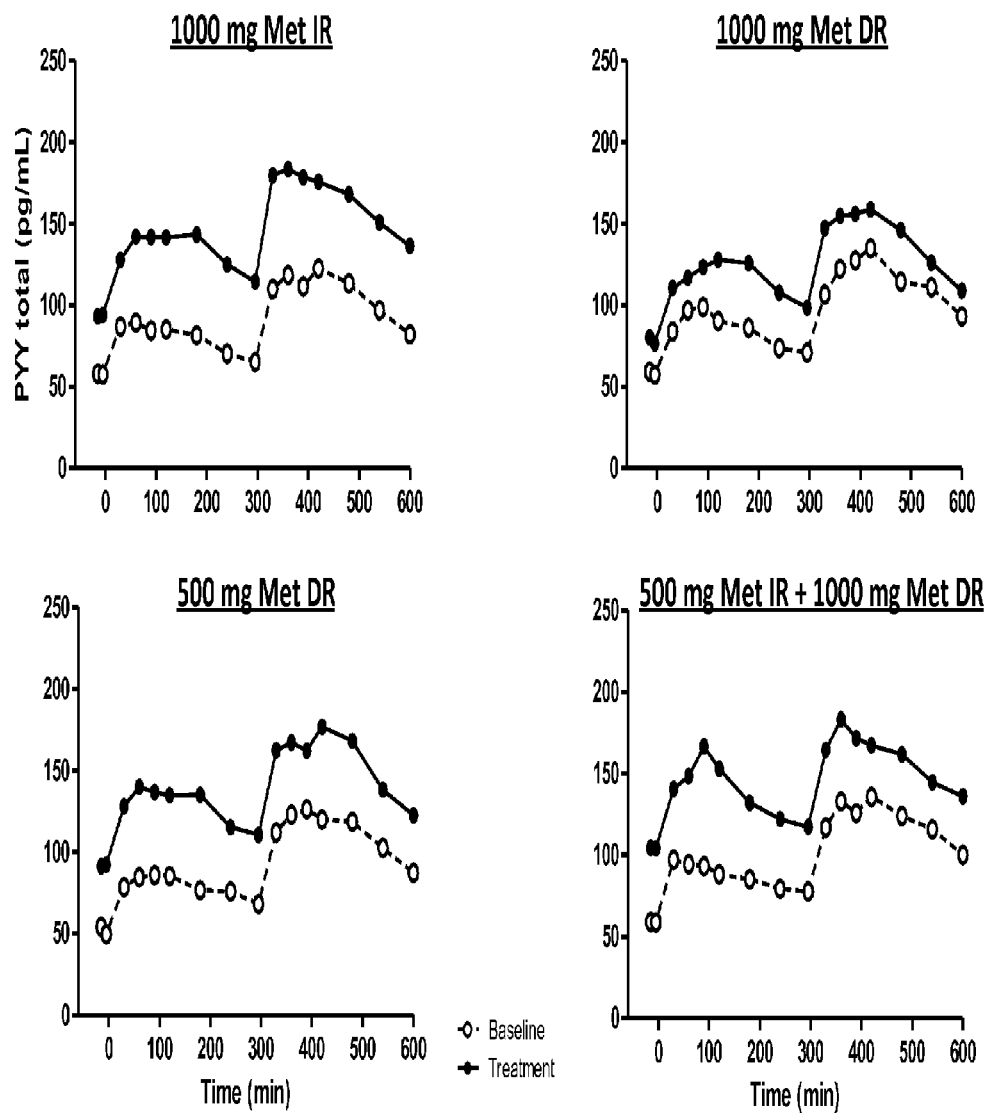
FIG. 10 shows the mean plasma PYY total concentrations (x-axis; pg/mL) as a function of time (y-axis; min) in subjects at baseline (○) or Day 5 of the designated treatment) (●).

FIG. 10 and Table 8 present the mean plasma PYY total concentration profiles at baseline and Day 5 by treatment and time point and the corresponding analysis of pharmacodynamic parameters, respectively. Baseline plasma PYY total concentrations were similar between treatments at most time points. Additionally, all metformin treatments statistically significantly increased PYY total exposure and peak concentrations (p<0.01 for all), with percent ratios (Day5/Day1) for $AUC_{0-t}$ and Cmax ranging from 1.26 to 1.55. Fasting plasma PYY total concentrations were also statistically significantly increased from baseline at Day 5 for each treatment (Table 9, p<0.01 for all). These results indicate that all of the treatments studied elicited similar PYY total responses to two standardized meals.

GLP-1 Active

Figure 11:
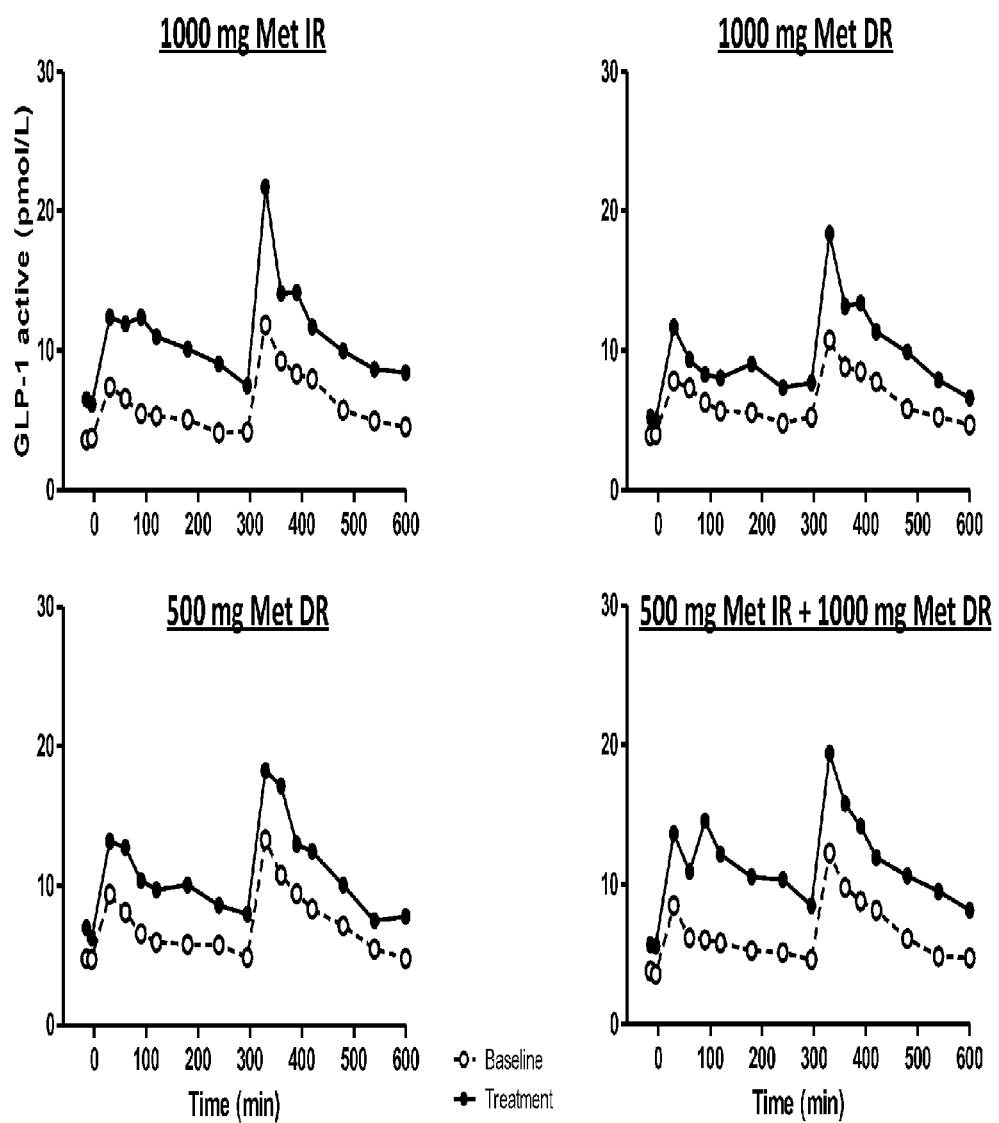
FIG. 11 shows the mean plasma GLP-1 active concentration (x-axis; pmol/L) as a function of time (y-axis; min) in subjects at baseline (○) or Day 5 of the designated treatment (●). Breakfast was administered at t=0 min, dose was administered at t=−1 minute, and lunch was administered at t=300 min.

FIG. 11 and Table 10 present the mean plasma GLP-1 active concentration profiles at baseline and Day 5 by treatment and time point and the corresponding analysis of pharmacodynamic parameters, respectively. Baseline plasma GLP-1 active concentrations were similar between treatments at most time points. Additionally, all metformin treatments statistically significantly increased GLP-1 active exposure and peak concentrations (p<0.01 for all), with percent ratios (Day5/Day1) for AUC0-t and Cmax ranging from 1.42 to 1.88. Fasting plasma GLP-1 total concentrations were also statistically significantly increased from baseline at Day 5 for each treatment (Table 11, p<0.05 for all). These results indicate that all of the treatments studied elicited similar GLP-1 active responses to two standardized meals.

TABLE 8

Pharmacodynamic Analysis of Plasma PYY Total (pg/mL) - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| $AUC_{0-t}$ (pg/mL * min) | | | | |
| BL geo. LS mean (SE) | 51487 (5104) | 51518 (5579) | 50932 (5587) | 51985 (5614) |
| EOT geo. LS mean (SE) | 79654 (7897) | 71218 (7712) | 74546 (8178) | 77270 (8344) |
| % ratio [1] | | | | |
| Geo. LS mean (SE) | 1.55 (0.09) | 1.38 (0.09) | 1.46 (0.06) | 1.49 (0.06) |
| 95% CI | 1.36, 1.75 | 1.22, 1.57 | 1.34, 1.59 | 1.36, 1.62 |
| p value | <0.0001 | <0.0001 | <0.0001 | <0.0001 |
| $Cmax_{0-t}$ (pg/mL) | | | | |
| BL geo. LS mean (SE) | 124 (13) | 135 (16) | 122 (13) | 129 (15) |
| EOT geo. LS mean (SE) | 190 (19) | 169 (20) | 169 (18) | 184 (21) |
| % ratio [1] | | | | |
| Geo. LS mean (SE) | 1.53 (0.10) | 1.26 (0.09) | 1.38 (0.08) | 1.43 (0.06) |
| 95% CI | 1.34, 1.75 | 1.08, 1.47 | 1.23, 1.55 | 1.31, 1.56 |
| p value | <0.0001 | 0.0056 | <0.0001 | <0.0001 |

Abbreviations:
BL = baseline (Day 1);
EOT = end of treatment (Day 5);
geo. = geometric;
t = last quantifiable concentration following dose administration.
[1] EOT (Day 5)/BL (Day 1) for each treatment

TABLE 9

Fasting Plasma PYY Total (pg/mL) at Baseline and Day 5 - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| BL LS mean (SE) | 59.47 (10.22) | 56.26 (8.32) | 53.39 (11.42) | 59.11 (12.90) |
| EOT LS mean (SE) | 94.75 (10.22) | 75.80 (8.32) | 91.13 (11.42) | 92.92 (12.90) |
| LS mean diff (SE) | 35.28 (6.64) | 19.53 (6.17) | 37.73 (10.41) | 33.81 (9.91) |
| 95% CI | 21.28, 49.28 | 6.51, 32.56 | 15.77, 59.69 | 12.90, 54.71 |
| p value | <.0001 | 0.0057 | 0.0021 | 0.0033 |

Abbreviations:
BL = baseline (Day 1);
EOT = end of treatment (Day 5).

TABLE 10

Pharmacodynamic Analysis of Plasma GLP-1 Active (pmol/L) - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| $AUC_{0-t}$ (pmol/L * min) | | | | |
| BL geo. LS mean (SE) | 3031 (386) | 3059 (405) | 3547 (447) | 3277 (380) |
| EOT geo. LS mean (SE) | 5655 (719) | 4953 (655) | 5993 (755) | 6158 (714) |
| % ratio [1] | | | | |
| Geo. LS mean (SE) | 1.87 (0.18) | 1.62 (0.11) | 1.69 (0.15) | 1.88 (0.19) |
| 95% CI | 1.52, 2.29 | 1.40, 1.87 | 1.41, 2.03 | 1.52, 2.33 |
| p value | <0.0001 | <0.0001 | <0.0001 | <0.0001 |
| $Cmax_{0-t}$ (pmol/L) | | | | |
| BL geo. LS mean (SE) | 11.3 (1.4) | 10.6 (1.3) | 13.9 (1.5) | 12.0 (1.3) |
| EOT geo. LS mean (SE) | 19.2 (2.3) | 17.3 (2.1) | 19.7 (2.1) | 21.1 (2.3) |
| % ratio [1] | | | | |
| Geo. LS mean (SE) | 1.70 (0.16) | 1.64 (0.17) | 1.42 (0.14) | 1.76 (0.19) |
| 95% CI | 1.40, 2.07 | 1.32, 2.03 | 1.15, 1.76 | 1.40, 2.21 |
| p value | <0.0001 | 0.0001 | 0.0025 | <0.0001 |

Abbreviations:
BL = baseline (Day 1);
EOT = end of treatment (Day 5);
geo. = geometric;
t = last quantifiable concentration following dose administration.
[1] EOT (Day 5)/BL (Day 1) for each treatment.

TABLE 11

Fasting Plasma GLP-1 Active (pmol/L) at Baseline and Day 5 - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| BL LS mean (SE) | 3.79 (1.16) | 3.93 (1.19) | 4.73 (1.31) | 3.69 (1.04) |
| EOT LS mean (SE) | 6.32 (1.16) | 5.10 (1.19) | 6.62 (1.31) | 5.64 (1.04) |
| LS mean diff (SE) | 2.53 (0.83) | 1.17 (0.54) | 1.89 (0.45) | 1.95 (0.91) |
| 95% CI | 0.80, 4.26 | 0.03, 2.31 | 0.96, 2.83 | 0.03, 3.87 |
| p value | 0.0067 | 0.0444 | 0.0005 | 0.0466 |

Abbreviations:
BL = baseline (Day 1);
EOT = end of treatment (Day 5).

Glucose

Figure 12:
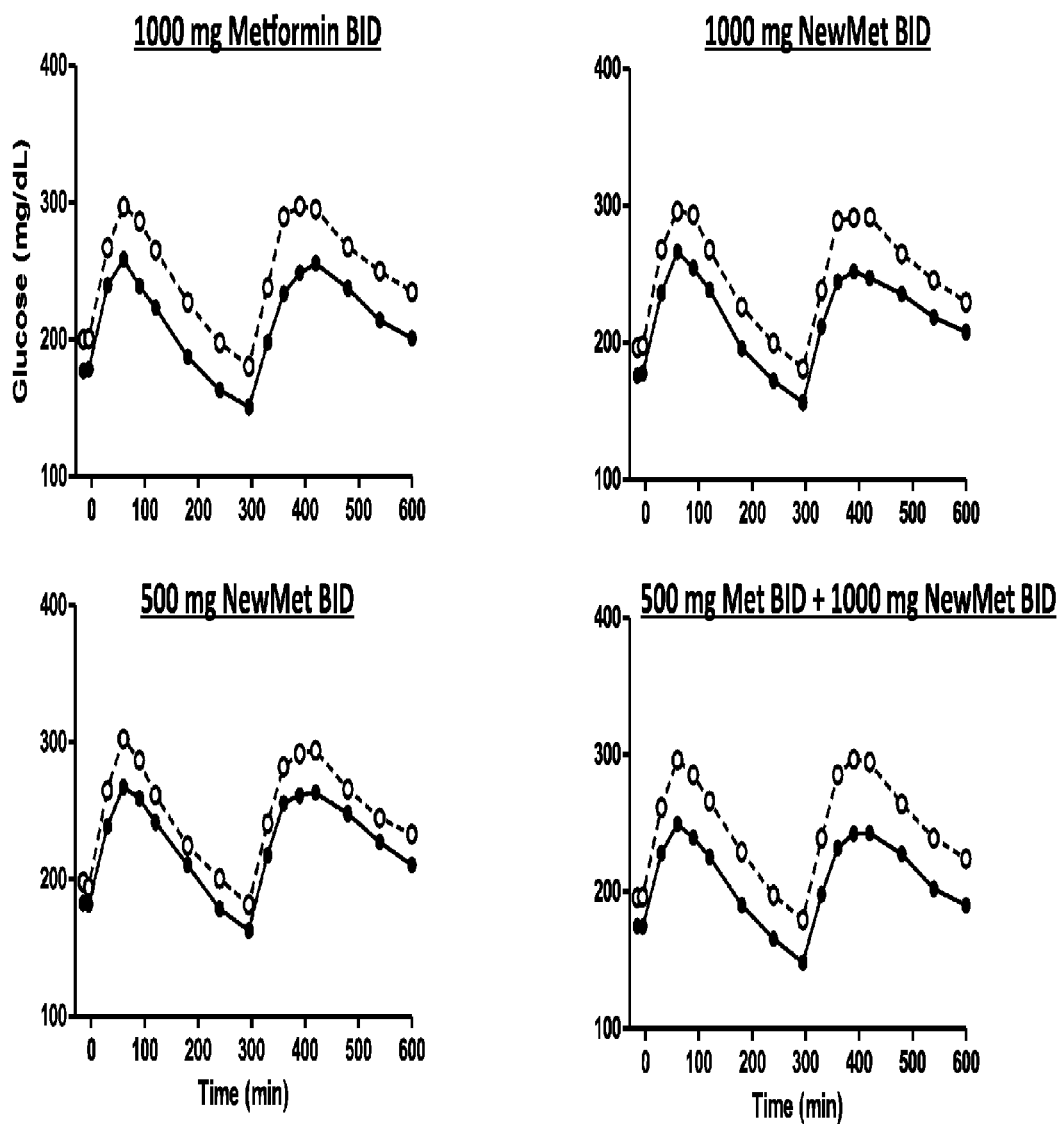
FIG. 12 shows the mean plasma glucose concentration (x-axis; mg/dL) as a function of time (y-axis; min) in subjects at baseline (○) or Day 5 of the designated treatment (●).

FIG. 12 and Table 12 present mean plasma glucose concentration profiles at baseline and Day 5 by treatment and timepoint and the corresponding pharmacodynamic parameters by meal, respectively.

Baseline plasma glucose concentrations were similar between treatments at most time points. Additionally, all metformin treatments statistically significantly decreased glucose exposure and peak concentrations for both meal intervals to a similar extent (p<0.001 for all).

TABLE 12

Pharmacodynamic Analysis of Plasma Glucose (mg/dL) by Meal Interval - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| Breakfast Interval | | | | |
| $AUC_{0-t295}$ (mg/dL * min) | | | | |
| BL geo. LS mean (SE) | 66642 (5480) | 66257 (5815) | 65755 (5906) | 66507 (5617) |
| EOT geo. LS mean (SE) | 57007 (4688) | 59269 (5201) | 60346 (5420) | 56658 (4785) |
| % ratio [1] | | | | |
| Geo. LS mean (SE) | 0.86 (0.02) | 0.90 (0.02) | 0.92 (0.01) | 0.85 (0.02) |
| 95% CI | 0.81, 0.91 | 0.86, 0.93 | 0.89, 0.95 | 0.81, 0.90 |
| p value | <0.0001 | <0.0001 | <0.0001 | <0.0001 |

TABLE 12-continued

Pharmacodynamic Analysis of Plasma Glucose (mg/dL) by Meal Interval - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| $Cmax_{0-t295}$ (mg/dL) | | | | |
| BL geo. LS mean (SE) | 291 (21) | 290 (22) | 292 (24) | 290 (20) |
| EOT geo. LS mean (SE) | 255 (19) | 261 (20) | 263 (21) | 248 (17) |
| % ratio [1] | | | | |
| Geo. LS mean (SE) | 0.88 (0.02) | 0.90 (0.02) | 0.90 (0.01) | 0.85 (0.02) |
| 95% CI | 0.83, 0.92 | 0.86, 0.95 | 0.88, 0.93 | 0.81, 0.90 |
| p value | <0.0001 | 0.0004 | <0.0001 | <0.0001 |
| Lunch Interval $AUC_{t295-t}$ (pg/mL * min) | | | | |
| BL geo. LS mean (SE) | 76286 (6051) | 75132 (6199) | 74566 (6634) | 74799 (5972) |
| EOT geo. LS mean (SE) | 65558 (5200) | 66330 (5473) | 68480 (6093) | 63495 (5070) |
| % ratio [1] | | | | |
| Geo. LS mean (SE) | 0.86 (0.02) | 0.88 (0.02) | 0.92 (0.02) | 0.85 (0.03) |
| 95% CI | 0.82, 0.91 | 0.85, 0.92 | 0.88, 0.95 | 0.79, 0.91 |
| p value | <0.0001 | <0.0001 | 0.0002 | 0.0001 |
| $Cmax_{t295-t}$ (pg/mL) | | | | |
| BL geo. LS mean (SE) | 295 (22) | 288 (21) | 287 (23) | 293 (22) |
| EOT geo. LS mean (SE) | 250 (19) | 255 (19) | 265 (22) | 245 (19) |
| % ratio [1] | | | | |
| Geo. LS mean (SE) | 0.85 (0.03) | 0.89 (0.02) | 0.93 (0.02) | 0.84 (0.03) |
| 95% CI | 0.80, 0.90 | 0.85, 0.92 | 0.89, 0.96 | 0.78, 0.90 |
| p value | <0.0001 | <0.0001 | 0.0002 | <0.0001 |

Abbreviations:
BL = baseline (Day 1);
EOT = end of treatment (Day 5);
t = last quantifiable concentration following dose administration.
[1] EOT (Day 5)/BL (Day 1) for each treatment.

Table 13 presents the pharmacodynamic parameters for glucose from t=0 to time of last concentration after study medication administration. Consistent with the pharmacodynamic parameters for the breakfast and lunch intervals, all metformin treatments statistically significantly decreased glucose exposure and peak concentrations (p<0.001 for all), with percent ratios (Day5/Day1) for $AUC_{0-t}$ and Cmax ranging from 0.84 to 0.92.

TABLE 13

Pharmacodynamic Analysis of Plasma Glucose (mg/dL) and Insulin (pmol/L) - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| Glucose $AUC_{0-t}$ (mg/dL * min) | | | | |
| BL geo. LS mean (SE) | 143041 (11408) | 141572 (11884) | 140503 (12403) | 141502 (11477) |
| EOT geo. LS mean (SE) | 122748 (9789) | 125742 (10556) | 129029 (11390) | 120255 (9754) |
| % ratio [1] | | | | |
| Geo. LS mean (SE) | 0.86 (0.02) | 0.89 (0.01) | 0.92 (0.01) | 0.85 (0.02) |
| 95% CI | 0.82, 0.90 | 0.86, 0.92 | 0.89, 0.95 | 0.80, 0.90 |
| p value | <0.0001 | <0.0001 | <0.0001 | <0.0001 |
| $Cmax_{0-t}$ (mg/dL) | | | | |
| BL geo. LS mean (SE) | 301 (22) | 301 (22) | 301 (24) | 304 (22) |
| EOT geo. LS mean (SE) | 265 (19) | 269 (19) | 277 (22) | 256 (19) |
| % ratio [1] | | | | |
| Geo. LS mean (SE) | 0.88 (0.03) | 0.89 (0.02) | 0.92 (0.01) | 0.84 (0.02) |
| 95% CI | 0.83, 0.93 | 0.86, 0.93 | 0.90, 0.95 | 0.79, 0.90 |
| p value | 0.0002 | <0.0001 | <0.0001 | <0.0001 |
| Insulin | | | | |

TABLE 13-continued

Pharmacodynamic Analysis of Plasma Glucose (mg/dL) and Insulin (pmol/L) - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| $AUC_{0-t}$ (pmol/L * min) | | | | |
| BL geo. LS mean (SE) | 191826 (26987) | 176384 (30776) | 199339 (28758) | 191204 (26683) |
| EOT geo. LS mean (SE) | 186379 (26145) | 175190 (30567) | 194650 (28049) | 184975 (25814) |
| % ratio [1] | | | | |
| Geo. LS mean (SE) | 0.97 (0.05) | 0.99 (0.04) | 0.98 (0.03) | 0.97 (0.04) |
| 95% CI | 0.88, 1.08 | 0.92, 1.08 | 0.91, 1.04 | 0.89, 1.05 |
| p value | 0.5587 | 0.8622 | 0.4551 | 0.4070 |
| $Cmax_{0-t}$ (pmol/L) | | | | |
| BL geo. LS mean (SE) | 594 (88) | 664 (112) | 604 (96) | 598 (92) |
| EOT geo. LS mean (SE) | 539 (80) | 586 (99) | 578 (92) | 539 (83) |
| % ratio [1] | | | | |
| Geo. LS mean (SE) | 0.91 (0.06) | 0.88 (0.09) | 0.96 (0.06) | 0.90 (0.06) |
| 95% CI | 0.79, 1.04 | 0.72, 1.08 | 0.85, 1.08 | 0.79, 1.03 |
| p value | 0.1462 | 0.2167 | 0.4649 | 0.1110 |

Abbreviations:
BL = baseline (Day 1);
EOT = end of treatment (Day 5);
t = last quantifiable concentration following dose administration.
[1] EOT (Day 5)/BL (Day 1) for each treatment.

Figure 13:
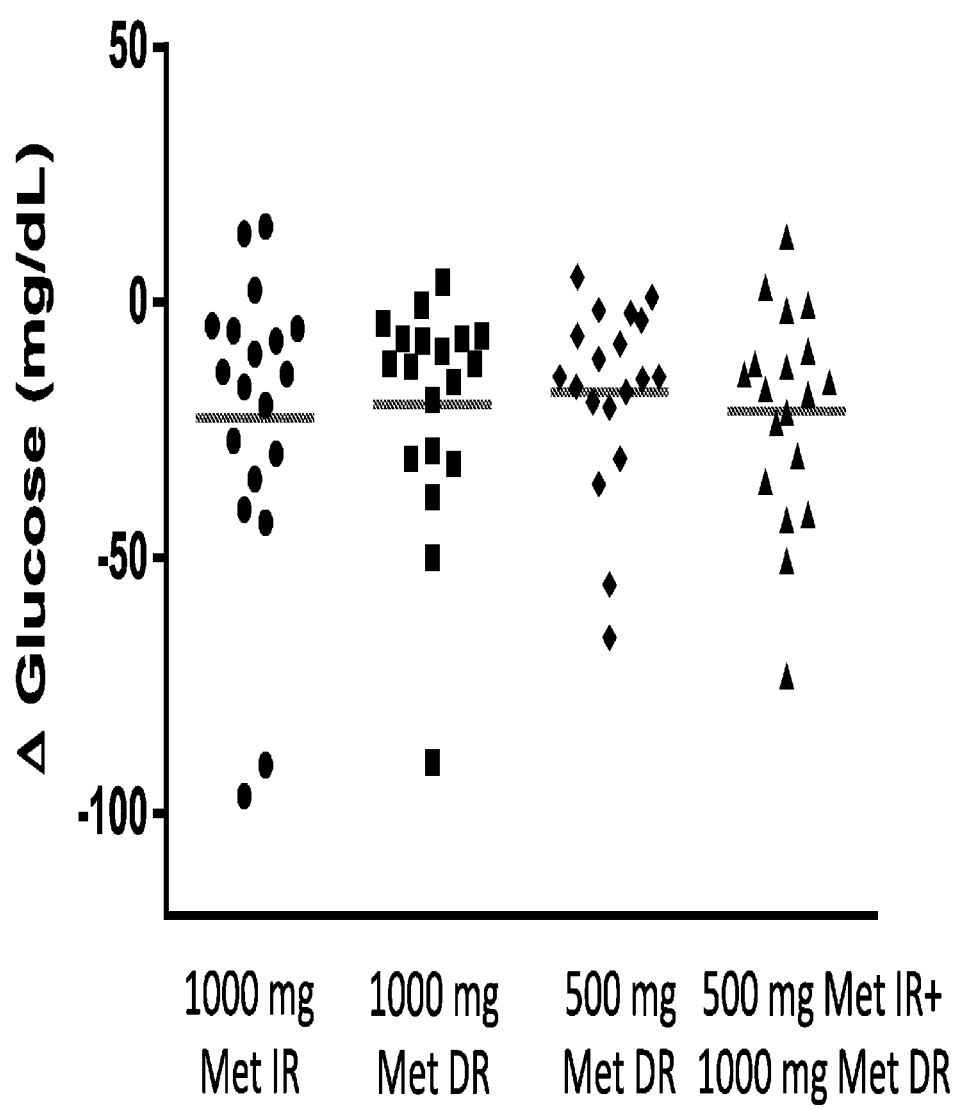
FIG. 13 shows the individual change in fasting plasma glucose concentrations (x-axis; mg/dL) as a function of time (y-axis; min) from baseline to Day 5 by scatterplot in subjects treated with 500 mg (♦) and 1000 mg (■) Metformin DR, 1000 mg Metformin IR (●), and 500 mg Metformin IR+1000 mg Metformin DR (▲)(y-axis) The line in the panel marks the LS Mean Change in glucose (mg/dL) for each treatment.

Table 14 presents the LS mean (SE) and FIG. 13 presents the individual change in fasting plasma glucose concentrations from baseline to Day 5 by treatment. Baseline fasting glucose concentrations were similar and ranged from 196 mg/dL to 200 mg/dL among the treatment groups. All treatment groups achieved statistically significant reductions (p<0.01 for all) in fasting plasma glucose after 5 days of treatment. As shown in FIG. 13, the LSM and distribution of individual responses were similar between treatment groups.

Insulin

Tables 15 and 16 present the pharmacodynamic parameters for insulin and baseline and Day 5 fasting plasma insulin concentrations, respectively. There were no statistically significant changes in insulin exposure, peak concentrations, or fasting concentrations for any of the treatments (p>0.05 for all). Maintenance of insulin concentrations despite the lower circulating glucose concentrations is indicative of an incretin effect.

TABLE 14

Fasting Plasma Glucose (mg/dL) at Baseline and Day 5 - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| BL LS mean (SE) | 200.3 (16.2) | 197.0 (16.7) | 198.7 (17.4) | 195.9 (15.4) |
| EOT LS mean (SE) | 177.8 (16.2) | 177.1 (16.7) | 182.2 (17.4) | 174.7 (15.4) |
| LS mean diff (SE) | −22.5 (6.8) | −19.9 (5.0) | −16.4 (3.8) | −21.2 (4.7) |
| 95% CI | −36.8, −8.16 | −30.5, −9.3 | −24.5, −8.4 | −31.1, −11.2 |
| p value | 0.0040 | 0.0009 | 0.0004 | 0.0003 |

Abbreviations:
BL = baseline (Day 1);
EOT = end of treatment (Day 5).

TABLE 15

Pharmacodynamic Analysis of Insulin (pmol/L) - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| $AUC_{0-t}$ (pmol/L * min) | | | | |
| BL geo. LS mean (SE) | 191826 (26987) | 176384 (30776) | 199339 (28758) | 191204 (26683) |
| EOT geo. LS mean (SE) | 186379 (26145) | 175190 (30567) | 194650 (28049) | 184975 (25814) |

TABLE 15-continued

Pharmacodynamic Analysis of Insulin (pmol/L) - Within-Treatment Comparison Based on Ratios - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| % ratio [1] | | | | |
| Geo. LS mean (SE) | 0.97 (0.05) | 0.99 (0.04) | 0.98 (0.03) | 0.97 (0.04) |
| 95% CI | 0.88, 1.08 | 0.92, 1.08 | 0.91, 1.04 | 0.89, 1.05 |
| p value | 0.5587 | 0.8622 | 0.4551 | 0.4070 |
| $Cmax_{0-t}$ (pmol/L) | | | | |
| BL geo. LS mean (SE) | 594 (88) | 664 (112) | 604 (96) | 598 (92) |
| EOT geo. LS mean (SE) | 539 (80) | 586 (99) | 578 (92) | 539 (83) |
| % ratio [1] | | | | |
| Geo. LS mean (SE) | 0.91 (0.06) | 0.88 (0.09) | 0.96 (0.06) | 0.90 (0.06) |
| 95% CI | 0.79, 1.04 | 0.72, 1.08 | 0.85, 1.08 | 0.79, 1.03 |
| p value | 0.1462 | 0.2167 | 0.4649 | 0.1110 |

Abbreviations:
BL = baseline (Day 1);
EOT = end of treatment (Day 5);
t = last quantifiable concentration following dose administration.
[1] EOT (Day 5)/BL (Day 1) for each treatment.

TABLE 16

Fasting Insulin (pmol/L) at Baseline and Day 5 - Evaluable Population

| Statistic | 1000 mg Met IR (N = 19) | 1000 mg Met DR (N = 19) | 500 mg Met DR (N = 19) | 500 mg Met IR + 1000 mg Met DR (N = 19) |
|---|---|---|---|---|
| BL LS mean (SE) | 183.8 (42.3) | 187.7 (29.0) | 166.7 (34.5) | 169.8 (29.9) |
| EOT LS mean (SE) | 151.9 (42.3) | 138.1 (29.0) | 157.8 (34.5) | 147.0 (29.9) |
| LS mean diff (SE) | −31.8 (30.8) | −49.6 (18.1) | −8.8 (13.2) | −22.8 (8.6) |
| 95% CI | −96.5, 32.8 | −87.7, −11.6 | −36.6, 18.9 | −40.8, −4.8 |
| p value | 0.3146 | 0.0135 | 0.5109 | 0.0160 |

Abbreviations:
BL = baseline (Day 1);
EOT = end of treatment (Day 5).

Safety Evaluations

Table 17 summarizes treatment-emergent adverse events by SOC, preferred term, and most recent treatment at onset.

Consistent with the metformin prescribing information, adverse events were primarily gastrointestinal in nature with nausea, vomiting, and retching occurring only in the treatment groups receiving Metformin IR with or without Metformin DR. Diarrhea was reported across all treatment groups and appeared to be dose-dependent with the greatest incidence with Metformin IR+Metformin DR (7 subjects, 33.3%) and the lowest incidence with the lowest dose of Metformin DR (2 subjects, 10.0%). Of note, all gastrointestinal events in the 500 mg Metformin DR group occurred during the post-treatment washout period while off study drug. Nervous system disorders such as dizziness and headache were also more frequent with Metformin IR than either DR dosage. Overall, fewer gastrointestinal and nervous system disorder adverse events were reported with the Metformin DR than metformin IR, indicating that the reduced systemic exposure to metformin achieved by bypassing the proximal small intestine improved tolerability.

TABLE 17

Summary of Treatment-Emergent Adverse Events by SOC and Preferred Term and Treatment at Onset - ITT Population

| SOC Preferred Term | 1000 mg Met IR (N = 22) n (%) | 1000 mg Met DR (N = 20) n (%) | 500 mg Met DR (N = 20) n (%) | 500 mg Met IR + 1000 mg Met DR (N = 21) n (%) |
|---|---|---|---|---|
| Any TEAE | 6 (27.3) | 5 (25.0) | 4 (20.0) | 10 (47.6) |
| Gastrointestinal Disorders | 5 (22.7) | 3 (15.0) | 2 (10.0) | 8 (38.1) |
| Abdominal Discomfort | 0 (0) | 0 (0) | 0 (0) | 1 (4.8) |
| Abdominal Distension | 0 (0) | 0 (0) | 0 (0) | 1 (4.8) |

TABLE 17-continued

Summary of Treatment-Emergent Adverse Events by SOC and Preferred Term and Treatment at Onset - ITT Population

| SOC<br>Preferred Term | 1000 mg Met IR<br>(N = 22)<br>n (%) | 1000 mg Met DR<br>(N = 20)<br>n (%) | 500 mg Met DR<br>(N = 20)<br>n (%) | 500 mg Met IR +<br>1000 mg Met DR<br>(N = 21)<br>n (%) |
|---|---|---|---|---|
| Abdominal Pain | 0 (0) | 0 (0) | 1 (5.0) | 1 (4.8) |
| Diarrhea | 3 (13.6) | 3 (15.0) | 2 (10.0) | 7 (33.3) |
| Dyspepsia | 1 (4.5) | 0 (0) | 1 (5.0) | 1 (4.8) |
| Frequent Bowel Movements | 0 (0) | 0 (0) | 0 (0) | 1 (4.8) |
| Nausea | 2 (9.1) | 0 (0) | 0 (0) | 3 (14.3) |
| Retching | 1 (4.5) | 0 (0) | 0 (0) | 0 (0) |
| Vomiting | 2 (9.1) | 0 (0) | 0 (0) | 0 (0) |
| General Disorders And Administration Site Conditions | 0 (0) | 0 (0) | 1 (5.0) | 0 (0) |
| Fatigue | 0 (0) | 0 (0) | 1 (5.0) | 0 (0) |
| Infections And Infestations | 0 (0) | 0 (0) | 0 (0) | 1 (4.8) |
| Oral Herpes | 0 (0) | 0 (0) | 0 (0) | 1 (4.8) |
| Investigations | 0 (0) | 0 (0) | 0 (0) | 1 (4.8) |
| Weight Decreased | 0 (0) | 0 (0) | 0 (0) | 1 (4.8) |
| Musculoskeletal And Connective Tissue Disorders | 0 (0) | 1 (5.0) | 0 (0) | 0 (0) |
| Pain In Extremity | 0 (0) | 1 (5.0) | 0 (0) | 0 (0) |
| Neoplasms Benign, Malignant And Unspecified (Incl Cysts And Polyps) | 0 (0) | 1 (5.0) | 0 (0) | 0 (0) |
| Gastrointestinal Stromal Tumour | 0 (0) | 1 (5.0) | 0 (0) | 0 (0) |
| Nervous System Disorders | 5 (22.7) | 1 (5.0) | 1 (5.0) | 0 (0) |
| Dizziness | 3 (13.6) | 0 (0) | 0 (0) | 0 (0) |
| Headache | 2 (9.1) | 1 (5.0) | 1 (5.0) | 0 (0) |
| Sinus Headache | 1 (4.5) | 0 (0) | 0 (0) | 0 (0) |
| Renal And Urinary Disorders | 0 (0) | 0 (0) | 0 (0) | 1 (4.8) |
| Pollakiuria | 0 (0) | 0 (0) | 0 (0) | 1 (4.8) |
| Skin And Subcutaneous Tissue Disorders | 0 (0) | 0 (0) | 0 (0) | 1 (4.8) |
| Hyperhidrosis | 0 (0) | 0 (0) | 0 (0) | 1 (4.8) |

Example 2.3

Discussion

In this study, metformin concentrations in plasma were measured over 11 hours at steady-state on the 5th day (FIG. 1) of BID dosing (pre-breakfast and pre-supper) with 1000 mg immediate-release metformin (Metformin IR), 500 mg Metformin DR and 1000 mg Metformin DR, or a combination of 500 mg Metformin IR and 1000 mg Metformin DR. All subjects had type 2 diabetes and received each treatment in a randomized crossover design with a one week washout between treatments.

The observed profiles indicated lower circulating amounts of metformin when using the Metformin DR compared to Metformin IR. The Day 5 pre-dose concentration of metformin with Metformin IR on the morning of Day 5 was 350 ng/mL, which is consistent with steady-state trough concentrations published in the literature. After the administration of Metformin IR on the morning of Day 5, there was a rapid increase in metformin concentration that peaked 90 min after the dose followed by a steady decline for the remainder of the sampling period.

With Metformin DR dosing, the highest concentration of metformin was observed prior to the dose on the morning of Day 5, which was approximately 2 times higher at that time point than those for Metformin IR. Following administration of either dose of Metformin DR, there was a decrease in metformin concentration for the first 240 minutes followed by a small rise in metformin concentration at 360 minutes, which plateaued for the remainder of the sampling period. The entire 11-hour Metformin DR PK profiles remained below the pre-dose concentrations measured at t=0. These results indicate that the absorption profiles for Metformin DR dosing with the evening meal were slowed relative to doses administered with the breakfast meal, consistent with slowed intestinal transit during the sleeping hours. Thus, concentrations throughout the first 240 minutes of the Day 5 profile were predominantly a result of absorption from the Day 4 evening dose and concentrations from 240 minutes through 660 mins were predominantly a result of absorption from the Day 5 morning dose.

Example 3

Analysis of Pharmacokinetic Differences Between Morning and Evening Dosing

To better characterize the pharmacokinetic differences between morning and evening doses, the study of Example 3 was designed to obtain 36-hour PK profiles of Metformin DR at doses of 500 and 1000 mg given at the evening and breakfast meals in healthy subjects. Subjects also received 1000 mg Metformin IR with the evening and breakfast meals and 2000 mg metformin extended-release (Metformin XR) with the evening meal during separate treatment periods. All subjects received each treatment in a randomized crossover design with a one week washout between treatments.

The metformin DR formulation was a US-supplied commercially available film-coated immediate-release tablet containing 500 mg metformin hydrochloride, to which additional coatings (a seal coating and an enteric coating) were applied in order to delay release of the drug in the GI tract until the tablet reaches a pH 6.5 region of the distal small intestine. The tablets are white, biconvex, circular-shaped coated tablets, each containing 500 mg metformin hydrochloride. Inactive ingredients in the commercially available tablet included povidone, magnesium stearate, hypromellose, and polyethylene glycol. Inactive ingredients in the additional coating systems included hypromellose, triacetin, talc, methacrylic acid copolymer (Eudragit® L30 D-55), poly(methyl acrylate-co-methyl methacrylate-co-methacrylic acid) 7:3:1 (Eudragit® FS 30 D), sodium lauryl sulfate, polysorbate 80, glyceryl monostearate, and triethyl citrate. The metformin IR and metformin XR formulations were commercially available formulations (Aurobindo Pharma Limited and Bristol-Myers Squibb respectively) without any modification.

Figure 14:
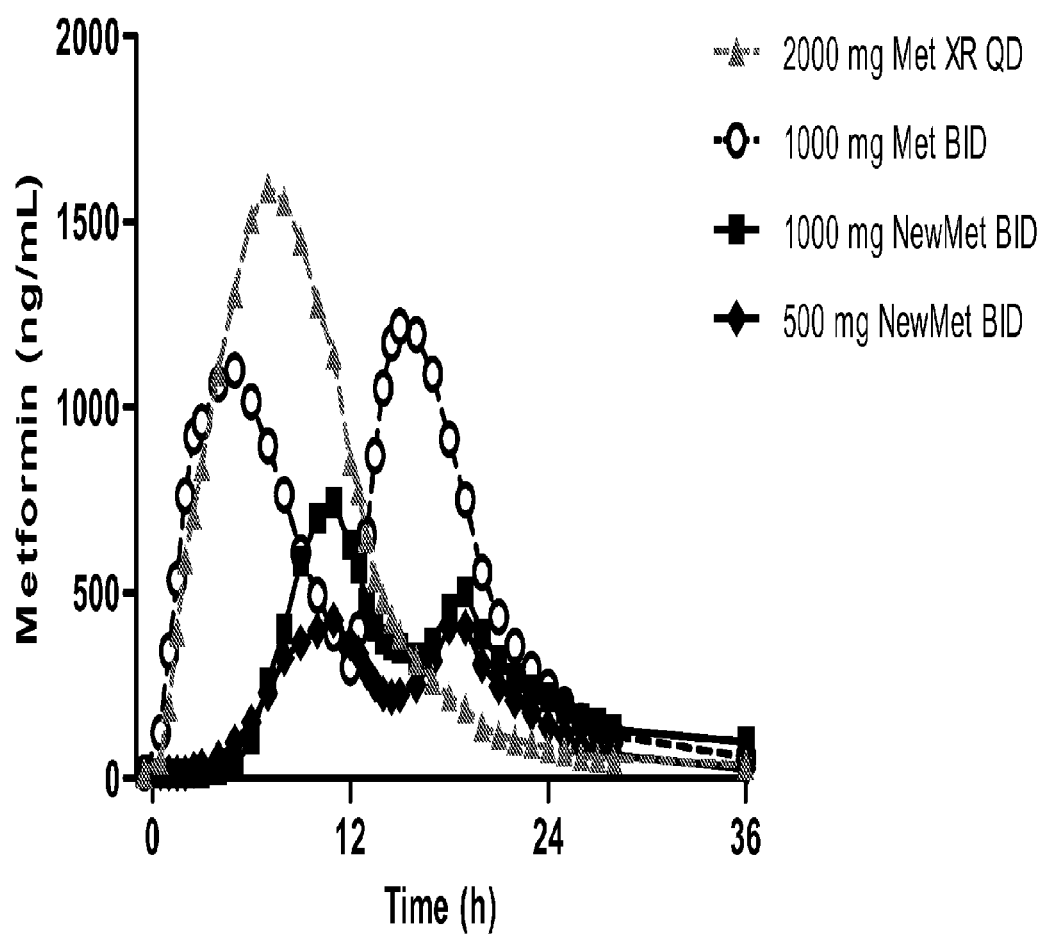
FIG. 14 shows the mean plasma metformin concentration (x-axis; ng/mL) of 500 mg (♦) and 1000 mg (■) Metformin DR, 1000 mg Metformin IR (○), and 2000 mg metformin extended release (Metformin XR) a function of time (y-axis; hours). Dose was administered at t=0 hours. Second dose was administered for BID regimens at t=12 hours. Meals/snacks were provided at t=−0.42, 2.08, 11.5, 18 and 24 hours.

As shown in FIG. 14, both doses of Metformin DR resulted in substantially less systemic metformin than was observed with either Metformin IR or Metformin XR. Of note, the total plasma metformin exposure as measured by AUC of 1000 mg Metformin IR BID and 2000 mg Metformin XR QD (total daily doses of 2000 mg) were very similar, consistent with the previously established bioequivalence between the two formulations. The Metformin DR profile over the first 12 hours showed that there is a delay in systemic absorption of Metformin DR, with the first quantifiable plasma concentration occurring approximately 6-7 hours after the dose. The highest concentration was achieved approximately 11 hours after the evening dose. After a second dose with Metformin DR in the morning, the plasma concentration of metformin decreased until approximately 15 h post first dose, followed by a small rise corresponding to approximately 3 hours after the second dose.

As noted above, the data indicate that Metformin IR and both doses of Metformin DR have slightly greater bioavailability after an evening dose than the morning dose, perhaps as a result of slower intestinal transit during the sleeping hours.

Figure 15:
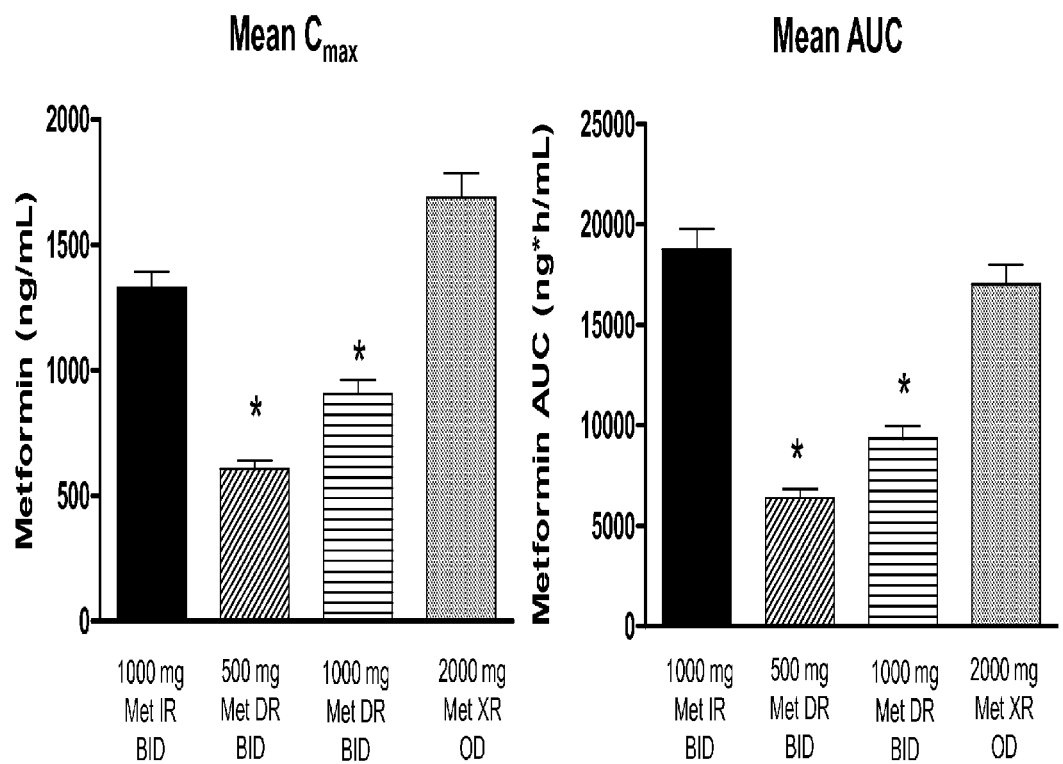
FIG. 15 shows the $C_{max}$ (left panel) and $AUC_{0-36}$ (right panel) of one day's dosing of 1000 mg BID metformin IR, 500 mg BID and 1000 mg BID of Metformin DR and 2000 mg QD metformin XR. The * signifies a statistically significant reduction in exposure compared to both metformin IR and metformin XR (all p<0.0001)

Table 18 shows the Mean (CV %) plasma pharmacokinetic parameters of metformin following oral administration of each treatment and FIG. 15 compares the mean (SEM) values of $C_{max}$ (left panel) and $AUC_{0-36\ hr}$ (right panel). Both doses of Metformin DR resulted in substantial reductions in exposure as well as a delay in absorption of 6-7 hours.

TABLE 18

Mean (CV %) Plasma Pharmacokinetic Parameters of Metformin Following Oral Administration of Treatment A, B, C, and D - Evaluable Population

| PK Parameters | 1000 mg Met IR BID (Treatment A) | 500 mg Met DR BID (Treatment B) | 1000 mg Met DR BID (Treatment C) | 2000 mg Met XR QD (Treatment D) |
|---|---|---|---|---|
| N | 19 | 19 | 19 | 19 |
| $AUC_{0-24}$ (ng * h/mL) | 17361 (24.3) | 5541 (31.9) | 7634 (31.9) | 16406 (24.5) |
| $AUC_{0-t}$ (ng * h/mL) | 18709 (24.3) | 6164 (32.9) | 9014 (29.5) | 16989 (24.8) |
| $AUC_{0-\infty}$ (ng * h/mL) | 19423 (23.6) | 6690 (30.4)[b] | 10277 (25.6)[b] | 17398 (24.7) |
| $C_{max}$ (ng/mL) | 1328 (20.6) | 607 (24.0) | 905 (26.8) | 1688 (25.0) |
| $t_{max}$[a] (h) | 15.0 (4.00, 16.0) | 11.0 (6.02, 19.0) | 11.0 (7.00, 19.0) | 7.05 (6.00, 11.0) |
| $t_{lag}$[a] (h) | 0.00 (0.00, 0.500) | 6.02 (1.50, 10.0) | 7.00 (3.00, 8.00) | 0.00 (0.00, 2.00) |
| $t_{1/2}$ (h) | 8.26 (31.0) | 6.19 (49.4)[b] | 11.2 (39.9)[b] | 6.09 (45.5) |

[a]median (min, max)
[b]n = 18
[c]n = 17

Figure 16:
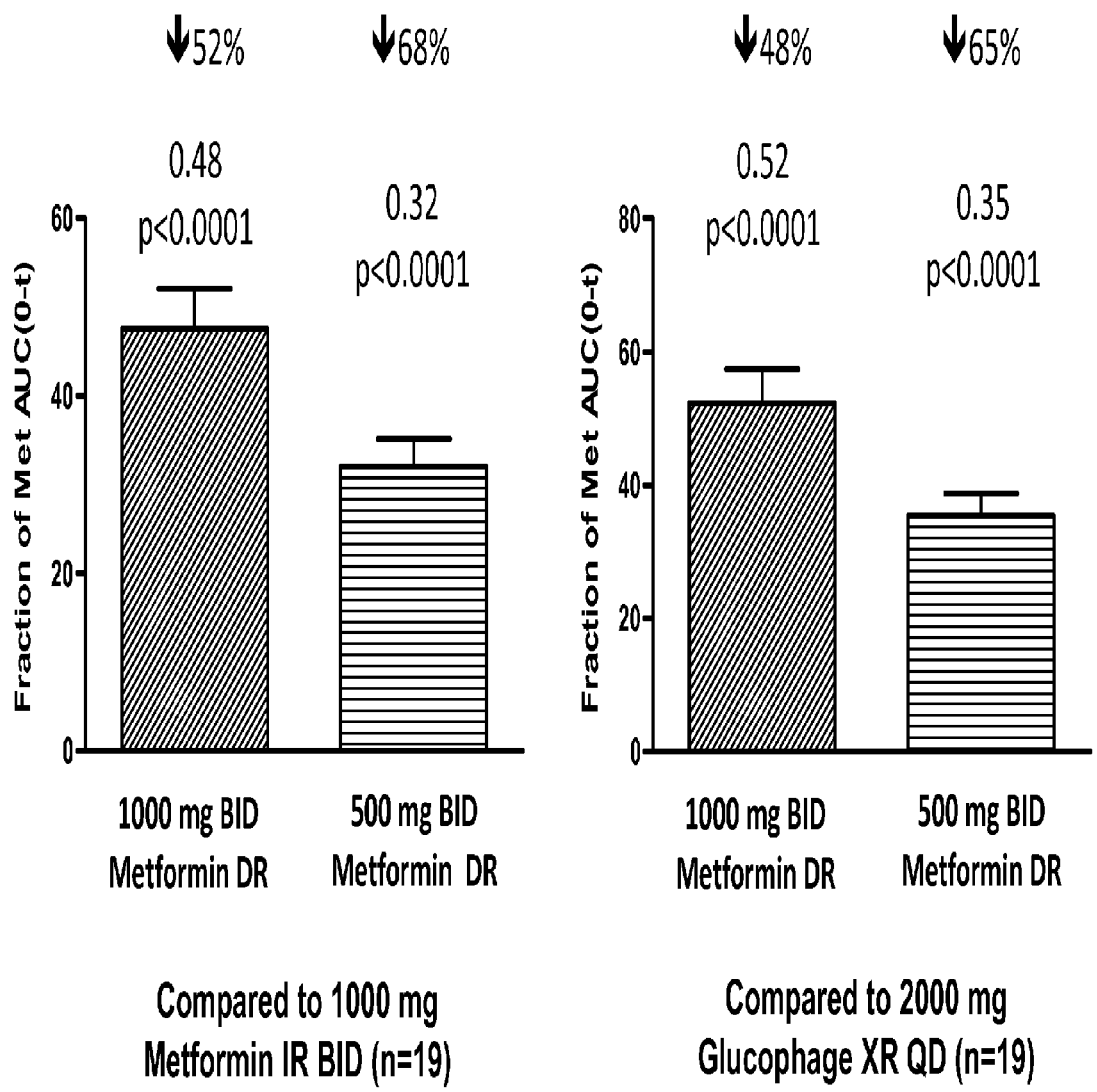
FIG. 16 shows the relative bioavailability of one day's dosing of 500 and 1000 mg BID Metformin DR compared to 1000 mg BID Metformin IR (left panel) and the relative bioavailability of one day's dosing of 500 and 1000 mg BID Metformin DR compared to 2000 mg QD Metformin XR (right panel)

Geometric LSM ratios and 90% confidence intervals for the ln-transformed $C_{max}$, $AUC_{0-t}$, and $AUC_{0-\infty}$ from the Metformin DR treatments (500 mg BID [Treatment B] and 1000 mg BID [Treatment C]) relative to the Metformin IR (1000 mg BID [Treatment A]) are shown in Table 19 and the relative bioavailability is plotted in the left panel of FIG. 16. These results indicate that the rate and extent of exposure ($C_{max}$, $AUC_{0-t}$ and $AUC_{0-28}$) from 500 mg BID Metformin DR were approximately 55%, 68% and 67% lower, respectively, than those from 1000 mg BID Metformin IR. At 1000 mg BID Metformin DR (Treatment C, total daily dose of 2000 mg metformin) the rate and extent of exposure ($C_{max}$, $AUC_{0-t}$ and $AUC_{0-\infty}$) were approximately 33%, 52% and 47% lower, respectively, than those from 1000 mg BID Metformin IR (Treatment A, total daily dose of 2000 mg metformin). Similar reductions in the rate and extent of exposure were observed when 500 mg BID and 1000 mg BID of Metformin DR were compared to 2000 mg QD of Metformin XR (Table 20; FIG. 16, right panel).

TABLE 19

Relative Bioavailability of Metformin Following Oral Administration of
500 mg BID and 1000 mg BID Metformin DR Treatment compared to
1000 mg BID Metformin IR - Evaluable Population

| PK Parameter | Geometric Least-Square Means | | | % Ratio of LSmeans (90% CI) | | p-value | |
|---|---|---|---|---|---|---|---|
| | A | B | C | B/A | C/A | B/A | C/A |
| $AUC_{0-t}$ (ng*h/mL) | 18116 | 5816 | 8611 | 32.1 (29.30-35.18) | 47.5 (43.38-52.09) | SS | SS |
| $AUC_{0-\infty}$ (ng*h/mL) | 19981 | 6644 | 10586 | 33.3 (30.37-36.40) | 53.0 (48.36-58.05) | SS | SS |
| $C_{max}$ (ng/mL) | 1294 | 586 | 865 | 45.3 (40.88-50.13) | 66.8 (60.34-74.00) | SS | SS |

SS: Statistically significant (p-value <0.0001)
Treatment A: 1000 mg Metformin IR BID (2 × 500 mg metformin HCl tablets [immediate-release])
Treatment B: 500 mg Metformin DR BID (1 × 500 mg metformin HCl tablet [delayed-release pH 6.5 enteric-coated])
Treatment C: 1000 mg Metformin DR BID (2 × 500 mg metformin HCl tablets [delayed-release pH 6.5 enteric-coated])

TABLE 20

Relative Bioavailability of Metformin Following Oral Administration of
500 mg BID and 1000 mg BID Metformin DR Treatment compared to
2000 mg QD Metformin XR - Evaluable Population

| PK Parameter | Geometric Least-Square Means | | | % Ratio of LSmeans (90% CI) | | p-value | |
|---|---|---|---|---|---|---|---|
| | B | C | D | B/D | C/D | B/D | C/D |
| $AUC_{0-t}$ (ng*h/mL) | 5816 | 8611 | 16450 | 35.4 (32.27-38.74) | 52.3 (47.77-57.36) | SS | SS |
| $AUC_{0-\infty}$ (ng*h/mL) | 6644 | 10586 | 17873 | 37.2 (33.93-40.73) | 59.2 (54.10-64.84) | SS | SS |
| $C_{max}$ (ng/mL) | 586 | 865 | 1631 | 35.9 (32.43-39.77) | 53.0 (47.88-58.71) | SS | SS |

SS: Statistically significant (p-value <0.0001)
Treatment B: 500 mg Metformin DR BID (1 × 500 mg metformin HCl tablet [delayed-release pH 6.5 enteric-coated])
Treatment C: 1000 mg Metformin DR BID (2 × 500 mg metformin HCl tablets [delayed-release pH 6.5 enteric-coated])
Treatment D: 2000 mg Metformin XR QD (4 × 500 mg metformin HCl tablets [extended-release])

Taken together, the pharmacokinetic results of Examples 2 and 3 indicate that delivery of metformin to the lower bowel by administering Metformin DR reduces 24 hour bioavailability by approximately 50% relative to Metformin IR and Metformin XR at the same daily dose. Greater reductions in exposure were observed when the Metformin DR dose was reduced from a total daily dose of 2000 mg to 1000 mg, without a reduction in efficacy. In addition, the time of Metformin DR dosing (with the morning or evening meals) meaningfully affected the timing of metformin release in the intestine (3 vs. 6-7 hours post-dose, respectively) and provides an explanation for the observation from the study in Example 2 that, the Metformin DR trough values observed prior to the morning dose were higher than the trough values observed 12 hours after the morning dose.

In the Example 2 study, while the systemic exposure to metformin was substantially reduced with Metformin DR (45% with 2000 mg/day and ~60% with 1000 mg/day, relative to 2000 mg/day of Metformin IR), the full glucose lowering effects of Metformin IR (2000 mg/day) were maintained. Given that the full glucose lowering effect was observed at both 2000 mg and 1000 mg daily of Metformin DR, lower doses are viable, allowing for more elegant dosage forms than are currently available with existing products (Metformin IR and Metformin XR (i.e., smaller tablets, fully effective fixed dose combinations, once daily dosing). Moreover, unlike Metformin IR, Metformin DR was not associated with any nausea and vomiting at either dose.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A method of treating a subject having diabetes and moderate or severe renal impairment, comprising administering a therapeutically effective amount of metformin or a salt thereof to said subject in a delayed-release formulation, wherein the delayed-release formulation releases a therapeutically effective amount of said metformin or a salt thereof distal of the duodenum, to one or more regions of the intestine, and wherein the resulting circulating plasma concentration of the metformin is below about 1 μg/mL.

2. The method according to claim 1, wherein the metformin has a reduced relative average bioavailability of about 40, 50 or 60% in said delayed-release formulation in comparison with an immediate-release formulation having the same amount of said metformin or salt thereof.

3. The method according to claim 1, wherein the administration produces a mean plasma $AUC_{0-36}$ less than about 14,000, 13,000 or 12,000 ng*h/mL when said formulation is administered at 1000 mg total daily dose.

4. The method according to claim 1, wherein the mean plasma $C_{max}$ of said metformin is less than about 1100 ng/ml when administered at 1000 mg total daily dose.

5. The method according to claim 1, wherein the delayed-release formulation comprises about 1 mg to about 2000 mg of metformin or a salt thereof.

6. A method according to claim 1, further comprising administration of a DPP-IV inhibitor.

7. A method according to claim 1, further comprising administration of an anti-obesity or anti-diabetes agent.

8. The method according to claim 1, wherein said metformin or a salt thereof is metformin hydrochloride.

9. The method according to claim 1, wherein the circulating plasma concentration of the metformin is below about 0.5 μg/mL.

10. The method according to claim 1, wherein the circulating plasma concentration of the metformin is below about 0.25 μg/mL.

11. The method according to claim 7, wherein said antidiabetic agent is selected from the group consisting of thiazolidinediones, sulfonylureas, meglitinides, alpha-glucosidase inhibitors, DPP-IV inhibitors, incretin mimetics, and SGLT inhibitors.

12. The method according to claim 7, wherein said anti-obesity agent is lorcaserin.

13. The method according to claim 7, wherein said anti-obesity agent is phentermine.

14. The method according to claim 7, wherein said anti-obesity agent is a combination of lorcaserin and phentermine.

15. The method according to claim 7, wherein said anti-obesity agent is a combination of topiramate and phentermine.

16. The method according to claim 7, wherein said anti-obesity agent is a combination of bupropion and naltrexone.

17. The method according to claim 7, wherein said anti-obesity agent or said anti-diabetes is co-formulated with said metformin or a salt thereof and administered simultaneously in a combined formulation.

18. The method according to claim 17, wherein said combined formulation is provided in the form of a delayed release component coupled with an immediate release component in a unitary dosage form.

19. The method according to claim 1, wherein the delayed-release formulation comprises an enteric coating.

20. The method according to claim 19, wherein the enteric coating has an onset of release of said metformin or a salt thereof at or above about pH 6.5, or above about pH 7.0.

21. The method according to claim 1, wherein the delayed-release formulation has an onset of release of said metformin or a salt thereof at or above about pH 6.5.

22. The method according to claim 1, wherein the delayed-release formulation has an onset of release of said metformin or a salt thereof at or above about pH 7.0.

23. The method according to claim 1, wherein the delayed-release formulation releases a therapeutically effective amount of said metformin or a salt thereof distal of the jejunum, to one or more regions of the intestine.

* * * * *